United States Patent
Kumar et al.

(10) Patent No.: US 10,500,197 B2
(45) Date of Patent: Dec. 10, 2019

(54) USE OF OLIGOPYRIDYLAMIDES TO INHIBIT MUTANT P53 AMYLOID FORMATION AND RESTORE ITS TUMOR SUPPRESSOR FUNCTION

(71) Applicants: New York University, New York, NY (US); New York University in Abu Dhabi Corporation, Abu Dhabi (AE)

(72) Inventors: Sunil Kumar, New York, NY (US); Andrew D. Hamilton, New York, NY (US); Mazin Magzoub, Abu Dhabi (AE); Sarah Hassan, Abu Dhabi (AE)

(73) Assignees: New York University, New York, NY (US); New York University in Abu Dhabi Corporation, Abu Dhabi (AE)

( * ) Notice: Subject to any disclaimer, the term of this patent is extended or adjusted under 35 U.S.C. 154(b) by 0 days.

(21) Appl. No.: 16/038,734

(22) Filed: Jul. 18, 2018

(65) Prior Publication Data
US 2019/0022075 A1     Jan. 24, 2019

Related U.S. Application Data

(60) Provisional application No. 62/533,935, filed on Jul. 18, 2017.

(51) Int. Cl.
*A61K 31/444* (2006.01)
*A61P 35/00* (2006.01)

(52) U.S. Cl.
CPC ............ *A61K 31/444* (2013.01); *A61P 35/00* (2018.01)

(58) Field of Classification Search
CPC ............................ C07D 213/30; A61K 31/444
USPC ......................................................... 514/277
See application file for complete search history.

(56) References Cited

U.S. PATENT DOCUMENTS

| | | |
|---|---|---|
| 4,476,116 A | 10/1984 | Anik |
| 4,511,069 A | 4/1985 | Kalat |
| 4,778,810 A | 10/1988 | Wenig et al. |
| 5,203,840 A | 4/1993 | Graf et al. |
| 5,759,565 A | 6/1998 | Azria et al. |
| 5,860,567 A | 1/1999 | Fuchs et al. |
| 5,893,484 A | 4/1999 | Fuchs et al. |
| 6,227,415 B1 | 5/2001 | Ritsche et al. |
| 6,364,166 B1 | 4/2002 | Ritsche et al. |
| 6,514,496 B1 | 2/2003 | Platz et al. |
| 8,846,074 B2 | 9/2014 | Bryson et al. |
| 2018/0170910 A1* | 6/2018 | Kumar ................ C07D 401/14 |

FOREIGN PATENT DOCUMENTS

| | | |
|---|---|---|
| EP | 0215697 A2 | 3/1978 |
| EP | 0037943 A2 | 10/1981 |
| EP | 0094157 A1 | 11/1983 |
| EP | 0173990 A2 | 3/1986 |
| EP | 0214898 A2 | 3/1987 |
| EP | 0327756 A2 | 8/1989 |
| EP | 0490806 A2 | 6/1992 |
| WO | 2004093917 A2 | 11/2004 |
| WO | 2005120551 A1 | 12/2005 |

OTHER PUBLICATIONS

Gong et al., Curr Protein Pept Sci, 2014 (abstract).*
Rangel et al. Prion, 2014, 8(1): 75-84.*
Willis et al. Oncogene, 2004, 23:2330-2338.*
Cummings, CG et al., "Disrupting Protein-Protein Interactions with non-Peptidic, Small Molecule α-Helix Mimetics" Current Opinion in Chemical Biology (2010) vol. 14, No. 3, pp. 341-346.
Davis, S.S. et al., "Absorption Enhancers for Nasal Drug Delivery" Clin. Pharmacokinet (2003) vol. 42, Issue 13, pp. 1107-1128.
Gannon, J.V. et al., "Activating Mutations in p53 Produce a Common Conformational Effect: A Monoclonal Antibody Specific for the Mutant Form" EMBO Journal (1990) vol. 9, No. 5, pp. 1595-1602.
Garcia-Arieta et al., "Spray-Dried Powders as Nasal Absorption Enhancers of Cyanocobalamin" Biol. Pharm. Bull. (2001) vol. 24, No. 12, pp. 1411-1416.
Gura, T., "Hope in Alzheimer's Fight Emerges from Unexpected Places" Nature Medicine (2008) vol. 14, No. 9, pp. 894-894.
Jayatunga, M.K.P, et al., "α-Helix Mimetics: Outwards and Upwards" Bioorganic & Medicinal Chemistry Letters (2014) vol. 24, No. 3, pp. 717-724.
Kumar, S. et al., "α-Helix Mimetics as Modulators of Aβ Self-Assembly" Journal of the American Chemical Society (2017) vol. 139, No. 16, pp. 5744-5755.
Landers, J.E. et al., "Translational Enhancement of mdm2 Oncogene Expression in Human Tumor Cells Containing a Stabilized Wild-Type p53 Protein" Cancer Research (1997) vol. 57, No. 16, pp. 3562-3568.
Lindberg, D.J. et al., "Thioflavin-T Binding to Amyloid Fibrils Leads to Fluorescence Self-Quenching and Fibril Compaction" Biochemistry (2017) vol. 56, pp. 2170-2174.
Love, I. et al., "p53 Ubiquitination and Proteasomal Degradation" p53 Protocols (2013) pp. 63-73.
Martinez-Zapien, D., "Structure of the E6/E6AP/p53 Complex Required for HPV-Mediated Degradation of p53" Nature (2016) vol. 529, No. 7587, pp. 541-545.
Maslon, M.M et al., "Drug Discovery and Mutant p53" Trends Cell Biology (2010) vol. 20, Issue 9, pp. 542-555.
O'Hagan, DT et al., "Nasal Absorption Enhancers for Biosynthetic Human Growth Hormone in Rats" Pharmacuetical Research (1990) vol. 7, No. 7, pp. 772-776.
Oda, K. et al., "p53AIPI, A Potential Mediator of p53-Dependent Apoptosis, and its Regulation by Ser-46-Phosphorylated p53" Cell (2000) vol. 102, No. 6, pp. 849-862.

(Continued)

*Primary Examiner* — Rei Tsang Shiao
(74) *Attorney, Agent, or Firm* — Troutman Sanders LLP

(57) ABSTRACT

The invention relates to oligopyridylamide alpha-helix mimetic compounds and their use to inhibit p53 aggregation and restore its tumor suppressor function for treating diseases, e.g., cancers, associated with p53 mutations, e.g., R248W p53 mutation.

20 Claims, 13 Drawing Sheets
(13 of 13 Drawing Sheet(s) Filed in Color)

(56) References Cited

OTHER PUBLICATIONS

Qin, Y. et al., "Effect of Resveratrol on Proliferation and Apoptosis of Human Pancreatic Cancer MIA PaCa-2 Cells May Involve Inhibition of the Hedgehog Signaling Pathway" Molecular Medicine Reports (2014) vol. 10, No. 5, pp. 2563-2567.

Rahib, L. et al., "Projecting Cancer Incidence and Deaths to 2030: The Unexpected Burden of Thyroid, Liver, and Pancreas Cancers in the United States" Cancer Research (2014) vol. 74, No. 11, pp. 2913-2921.

Rangel, L.P. et al., "The Aggregation of Mutant p53 Produces Prion-Like Properties in Cancer" Prion (2014) vol. 8, No. 1, pp. 75-84.

Rieger, A.M. et al., "Accurate Assessment of Cell Death by Imaging Flow Cytometry" Imaging Flow Cytometry: Methods and Protocols (2016) pp. 209-220.

Riss, T.L. et al., "Cell Viability Assays" Assay Guidance Manual (2016) 31 pages total.

Schlapschy, M. et al., "PASylation: A Biological Alternative to PEGylation for Extending the Plasma Half-Life of Pharmaceutically Active Proteins" Protein Engineering Design and Selection (2013) vol. 26, No. 8, pp. 489-501.

Sidhar, H. et al., "Induction of Bex Genes by Curcumin is Associated with Apoptosis and Activation of p53 in N2a Neuroblastoma Cells" Scientific Reports (2017) vol. 7, No. 41420, 19 pages total.

Soragni, A. et al., "A Designed Inhibitor of p53 Aggregation Rescues p53 Tumor Suppression in Ovarian Carcinomas" Cancer Cell (2016) vol. 29, No. 1, pp. 90-103.

Svensen, N. et al., "Peptides for Cell-Selective Drug Delivery" Trends in Pharmacological Sciences (2012) vol. 33, No. 4, pp. 186-192.

Villa, LL., "Human Papillomaviruses and Cervical Cancer" Advances in Cancer Research (1997) vol. 71, pp. 321-341.

Vogiatzi, F. et al., "Mutant p53 Promotes Tumor Progression and Metastasis by the Endoplasmic Reticulum UDPase ENTPD5" Proceedings of the National Academy of Sciences (2016) vol. 113, No. 52, pp. E8433-E8442.

Wade, M. et al., "MDMZ, MDMX and p53 in Oncogenesis and Cancer Therapy" Nature Reviews Cancer (2013) vol. 13, No. 2, p. 83.

Wang, G. et al., "Multisite Aggregation of p53 and Implications for Drug Rescue" Proceedings of the National Academy of Sciences (2017) pp. E2634-E2643.

Willis, A. et al., "Mutant p53 Exerts a Dominant Negative Effect by Preventing Wild-Type p53 From Binding to the Promoter of its target genes" Oncogene (2004) vol. 23, No. 13, pp. 2330-2338.

Xu, J. et al., "Gain of Function of Mutant p53 by Coaggregation with multiple Tumor Suppressors" Nature Chemical Biology (2011) vol. 7, pp. 285-295.

Zhao, CY et al., "Rescue of p53 Function by Small-Molecule RITA in Cervical Carcinoma by Blocking E6-Mediated Degradation" Cancer Research (2010) vol. 70, No. 8, pp. 3372-3381.

\* cited by examiner

ADH-31

ADH-37

ADH-39

ADH-40

ADH-41

ADH-46

USE OF OLIGOPYRIDYLAMIDES TO INHIBIT MUTANT P53 AMYLOID FORMATION AND RESTORE ITS TUMOR SUPPRESSOR FUNCTION

CROSS-REFERENCE TO RELATED APPLICATIONS

This application claims priority to U.S. Provisional application Ser. No. 62/533,935, filed on Jul. 18, 2017, the contents of which are incorporated herein by reference in their entirety.

FIELD OF INVENTION

The present invention relates to oligopyridylamide alpha-helix mimetic compounds and their use for inhibiting aggregation of p53 protein to restore its tumor suppressor function for treating diseases, e.g., cancers, associated with p53 mutations, e.g., R248W p53 mutation.

BACKGROUND OF THE INVENTION p53 is a tumor suppressor protein that is heavily involved in important cellular processes, most notably in cell cycle regulation, apoptosis and DNA repair. The full-length wild-type p53 protein binds to several DNA sequences, functioning as a sequence-specific transcriptional activator. Its flexible nature lends it the ability to interact with other proteins, exerting its function as a master regulatory protein and transcription factor. Its roles include maintaining genome integrity and regulating the cell cycle. As such, wild-type p53 is activated in response to cellular stress, such as uncontrolled cell growth, DNA damage and hypoxia. Its function is lost in more than 50% of human cancers with several mutations, all of which are often associated with the most pernicious manifestations of the disease (1). Thus, in recent years, p53 has taken on a pivotal role in the realm of cancer research and has been rendered a key target in the development of modern cancer therapeutics.

Human p53 is a homotetramer—a protein complex that is comprised of four identical monomers, each of which consist an N-terminal transactivation domain, a proline-rich domain, a tetramerization domain and a C-terminal regulatory domain (FIG. 1). Notably, it has been shown that the DNA-binding domain (DBD) of p53 is conformationally unstable; some 95% of p53 mutations occur within this region, which further decreases its stability and prompts protein unfolding or conformational transition (2). These mutations cluster into discernible 'hot-spots', which are sites of identifiable mutations within the DNA-binding domain. Of these many hot-spots disease mutants, two classes have been shown to have great clinical significance. The first class consists of structural mutations, which lead to the partial unfolding of the protein, rendering it functionally inactive. Structural mutants, such as R248Q, are present in approximately 30% of reported clinical cases of p53 mutations. Contact mutants, such as R248W, make up the second class and do not affect the conformational stability of the DNA binding domain. Instead, these mutants are unable to bind to DNA due to a missense mutation in an amino acid residue crucial for DNA interaction. Contact mutants account for approximately 20% of clinical cases3. Despite their mechanistic differences, both classes of these hot-spot disease mutants engender similar phenotypic consequences: loss-of-function, dominant-negative activity and gain-of-oncogenic function. Loss-of-function describes the destruction of p53 DNA-binding ability, which prevents the transcriptional activation of genes that initiate apoptosis or DNA repair. Dominant-negative activity transpires from the assimilation of wild-type p53 protein with its mutant form into tetrameric inclusions, thereby dominantly and negatively suppressing the wild-type protein function, effectively hindering its inherent tumor suppressor functionality. Gain-of-oncogenic function results from the incorporation of p53 paralogs p63 and p73 into these cellular inclusions, which further inhibits the transcription of target genes downstream of p53-activated transcription, ultimately leading to the promotion of tumor metastasis (2).

Previous research has shown that mutant p53 undergoes aggregation in vitro. Using TANGO, a predictive algorithm, residues 251-257 were found to be aggregation-prone. To determine whether these residues are critical for nucleating aggregation, residue 254 was mutated from isoleucine, a hydrophobic residue, to arginine, which is positively charged at physiological pH. Interestingly, not only was the aggregation propensity of the resulting mutant (I254R) nullified, but it was also found that in the presence of I254R, contact and structural mutants failed to aggregate (5).

More recently, it has been found that several p53 DBD mutants form amyloid-like aggregates in tumor cell lines and breast cancer biopsies (4). Being an early event in carcinogenesis, p53 inactivation through mutation is associated with poor response to treatment and high mortality rates. Missense mutations at the R248 site are among the most common in known p53-mutant cancers, including pancreatic carcinoma. Pancreatic cancers do not currently have standard targeted treatments and generally have extremely poor prognoses: it is the seventh most common cause of death from cancer worldwide, with a ten-year survival rate of just 1% (6).

SUMMARY OF THE INVENTION

As specified in the Background section, above, there is a great need in the art to develop new anticancer treatments for cancers associated with p53 mutations. The present invention addresses these and other needs by providing compounds, compositions and associated methods of treatment.

In one aspect, a method of inhibiting aggregation of a p53 protein is provided, comprising contacting said p53 protein with an effective amount of a compound of formula (I):

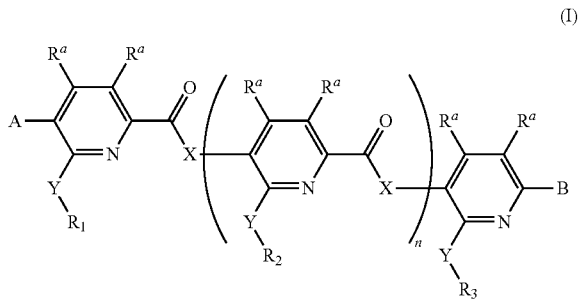

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and —C(R*)$_2$;

Y is independently at each occurrence selected from —O—; —S—; —NH—; and —NR*—;

R$_1$ is selected from hydrogen or a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

R$_2$ is independently at each occurrence selected from hydrogen or a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

R$_3$ is selected from hydrogen or a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

A is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl;

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl;

R* is independently selected at each occurrence from hydrogen or C$_1$-C$_{12}$ hydrocarbons each of which optionally contains 1-8 heteroatoms selected from halogen, O, N, and S and combinations thereof; and n is an integer from 0 to 2;

or a pharmaceutically acceptable salt thereof.

In some embodiments of any of the above treatment methods, (i) when n is 0, and Y is O, R$_1$ and R$_3$ are not both —CH$_2$CO$_2$H; (ii) when n is 1, Y is O, and R$_1$ and R$_3$ are both —CH$_2$CO$_2$H, R$_2$ is not —CH$_2$CO$_2$H or a straight chained, branched or cyclic aliphatic or aryl C$_1$-C$_{12}$ hydrocarbon, or R$_2$ does not have the structure —C(CH$_2$CO$_2$H)$_3$; (iii) when n is 1, and Y is O, R$_1$ through R$_3$ are not each an unsubstituted C$_1$-C$_8$ hydrocarbon; and (iv) when n is 2, and Y is O, R$_1$ through R$_3$ are not —CH$_2$CO$_2$H at all occurrences.

In some embodiments of any of the above treatment methods, the p53 protein comprises one or more mutations.

In some embodiments of any of the above treatment methods, the p53 protein comprises R248W mutation.

In some embodiments of any of the above treatment methods, the p53 protein is in a cell.

In some embodiments of any of the above treatment methods, the cell is in a subject.

In some embodiments of any of the above treatment methods, the compound has the structure according to formula (II):

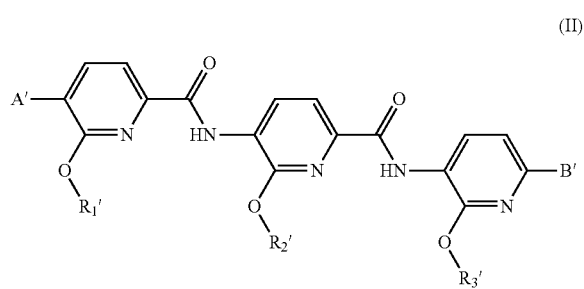

(II)

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof;

$R_2'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3^+$; —(C=O)—$R^*$; —CHO; —$CO_2H$; —$CO_2R^*$; —(C=O)—S—$R^*$; —O—(C=O)—H; —O—(C=O)—$R^*$; and combinations thereof;

A' is selected from —$NO_2$; —$NH_2$; —$NHR^*$; —$N(R^*)$—(C=O)—$R^*$, —$N(R^*)_2$, where $R^*$ is hydrogen or an aliphatic $C_1$-$C_{12}$ hydrocarbon; and B' is selected from —(C=O)—$R^*$; —$CO_2H$; —$CO_2R^*$, where $R^*$ is hydrogen or an aliphatic $C_1$-$C_{12}$ hydrocarbon;

$R^*$ is independently selected at each occurrence from hydrogen or $C_1$-$C_{12}$ hydrocarbons each of which optionally contains 1-8 heteroatoms selected from halogen, O, N, and S and combinations thereof;

or a pharmaceutically acceptable salt thereof.

In some embodiments of any of the above treatment methods, (i) when $R_1$ and $R_3$ are both —$CH_2CO_2H$, $R_2$ is not —$CH_2CO_2H$ or a straight chained, branched or cyclic aliphatic $C_1$-$C_{12}$ hydrocarbon, or $R_2$ does not have the structure —$C[CH_2CO_2H]_3$; and (ii) $R_1$ through $R_3$ are not each an unsubstituted $C_1$-$C_8$ hydrocarbon.

In some embodiments of any of the above treatment methods, the compound has the structure according to the following formula:

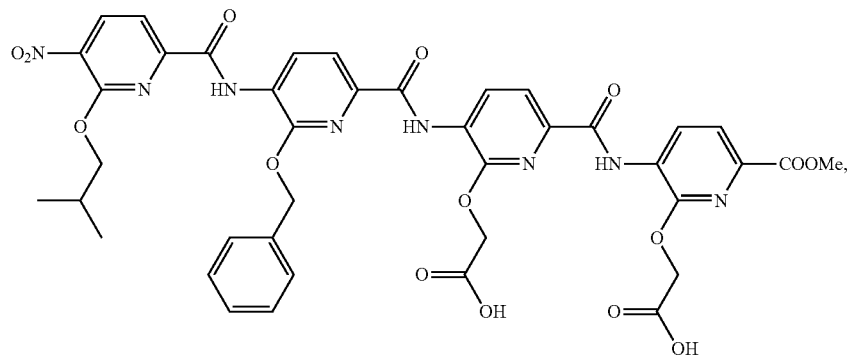 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

In some embodiments of any of the above treatment methods, the compound has the structure according to the following formula:

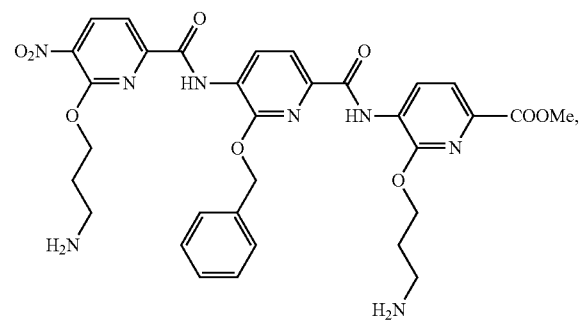 [SMILES: COC(=O)c1ccc(NC(=O)c2ccc(NC(=O)c3ccc([N+](=O)[O-])c(OCCCN)n3)c(OCc3ccccc3)n2)c(OCCCN)n1]

or a pharmaceutically acceptable salt thereof.

In some embodiments of any of the above treatment methods, the compound has the structure according to the following formula:

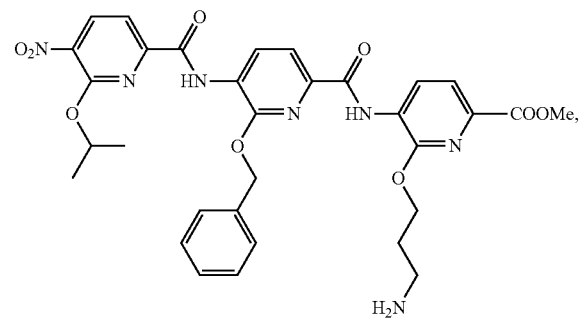 [SMILES: COC(=O)c1ccc(NC(=O)c2ccc(NC(=O)c3ccc([N+](=O)[O-])c(OC(C)C)n3)c(OCc3ccccc3)n2)c(OCCCN)n1]

or a pharmaceutically acceptable salt thereof.

In some embodiments of any of the above treatment methods, the compound has the structure according to the following formula:

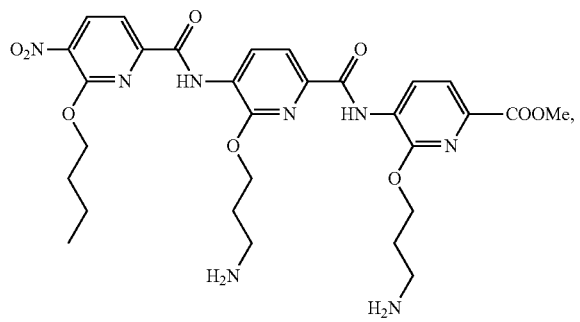 [SMILES: CCCCOc1nc(C(=O)Nc2ccc(C(=O)Nc3ccc(C(=O)OC)nc3OCCCN)nc2OCCCN)ccc1[N+](=O)[O-]]

or a pharmaceutically acceptable salt thereof.

In some embodiments of any of the above treatment methods, the compound has the structure according to the following formula:

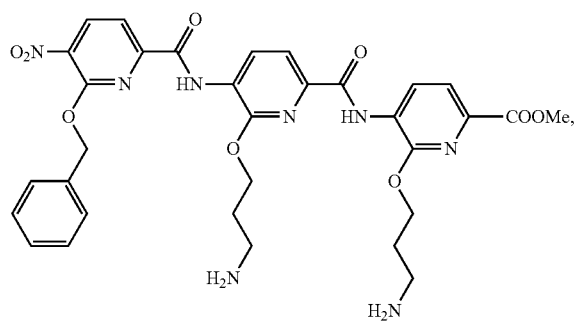 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

In some embodiments of any of the above treatment methods, the compound has the structure according to the following formula:

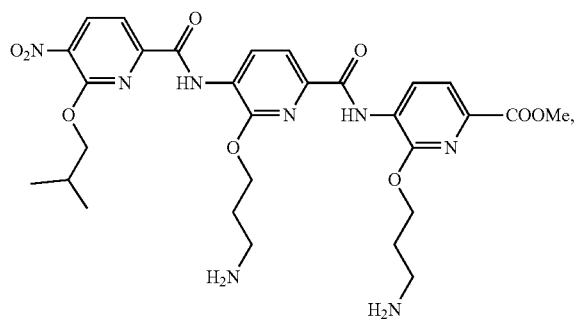 [SMILES: COC(=O)c1ccc(NC(=O)c2ccc(NC(=O)c3ccc([N+](=O)[O-])c(OCC(C)C)n3)c(OCCCN)n2)c(OCCCN)n1]

or a pharmaceutically acceptable salt thereof.

In another aspect, a method of treating a disease in a subject in need of such treatment is provided, wherein the disease is associated with one or more p53 mutations, comprising administering to said subject an effective amount of a compound of formula (I):

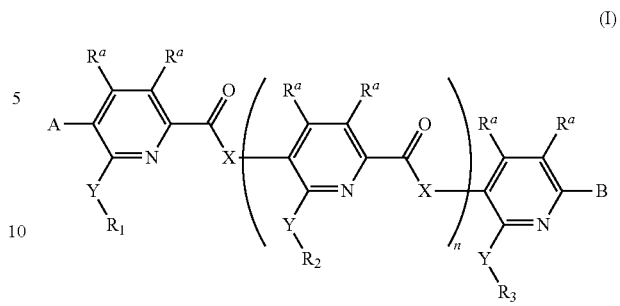

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and —C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_3$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

A is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl;

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl;

R* is independently selected at each occurrence from hydrogen or C$_1$-C$_{12}$ hydrocarbons each of which optionally contains 1-8 heteroatoms selected from halogen, O, N, and S and combinations thereof; and n is an integer from 0 to 2;

or a pharmaceutically acceptable salt thereof.

In some embodiments of any of the above treatment methods, (i) when n is 0, and Y is O, R$_1$ and R$_3$ are not both —CH$_2$CO$_2$H; (ii) when n is 1, Y is O, and R$_1$ and R$_3$ are both —CH$_2$CO$_2$H, R$_2$ is not —CH$_2$CO$_2$H or a straight chained, branched or cyclic aliphatic or aryl C$_1$-C$_{12}$ hydrocarbon, or R$_2$ does not have the structure —C(CH$_2$CO$_2$H)$_3$; (iii) when n is 1, and Y is O, R$_1$ through R$_3$ are not each an unsubstituted C$_1$-C$_8$ hydrocarbon; and (iv) when n is 2, and Y is O, R$_1$ through R$_3$ are not —CH$_2$CO$_2$H at all occurrences, In some embodiments of any of the above treatment methods, the disease is a cancer.

In some embodiments of any of the above treatment methods, the disease is associated with aggregation of a p53 protein.

In some embodiments of any of the above treatment methods, the effective amount inhibits aggregation of the p53 protein.

In some embodiments of any of the above treatment methods, the one or more p53 mutations comprise R248W mutation.

In some embodiments of any of the above treatment methods, the subject is human.

In some embodiments, the compound has the structure according to formula (II):

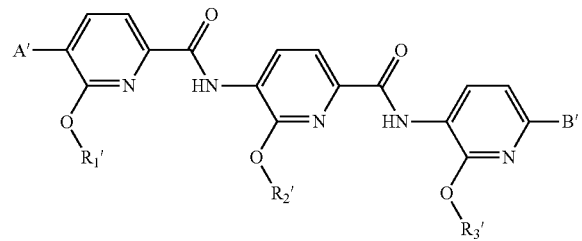

(II)

wherein R$_1$' is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof;

R$_2$' is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof;

R$_3$' is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof;

A' is selected from —NO$_2$; —NH$_2$; —NHR*; —N(R*)—(C=O)—R*, —N(R*)$_2$, where R* is hydrogen or an aliphatic C$_1$-C$_{12}$ hydrocarbon; and B' is selected from —(C=O)—R*; —CO₂H; —CO₂R*, where R* is hydrogen or an aliphatic $C_1$-$C_{12}$ hydrocarbon;

R* is independently selected at each occurrence from hydrogen or $C_1$-$C_{12}$ hydrocarbons each of which optionally contains 1-8 heteroatoms selected from halogen, O, N, and S and combinations thereof;

or a pharmaceutically acceptable salt thereof.

In some embodiments of any of the above treatment methods, (i) when $R_1$ and $R_3$ are both —CH₂CO₂H, $R_2$ is not —CH₂CO₂H or a straight chained, branched or cyclic aliphatic $C_1$-$C_{12}$ hydrocarbon, or $R_2$ does not have the structure —C[CH₂CO₂H]₃; and (ii) $R_1$ through $R_3$ are not each an unsubstituted $C_1$-$C_8$ hydrocarbon.

In some embodiments of any of the above treatment methods, the compound has the structure according to the following formula:

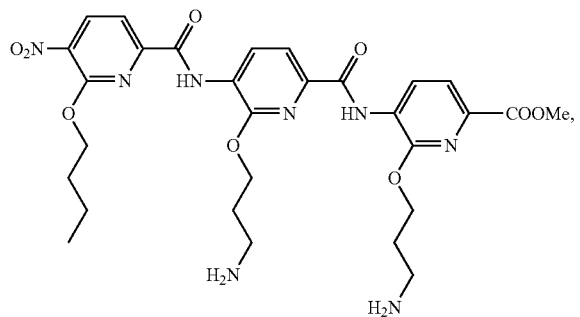 [SMILES: CCCCOc1nc(C(=O)Nc2ccc(C(=O)Nc3ccc(C(=O)OC)nc3OCCCN)nc2OCCCN)ccc1[N+](=O)[O-]]

or a pharmaceutically acceptable salt thereof.

In some embodiments of any of the above treatment methods, the compound has the structure according to the following formula:

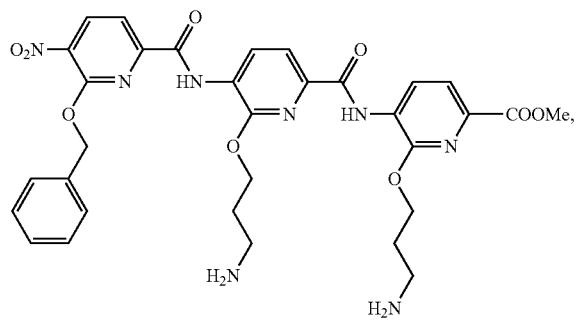 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

In some embodiments of any of the above treatment methods, the compound has the structure according to the following formula:

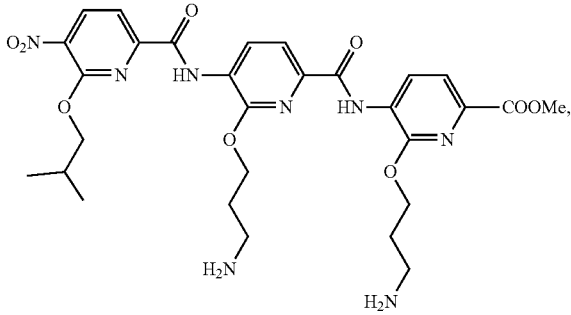 [SMILES: COC(=O)c1ccc(NC(=O)c2ccc(NC(=O)c3ccc([N+](=O)[O-])c(OCC(C)C)n3)c(OCCCN)n2)c(OCCCN)n1]

or a pharmaceutically acceptable salt thereof.

In one aspect, the invention provides a method of inhibiting aggregation of a p53 protein comprising contacting said p53 protein with an effective amount of any of the compounds described above (or a combination of two or more such compounds).

In one embodiment, the p53 protein comprises one or more mutations (e.g., amino acid substitutions, deletions, additions, or any combinations thereof). In one embodiment, the one or more p53 mutations are associated with p53 protein aggregation. In one embodiment, the one or more p53 mutations comprise R248W mutation. In one embodiment, the one or more p53 mutations comprise mutations in positions (amino acid residues) 175, 220, 245, 248, 273, and/or 282. In one embodiment, the one or more p53 mutations comprise mutations in p53 regions corresponding to positions (amino acid residues) 130-136, 140-148, 230-236, and/or 251-257.

In one embodiment, the p53 protein is in a cell. In one embodiment, the cell is in a subject.

In another aspect, the invention provides a method of treating a disease in a subject in need of such treatment, wherein the disease is associated with one or more p53 mutations (e.g., amino acid substitutions, deletions, additions, or any combinations thereof), said method comprising administering to said subject an effective amount of any of the compounds described above (or a combination of two or more such compounds).

In one embodiment of any of the above treatment methods, the one or more p53 mutations are associated with p53 protein aggregation.

In one embodiment of any of the above treatment methods, the one or more p53 mutations comprise R248W mutation.

In one embodiment of any of the above treatment methods, the one or more p53 mutations comprise mutations in positions (amino acid residues) 175, 220, 245, 248, 273, and/or 282.

In one embodiment of any of the above treatment methods, the one or more p53 mutations comprise mutations in p53 regions corresponding to positions (amino acid residues) 130-136, 140-148, 230-236, and/or 251-257.

In one embodiment of any of the above treatment methods, the disease is a cancer. Non-limiting examples of cancers include, e.g., non-small cell lung cancer (NSCLC), acute myelogenous leukemia (AML), astrocytoma, breast carcinoma, Burkitt lymphoma, colorectal adenoma, colorectal carcinoma, esophageal squamous cell carcinoma, gastric carcinoma, glioblastoma, head and neck squamous cell carcinoma, melanoma, NK-leukemia, pancreatic cancer, prostate cancer, and rhabdomyosarcoma.

For additional non-limiting examples of p53 mutations and cancers see, e.g., p53 database available at http://p53.free.fr/Database/p53_database_distr.html as well as Soussi T., Handbook of p53 mutation in cell lines, 2010 and http://p53.free.fr/.

In one embodiment of any of the above methods, the subject is human.

These and other aspects of the present invention will be apparent to those of ordinary skill in the art in the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows TEM images of p53 R248W peptide aggregates after a 24 hr incubation period in distilled water at 37° C. at 50 µM. Corresponding structures found in Aβ samples prepared using an analogous protocol are shown for reference. FIG. 3B TEM also captured large, clustered amyloid-like fibrils resulting from R248W peptide aggregation under the aforementioned conditions.

FIG. 4A depicts treating 50 µM R248W with inhibitor peptides I254R and PAS-I254R at 2:1 and 1:1 ratios at 37° C. FIG. 4B depicts treating R248W at a 1:1 ratio with inhibitor peptide G3-ReACp53 at 37° C. and comparing with I254R and PAS-I254R inhibition propensity.

FIG. 6A shows examples of structures of ADH compounds found to inhibit aggregation. FIG. 6B shows treating R248W at a 1:1 ratio with ADH compounds at 37° C. for 10 hours. Abrogation of aggregation is indicated by lower levels of fluorescence and delayed aggregation nucleation. ADH-41 was found to be the most effective inhibitor of R248W aggregation, as well as Aβ amyloid formation.

FIG. 7A shows MIA PaCa-2 cells incubated with the respective peptide (5 and 10 µM) for 24 and 48 hours in serum-free media. G3-ReACp53 and ReACp53 have approximately the same level of toxicity upon introduction to the same the cell line (n=3). Cell viability was measured using MTS. FIG. 7B shows MIA PaCa-2 cells treated with higher concentrations of PAS-I254R to confirm its ineffectiveness at inducing toxicity in p53 R248W mutant cell line. Cells were treated with the peptide and incubated in either serum-supplemented or serum-free medium for 24 hours (n=3).

FIG. 8A shows MIA PaCa-2 cells incubated with labeled inhibitors 1-6 hrs prior to imaging (see Example 1). All peptides are internalized by the cells. FIG. 8B shows cells treated with labeled PAS-I254R and G3-ReACp53 were immunostained for p53 and imaged using inverted confocal microscopy. Co-localization is seen in G3-ReACp53 treated cells but not with PAS-I254R.

FIG. 9A show cell viability plots for MIA PaCa-2 cells incubated with the respective ADH compound according to the invention (17, 27, 31, 37, 39, 40, 41, 45, 46, and 52) for 24 and 48 hours in serum-free media. ADH-40, 41 and 46 showed highly significant toxicity upon treatment. ADH-40 shows the highest level of toxicity (>90%) of all compounds and peptides tested. Cell viability was measured using MTS (n=3). FIG. 9B shows ADH compounds administered to N2a cells at 5 µM and incubated for 24 hours. The compounds had no effect on cell viability.

Figure 1:
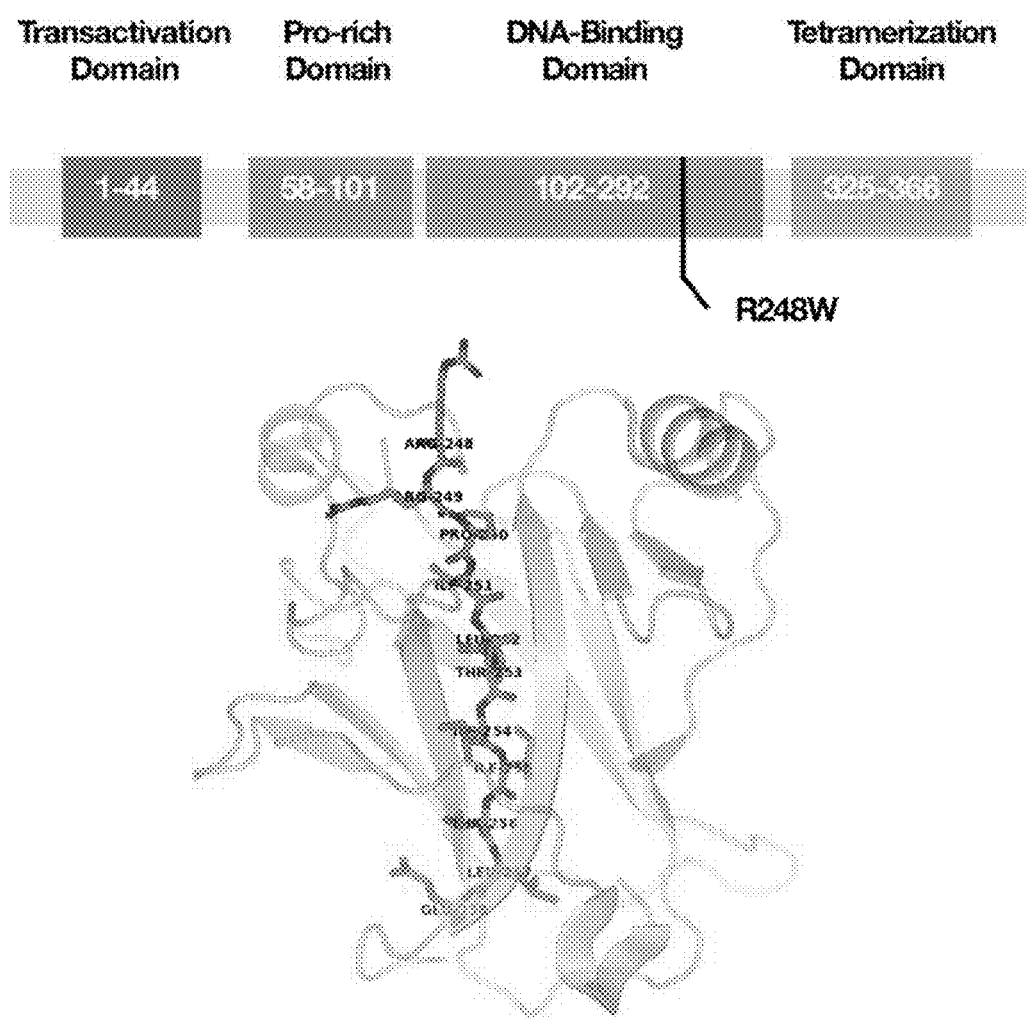
FIG. 1 depicts a schematic representation of the Hotspot Mutation R248W located within aggregation-prone segment of the DNA-binding domain of p53 (identified by Tango). The arginine residue known to be crucial for DNA-binding is highlighted.

Significant toxicity was observed with compounds 40, 41 and 46. Cell viability was measured using the MTS assay (n=3).

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

The present invention is based on the surprising discovery by the present inventors that amyloid-like aggregated formed by a p53 contact mutant (R248W) can be targeted using amyloid inhibitor ADH compounds. ADH compounds are tripyridylamide-based alpha-helix mimetics that have been shown by the present inventors to bind to Aβ and inhibit amyloid formation (see U.S. 2018/0170910, the contents of which are incorporated by reference herein in their entirety). In the present invention, aggregation of R248W p53 protein mutant was found to be inhibited by a select number of these compounds at an equimolar ratio. Especially suitable compounds are ADH 31, 37, 39, 40, 41 and 46. ADH 40, 41 and 46 also induce significant toxicity in MIA PaCa-2 cells that harbor the p53 R248W mutation, indicating that mutant p53 function can be rescued by targeting p53 aggregation, thus enabling the induction of apoptosis. Additionally, it was found that the ADH compounds exhibit no toxicity in the wild-type p53 cell line N2a.

As demonstrated in the Examples section, below, ADH 40, 41 and 46 compounds can potentially serve as viable and potent cancer therapeutics. Using a multi-step Thioflavin T (ThT) assay, it is shown that ADH-40, 41 and 46 can abrogate R248W aggregates past the elongation phase of amyloid formation, supporting the hypothesis that these compounds can effectively target pre-formed p53 aggregates in the cell. The ADH compounds also induce no significant toxicity in other wild-type p53 cells lines (MCF-7 and COS-7), indicating that they likely target pathways in the cell that result in p53 dysfunction. Interestingly, HeLa cells exhibit marked toxicity when treated with ADH compounds, which may indicate that the compounds can be used to target cancer pathways beyond those that result from mutant p53 aggregation, including other manifestations of compromised p53 function.

Definitions

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "oligomerization", as it relates to peptides in general and p53 in particular, refers to a chemical process that converts individual peptide molecules into a chain consisting of a finite number of the peptide molecules. These chains are referred to as "oligomers", and they are typically soluble.

The term "aggregation", as it relates to peptides in general and p53 in particular, refers to a process of conversion of soluble peptide oligomers into non-specific insoluble material. Under certain conditions amyloidogenic peptide oligomers aggregate into fibrils, a process referred to as fibrillation.

The term "fibrillation", as it relates to peptides, refers to a process of forming fibrils. As stated above, the soluble oligomers of amyloidogenic peptides undergo the process of fibrillation, where they combine into insoluble fibrils.

The term "modulating aggregation" or "modulating fibrillation" may refer to promoting, or agonizing, or, alternatively, inhibiting, or antagonizing, the formation of oligomers and/or fibers of a protein or a peptide.

The term "altering the structure" of a protein or a peptide refers to changing, modifying, adjusting, shifting, transforming, or causing to change, modify, adjust, shift, or transform the structural conformation of a protein or a peptide, including secondary or tertiary structure of a protein or a peptide.

The term "dipyridylamide" refers to a compound having two pyridyl rings connected via an amide (—(C=O)—NH—) bond. The term "tripyridylamide" refers to a compound having three pyridyl rings connected via amide bonds. The term "tetrapyridylamide" refers to a compound having four pyridyl rings connected via amide bonds. The term "oligopyridylamide" refers to any of the above compounds having from two to four pyridyl rings connected via amide bonds.

p53 Aggregation p53 mutants are among the most common mutations in cancer, with more than 95% of mutations occurring in the DNA-binding domain. p53 aggregation is a thermodynamically favorable process whereby destabilization of the protein, brought about by DNA-binding mutations, results in the exposure of an aggregation-nucleating region of the protein. This exposed segment has the propensity to associate with similar sequences among the p53 family, including mutant and wild-type forms of p53, resulting in aggregation and structural transition to amyloid fibers. Here it is shown that p53 contact mutant R248W aggregates into amyloid structures, which serves as the basis for the loss-of-function and gain-of-oncogenic function of the mutant p53 phenotype. Wild-type p53 becomes incorporated in cellular aggregates seeded by mutant p53, thereby sequestering its inherent tumor suppressor function. Essentially, these cellular aggregates operate as a wild-type p53 sink that reduces the overall concentration of functioning p53 in the cell, promoting uncontrolled cell division and tumor metastasis.

Thioflavin T assay data and TEM images of R248W aggregates support the hypothesis that mutant p53 undergoes amyloid formation. Importantly, the efficacy of ADH compounds at inhibiting mutant p53 aggregation and inducing cell death/apoptosis in a p53 contact mutant (R248W) cell line demonstrates the first successful use of bona fide amyloid inhibitors as cancer therapeutics, which further establishes mutant p53 aggregates as amyloid in nature. It is shown that mutant p53 gain-of-oncogenic function can be overcome by sequence-specific inhibition, as in the case of ReACp53 and G3-ReACp53, as well as structure-specific inhibition, as in the case of the ADH alpha-helix mimetics (amyloid inhibitors). The MIA PaCa-2 cell line, which contains both R248W and WT p53, is shown to be a viable model for these inhibition strategies. The non-toxicity seen with the N2a cell line acts a proof of principle approach, since the cells contain WT p53 as opposed to its aggregation-prone mutant form. Thus, a new targeted therapeutic strategy has been established for mutant p53 cancers, many of which, including pancreatic carcinoma, do not currently have effective treatment options.

Key traits of the inhibitors that were found to be effective at inducing cytotoxicity were cell-penetrating ability, an ability to target a particular domain of mutant p53 and an overall charged nature. The exceptions to this rule were I254R and PAS-I254R, which seem, from these experiments, to harbor each of these characteristics. It is possible that the overall charge:residue ratio of these peptides is too low to overcome hydrophobic interactions and protein aggregation forces. The I254R and its PASylated derivative have lower ratios when compared to the G3-ReACp53 and ReACp53 peptides (as well as the effective ADH compounds) even though they both contain elongated sequences of the DBD region, which were hypothesized to enhance specificity and inhibition function. Hence, it can be deduced that the LTRITLE sequence is enough to target and bind the region. The intended cell-penetrating effect of the oligoarginine tag is likely not its sole function in the peptide. Not only does this sequence allow the peptide to enter the cell more efficiently, it also greatly enhances the charged repulsion effect of the peptide after sequence-specific binding. By the same token, the PAS sequence of the I245R might impede the peptide's ability to bind to pre-formed p53 aggregates, as well as its ability to introduce hydrostatic interactions that force formed aggregates apart. Thus, these peptides are ineffective when introduced into the cell.

The potency of the ADH-40 compound in its induction of cell death in a p53 mutant cell line is an interesting phenomenon that has yet to be fully investigated in the scope of this project. Despite not have a specific sequence that targets p53 mutants, as the ReACp53 and G3 derivative peptides do, the mimetic appears to interact with the mutant peptide amyloid structures in the cell and inhibit aggregation. It has been hypothesized that ADH-40 targets p53 aggregates within the cell and rescues p53 function. An explanation as to why ADH-40, a compound that was developed to inhibit Aβ fibrillation, seems to work as a more effective cancer therapeutic when compared to peptides that were designed with p53 aggregation inhibition in mind, such as ReACp53 or G3-ReACp53, may lie in its structure-specific binding. A recent study proposed that p53 aggregation occurs at several domains of the p53 protein. This means that while sequence-specific inhibition may effectively target one domain prone to aggregation, other domains are free to seed further aggregation of mutant p53. Thus, targeting a ubiquitous intermediate structure during amyloid formation may prove to be more effective, as demonstrated by ADH-40. The compound may inhibit amyloid formation at multiple aggregation prone regions of the protein, effectively targeting and obstructing other pathways that favor mutant p53 aggregation. Moreover, when compared to the ADH-41 compound, which was the most effective at inhibiting aggregation in our ThT model, ADH-40 is overall less hydrophobic, with one less aromatic functional residue when compared to ADH-41. Thus, while ADH 40's overall greater cytotoxic effect could be matter of its ability to target other aggregating domains of the mutant p53 protein, its efficacy in inducing cell toxicity could also be attributed to its enhanced ability to enter the cell.

Several experiments could be implemented to understand this phenomenon, such as testing ADH-40's efficacy at inhibiting elongated mutant p53 structures, as well as comparing binding energies of mutant p53 complexes with structure and inhibitors using isothermal calorimetry. Visualizing ADH-40 co-localization with mutant p53 aggregates in the cell would also serve as a key step in the delineation of the compound's interaction with target p53 aggregates, just as was done for the I254R, PAS-I254R and G3-ReACp53 in this project. Moreover, understanding possible off-target interactions mediated by ADH-40, as well as the ReACp53 and G3-ReACp53, will be important in the elucidation of their function in cancer cells and necessary in the advancement of this compound as a cancer therapeutic.

This study aims to bridge two important and exceptionally active fields in biological research: cancer and amyloid disease. As demonstrated throughout this project, therapeutic approaches aimed at treating amyloidosis may become novel and viable treatments strategies for cancer. Future studies related to this project may involve the repurposing of amyloid drugs to treat mutant p53 cancers, or testing the efficacy of the ADH-compounds in comparison to ReACp53 derivates in other p53 mutant forms, such as R175H. The field of p53 aggregation and its treatment as amyloid in nature has gained significant traction in the past few years.

Methods of Inhibiting p53 Aggregation

In one aspect, compounds and/or pharmaceutical compositions of the invention may be used for inhibiting aggregation of a protein or peptide, e.g., inhibiting aggregation of tumor protein p53, also known as p53, cellular tumor antigen p53, phosphoprotein p53, tumor suppressor p53, or transformation-related protein 53 (TRP53).

In some embodiments, compounds and/or pharmaceutical compositions according to the invention may be useful for inhibiting aggregation of p53.

In one implementation, the compounds for use in the methods of the invention have the structure of formula (I):

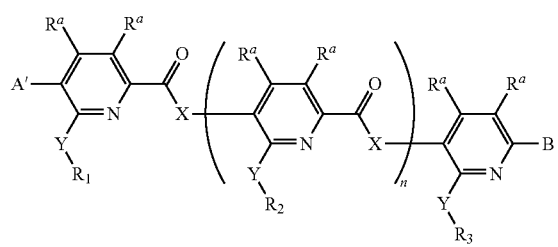

(I)

and pharmaceutically acceptable salts thereof.

In formula (I), $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$.

In some embodiments, $R^a$ is present at 0, 1, or 2 different positions on the ring.

In some embodiments, $R^a$ is hydrogen at all occurrences.

X is independently at each occurrence selected from —O—; —S—; —NH—; —NR*—; and —C(R*)$_2$.

In some embodiments X is —NH— or —NR*—, such that —(C=O)—X— is an amide bond, at all occurrences. In some embodiments X is NH—.

In some embodiments X is not —O—. In some embodiments X is not —S—. In some embodiments X is not C(R*)$_2$.

Y is independently at each occurrence selected from —O—; —S—; —NH—; and —NR*—.

In some embodiments Y is —O— at all occurrences.

In some embodiments Y is not —S—. In some embodiments Y is not —NH— or —NR*—.

$R_1$, $R_2$, and/or $R_3$ are independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof.

In some embodiments $R_1$, $R_2$, and/or $R_3$ are independently at each occurrence selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof.

In some embodiments $R_1$, $R_2$, and/or $R_3$ are independently at each occurrence a straight chained, branched or cyclic aliphatic $C_1$-$C_{20}$ hydrocarbon, optionally substituted with one or more of —NH$_2$; —NHR*; —N(R*)$_2$; —N(R*)$_3^+$; —(C=O)—R*; —CO$_2$H; or —CO$_2$R*; and combinations thereof.

In some embodiments $R_1$, $R_2$, and/or $R_3$ are independently at each occurrence a straight chained, branched or cyclic $C_1$-$C_{20}$ hydrocarbon, optionally substituted with one or more of —NH$_2$; —NHR*; —N(R*)$_2$.

In some embodiments $R_1$, $R_2$, and/or $R_3$ are independently at each occurrence a straight chained, branched or cyclic aliphatic $C_1$-$C_{20}$ hydrocarbon, optionally substituted with —CO$_2$H. In some embodiments $R_1$, $R_2$, and/or $R_3$ may independently at each occurrence be —CH$_2$CO$_2$H.

In some embodiments $R_1$, $R_2$, and/or $R_3$ at all occurrences do not contain —CO$_2$H. In some embodiments $R_1$, $R_2$, and/or $R_3$ are not —CH$_2$CO$_2$H at all occurrences.

In some embodiments $R_1$, $R_2$, and/or $R_3$ are independently at each occurrence selected from an aromatic $C_6$-$C_{20}$ hydrocarbon; a heteroaromatic $C_1$-$C_{20}$ hydrocarbon; an aryl $C_6$-$C_{20}$ hydrocarbon; or a heteroaryl $C_1$-$C_{20}$ hydrocarbon optionally containing 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*.

In some embodiments, $R_1$, $R_2$, and/or $R_3$ are independently at each occurrence selected from a substituted or unsubstituted phenyl, benzyl, naphthyl, indolyl, pyrrolidinyl, pyrrolyl, imidazolyl, pyrazolyl, oxazolyl, isoxazolyl, thiazolyl, isothiazolyl, histidinyl (i.e., —CH$_2$-imidazole), triazolyl, pyridyl, pyranyl, diazinyl, oxazinyl, thiazinyl, or triazinyl.

In some embodiments, A and B are independently selected from hydrogen, —F; —Cl; —Br; —I; —OH, —OR*; —NO; —NO$_2$; —NO$_3$; —O—NO; —N$_3$; —NH$_2$;

—NHR*; —N(R*)$_2$; —N(R*)$_3$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl.

In some embodiments A is selected from —NO$_2$; —NH$_2$; —NHR*; —N(R*)—(C=O)—R*, —N(R*)$_2$. In some embodiments A is —NO$_2$. In some embodiments A is NH$_2$; —NHR*; or —N(R*)$_2$.

In some embodiments A is not —N(R*)—(C=O)—R*. In some embodiments A is not NH$_2$; —NHR*; or —N(R*)$_2$.

In some embodiments B is selected from —(C=O)—R*; —CO$_2$H; —CO$_2$R*. In some embodiments B may be —CO$_2$R*, where R* is a $C_1$-$C_{12}$ hydrocarbon. In some embodiments B is —CO$_2$R* and R* is selected from methyl, ethyl, propyl, or butyl groups. In some embodiments A is —CO$_2$R* and R* is methyl.

In some embodiments B is not —CO$_2$H. In some embodiments B is not —(C=O)—R*.

In some embodiments R* is independently selected at each occurrence from hydrogen or $C_1$-$C_{12}$ hydrocarbons each of which optionally contains 1-8 heteroatoms selected from halogen, O, N, and S and combinations thereof.

In some embodiments n is an integer from 0 to 2.

In some embodiments, n is 0, i.e., the compound of formula (I) is a dipyridyl. In other embodiments n is 1, i.e., the compound of formula (I) is a tripyridyl. In yet other embodiments, n is 2, i.e., the compound of formula (I) may be a tetrapyridyl.

In some embodiments, n is 0, and X is —NH—, i.e., the compound of formula (I) is a dipyridylamide. In other embodiments n is 1, and X is —NH—, i.e., the compound of formula (I) is a tripyridylamide. In yet other embodiments, n is 2, and X is —NH—, i.e., the compound of formula (I) is a tetrapyridylamide.

In some embodiments, when n is 0, and Y is O, $R_1$ and $R_3$ are not both —CH$_2$CO$_2$H.

In some embodiments, when n is 1, Y is O, and $R_1$ and $R_3$ are both —CH$_2$CO$_2$H, R2 is not —CH$_2$CO$_2$H or a straight chained, branched or cyclic aliphatic or aryl $C_1$-$C_{12}$ hydrocarbon, or $R_2$ does not have the structure —C(CH$_2$CO$_2$H)$_3$.

In some embodiments, when n is 1, and Y is O, $R_1$ through $R_3$ are not each an unsubstituted $C_1$-$C_8$ hydrocarbon.

In some embodiments, when n is 2, and Y is O, $R_1$ through $R_3$ are not —CH$_2$CO$_2$H at all occurrences.

In one aspect, the compounds for use in the methods of the invention have the structure according to formula (II):

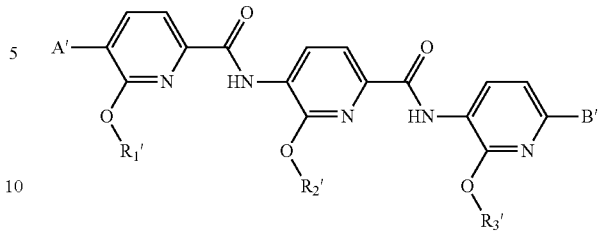

(II)

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof;

$R_2'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof;

A' is selected from —NO$_2$; —NH$_2$; —NHR*; —N(R*)—(C=O)—R*, —N(R*)$_2$, where R* is hydrogen or an aliphatic $C_1$-$C_{12}$ hydrocarbon; and B' is selected from —(C=O)—R*; —CO$_2$H; —CO$_2$R*, where R* is hydrogen or an aliphatic $C_1$-$C_{12}$ hydrocarbon;

R* is independently selected at each occurrence from hydrogen or $C_1$-$C_{12}$ hydrocarbons each of which optionally contains 1-8 heteroatoms selected from halogen, O, N, and S and combinations thereof;

or a pharmaceutically acceptable salt thereof.

In some embodiments, (i) when $R_1$ and $R_3$ are both —CH$_2$CO$_2$H, $R_2$ is not —CH$_2$CO$_2$H or a straight chained, branched or cyclic aliphatic $C_1$-$C_{12}$ hydrocarbon, or $R_2$ does not have the structure —C[CH$_2$CO$_2$H]$_3$; and (ii) $R_1$ through $R_3$ are not each an unsubstituted $C_1$-$C_8$ hydrocarbon.

In one embodiment, the compound has the structure according to the following formula:

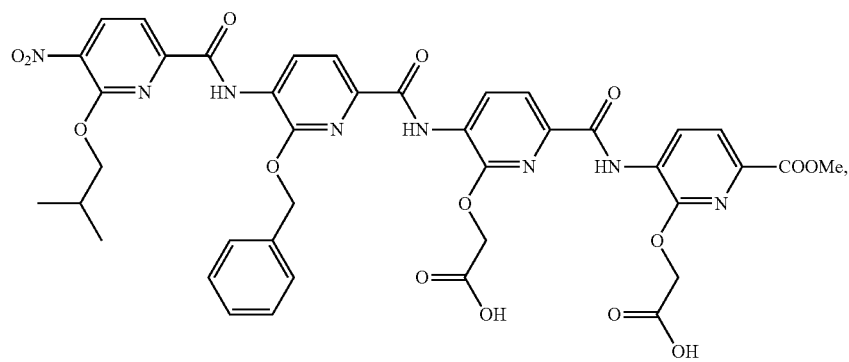 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

In one embodiment, the compound has the structure according to the following formula:

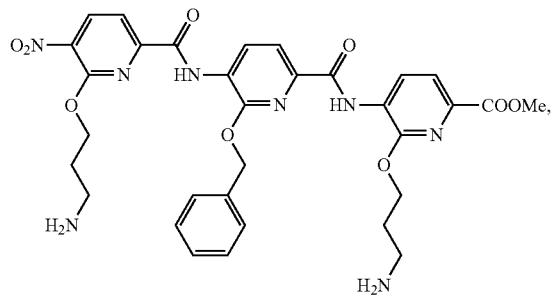 [SMILES: COC(=O)c1ccc(NC(=O)c2ccc(NC(=O)c3ccc([N+](=O)[O-])c(OCCCN)n3)c(OCc3ccccc3)n2)c(OCCCN)n1]

or a pharmaceutically acceptable salt thereof.

In one embodiment, the compound has the structure according to the following formula:

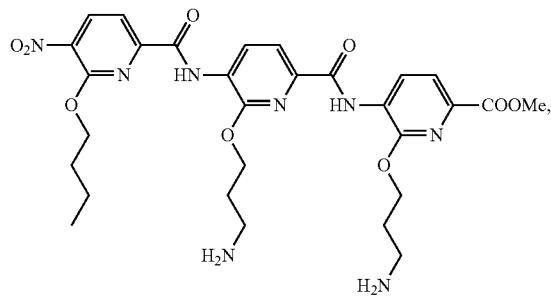 [SMILES: CCCCOc1nc(C(=O)Nc2ccc(C(=O)Nc3ccc(C(=O)OC)nc3OCCCN)nc2OCCCN)ccc1[N+](=O)[O-]]

or a pharmaceutically acceptable salt thereof.

In one embodiment, the compound has the structure according to the following formula:

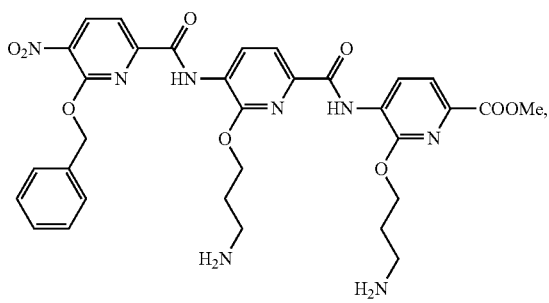 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

In one embodiment, the compound has the structure according to the following formula:

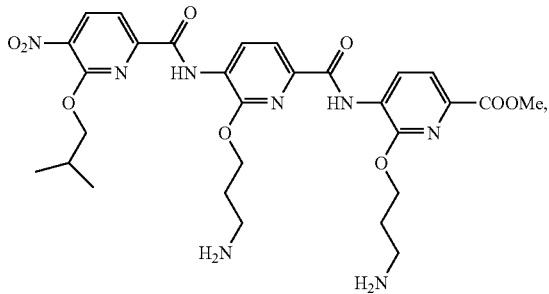 [SMILES: COC(=O)c1ccc(NC(=O)c2ccc(NC(=O)c3ccc([N+](=O)[O-])c(OCC(C)C)n3)c(OCCCN)n2)c(OCCCN)n1]

or a pharmaceutically acceptable salt thereof.

In conjunction with the compounds of the invention, the invention also provides methods of using these compounds.

In one aspect, a method of inhibiting aggregation of a p53 protein is provided comprising contacting said p53 protein with an effective amount of a compound of formula (I):

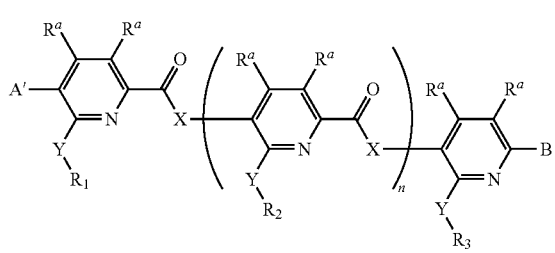

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and —C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_3$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

A is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl;

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl;

R* is independently selected at each occurrence from hydrogen or $C_1$-$C_{12}$ hydrocarbons each of which optionally contains 1-8 heteroatoms selected from halogen, O, N, and S and combinations thereof; and n is an integer from 0 to 2;

or a pharmaceutically acceptable salt thereof.

In some embodiments, (i) when n is 0, and Y is O, $R_1$ and $R_3$ are not both —CH$_2$CO$_2$H; (ii) when n is 1, Y is O, and $R_1$ and $R_3$ are both —CH$_2$CO$_2$H, $R_2$ is not —CH$_2$CO$_2$H or a straight chained, branched or cyclic aliphatic or aryl $C_1$-$C_{12}$ hydrocarbon, or $R_2$ does not have the structure —C(CH$_2$CO$_2$H)$_3$; (iii) when n is 1, and Y is O, $R_1$ through $R_3$ are not each an unsubstituted $C_1$-$C_8$ hydrocarbon; and (iv) when n is 2, and Y is O, $R_1$ through $R_3$ are not —CH$_2$CO$_2$H at all occurrences.

In one embodiment of the above method, the p53 protein comprises one or more mutations.

In one embodiment of the above method, the p53 protein comprises one or more mutations at amino acid locations selected from R175, G245, R248, R249, 1254, R273, and R282. In one embodiment of the above method, the p53 protein comprises one or more mutations selected from R248W, R248Q, and I254R.

In one embodiment, the p53 protein comprises R248W mutation.

In one embodiment, the p53 protein is in a cell.

In one embodiment, the cell is in a subject.

In one embodiment of the above method, the compound has the structure according to formula (II):

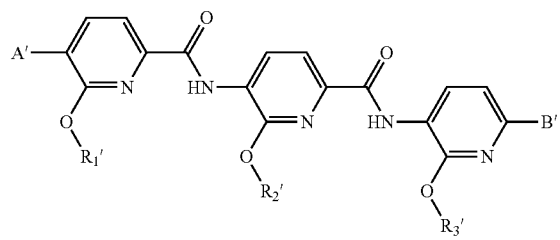

(II)

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3$; —(C=O)—$R^*$; —CHO; —$CO_2H$; —$CO_2R^*$; —(C=O)—S—$R^*$; —O—(C=O)—H; —O—(C=O)—$R^*$; and combinations thereof;

$R_2'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3$; —(C=O)—$R^*$; —CHO; —$CO_2H$; —$CO_2R^*$; —(C=O)—S—$R^*$; —O—(C=O)—H; —O—(C=O)—$R^*$; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —$NHR^*$; —$N(R^*)_2$; —$N(R^*)_3$; —(C=O)—$R^*$; —CHO; —$CO_2H$; —$CO_2R^*$; —(C=O)—S—$R^*$; —O—(C=O)—H; —O—(C=O)—$R^*$; and combinations thereof;

A' is selected from —$NO_2$; —$NH_2$; —$NHR^*$; —$N(R^*)$—(C=O)—$R^*$, —$N(R^*)_2$, where $R^*$ is hydrogen or an aliphatic $C_1$-$C_{12}$ hydrocarbon; and B' is selected from —(C=O)—$R^*$; —$CO_2H$; —$CO_2R^*$, where $R^*$ is hydrogen or an aliphatic $C_1$-$C_{12}$ hydrocarbon;

$R^*$ is independently selected at each occurrence from hydrogen or $C_1$-$C_{12}$ hydrocarbons each of which optionally contains 1-8 heteroatoms selected from halogen, O, N, and S and combinations thereof;

or a pharmaceutically acceptable salt thereof.

In one embodiment, (i) when $R_1$ and $R_3$ are both —$CH_2CO_2H$, $R_2$ is not —$CH_2CO_2H$ or a straight chained, branched or cyclic aliphatic $C_1$-$C_{12}$ hydrocarbon, or $R_2$ does not have the structure —$C[CH_2CO_2H]_3$; and (ii) $R_1$ through $R_3$ are not each an unsubstituted $C_1$-$C_8$ hydrocarbon.

In one embodiment of the above method, the compound has the structure according to the following formula:

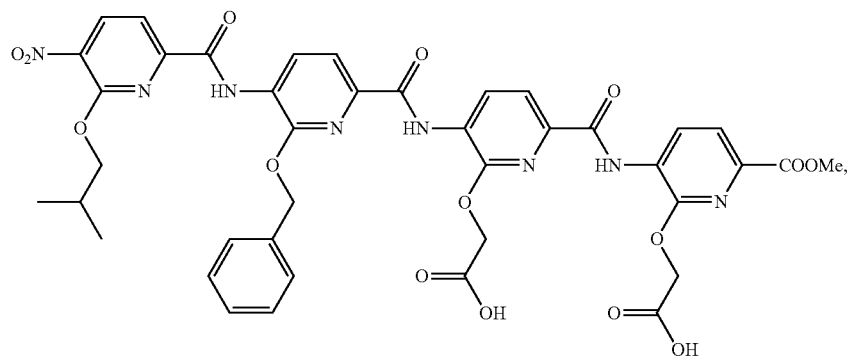 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

In one embodiment of the above method, the compound has the structure according to the following formula:

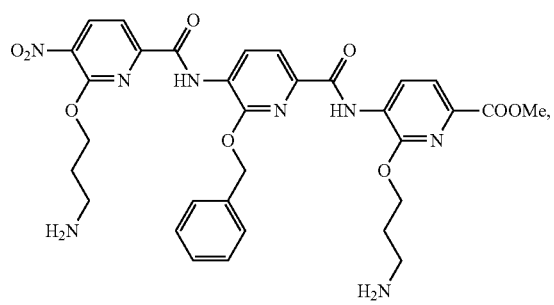 [SMILES: COC(=O)c1ccc(NC(=O)c2ccc(NC(=O)c3ccc([N+](=O)[O-])c(OCCCN)n3)c(OCc3ccccc3)n2)c(OCCCN)n1]

or a pharmaceutically acceptable salt thereof.

In one embodiment of the above method, the compound has the structure according to the following formula:

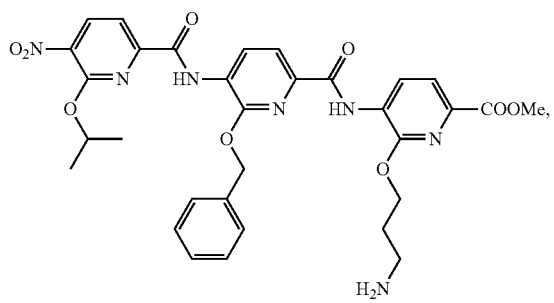 [SMILES: COC(=O)c1ccc(NC(=O)c2ccc(NC(=O)c3ccc([N+](=O)[O-])c(OC(C)C)n3)c(OCc3ccccc3)n2)c(OCCCN)n1]

or a pharmaceutically acceptable salt thereof.

In one embodiment of the above method, the compound has the structure according to the following formula:

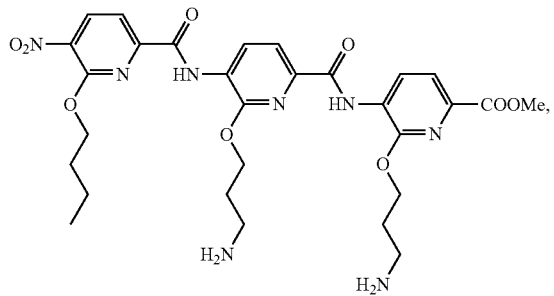 [SMILES: CCCCOc1nc(C(=O)Nc2ccc(C(=O)Nc3ccc(C(=O)OC)nc3OCCCN)nc2OCCCN)ccc1[N+](=O)[O-]]

or a pharmaceutically acceptable salt thereof.

In one embodiment of the above method, the compound has the structure according to the following formula:

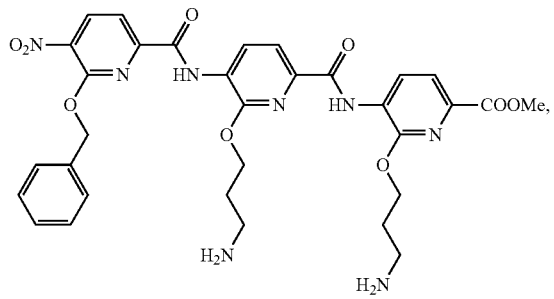 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

In one embodiment of the above method, the compound has the structure according to the following formula:

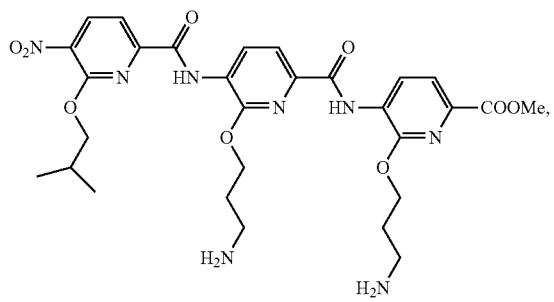 [SMILES: COC(=O)c1ccc(NC(=O)c2ccc(NC(=O)c3ccc([N+](=O)[O-])c(OCC(C)C)n3)c(OCCCN)n2)c(OCCCN)n1]

or a pharmaceutically acceptable salt thereof.

In another aspect, a method of treating a disease in a subject in need of such treatment is provided, wherein the disease is associated with or more p53 mutations, comprising administering to said subject an effective amount of a compound of formula (I):

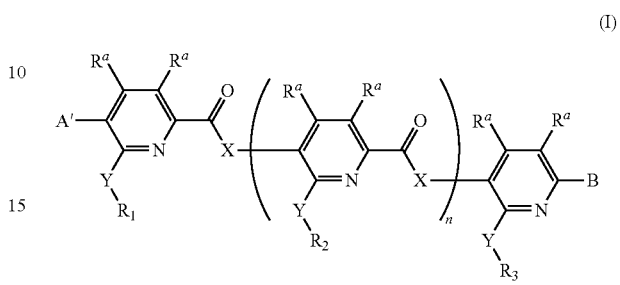

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and —C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$;

—O—CF₃; —P(R*)₂; —O—P(=O)(OR*)₂; —P(=O)(OR*)₂ and combinations thereof;

R₃ is selected from hydrogen or a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C₁₂ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂ and combinations thereof;

A is selected from hydrogen, —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂; C₁-C₈ perfluorocarbon; an aliphatic C₁-C₁₂ hydrocarbon; an aromatic C₁-C₁₂ hydrocarbon; and a C₁-C₁₂ heteroaryl;

B is selected from hydrogen, —F; —Cl; —Br; —I; —OH, —OR*; —NO; —NO₂; —NO₃; —O—NO; —N₃; —NH₂; —NHR*; —N(R*)₂; —N(R*)₃⁺; —N(R*)—OH; —O—N(R*)₂; —N(R*)—O—R*; —CN; —NC; —(C=O)—R*; —CHO; —CO₂H; —CO₂R*; —(C=O)—S—R*; —O—(C=O)—H; —O—(C=O)—R*; —S—(C=O)—R*; —(C=O)—NH₂; —(C=O)—N(R*)₂; —(C=O)—NHNH₂; —O—(C=O)—NHNH₂; —(C=S)—NH₂; —(C=S)—N(R*)₂; —N(R*)—CHO; —N(R*)—(C=O)—R*; —SCN; —NCS; —NSO; —SSR*; —SO₂R*; —SO₂—N(R*)₂; —S(=O)—OR*; —S(=O)—R*; —Si(R*)₃; —CF₃; —O—CF₃; —P(R*)₂; —O—P(=O)(OR*)₂; —P(=O)(OR*)₂; C₁-C₈ perfluorocarbon; an aliphatic C₁-C₁₂ hydrocarbon; an aromatic C₁-C₁₂ hydrocarbon; and a C₁-C₁₂ heteroaryl;

R* is independently selected at each occurrence from hydrogen or C₁-C₁₂ hydrocarbons each of which optionally contains 1-8 heteroatoms selected from halogen, O, N, and S and combinations thereof; and n is an integer from 0 to 2;

or a pharmaceutically acceptable salt thereof.

In some embodiments, (i) when n is 0, and Y is O, R₁ and R₃ are not both —CH₂CO₂H; (ii) when n is 1, Y is O, and R₁ and R₃ are both —CH₂CO₂H, R₂ is not —CH₂CO₂H or a straight chained, branched or cyclic aliphatic or aryl C₁-C₁₂ hydrocarbon, or R₂ does not have the structure —C(CH₂CO₂H)₃; (iii) when n is 1, and Y is O, R₁ through R₃ are not each an unsubstituted C₁-C₈ hydrocarbon; and (iv) when n is 2, and Y is O, R₁ through R₃ are not —CH₂CO₂H at all occurrences.

In some embodiments, the disease is a cancer.

In some embodiments, the disease is associated with aggregation of a p53 protein.

In one embodiment of the above method, the p53 protein comprises one or more mutations at amino acid locations selected from R175, G245, R248, R249, I254, R273, and R282. In one embodiment of the above method, the p53 protein comprises one or more mutations selected from R248W, R248Q, and I254R.

In some embodiments, the one or more p53 mutations comprise R248W mutation.

In some embodiments, the subject is human.

In one embodiment of the above method, the compound has the structure according to formula (II):

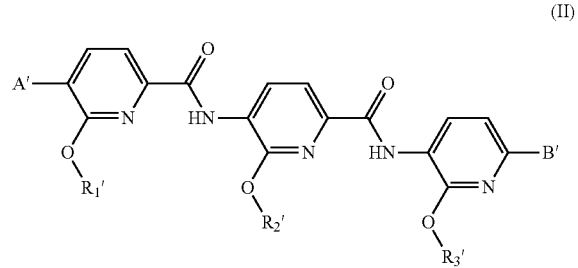

(II)

wherein R₁' is selected from a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C₁₂ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

R₂' is selected from a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C₁₂ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

R₃' is selected from a straight chained, branched or cyclic aliphatic C₁-C₂₀ hydrocarbon; an aromatic C₆-C₂₀ hydrocarbon; a heteroaromatic C₁-C₂₀ hydrocarbon; an aryl C₆-C₂₀ hydrocarbon; a heteroaryl C₁-C₂₀ hydrocarbon, a C₁-C₁₂ perfluorocarbon, or a combination thereof, each of which optionally contains 1-8 heteroatoms selected from halogen, O, N, and S, and each of which is optionally substituted with one or more of —NH₂; —NHR*; —N(R*)₂; —N(R*)₃⁺; —(C=O)—R*; —CHO; —CO₂H; —CO₂R*; —(C=O)—S—R*; —O—(C=O)—H; —O—(C=O)—R*; and combinations thereof;

A' is selected from —NO₂; —NH₂; —NHR*; —N(R*)—(C=O)—R*, —N(R*)₂, where R* is hydrogen or an aliphatic C₁-C₁₂ hydrocarbon; and B' is selected from —(C=O)—R*; —CO$_2$H; —CO$_2$R*, where R* is hydrogen or an aliphatic C$_1$-C$_{12}$ hydrocarbon;

R* is independently selected at each occurrence from hydrogen or C$_1$-C$_{12}$ hydrocarbons each of which optionally contains 1-8 heteroatoms selected from halogen, O, N, and S and combinations thereof;

or a pharmaceutically acceptable salt thereof.

In one embodiment, (i) when R$_1$ and R$_3$ are both —CH$_2$CO$_2$H, R$_2$ is not —CH$_2$CO$_2$H or a straight chained, branched or cyclic aliphatic C$_1$-C$_{12}$ hydrocarbon, or R$_2$ does not have the structure —C[CH$_2$CO$_2$H]$_3$; and (ii) R$_1$ through R$_3$ are not each an unsubstituted C$_1$-C$_8$ hydrocarbon.

In one embodiment of the above method, the compound has the structure according to the following formula:

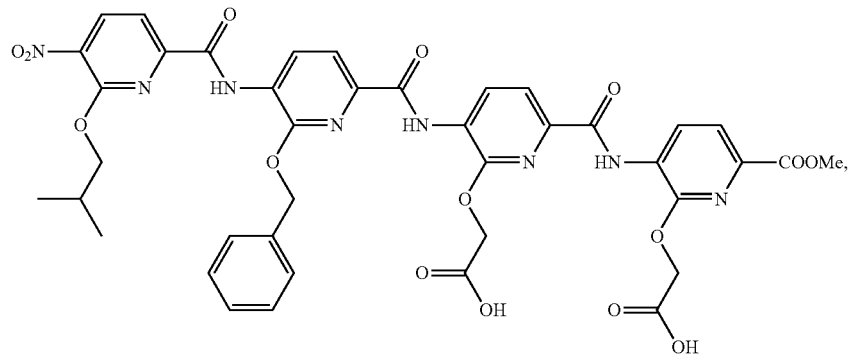 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

In one embodiment of the above method, the compound has the structure according to the following formula:

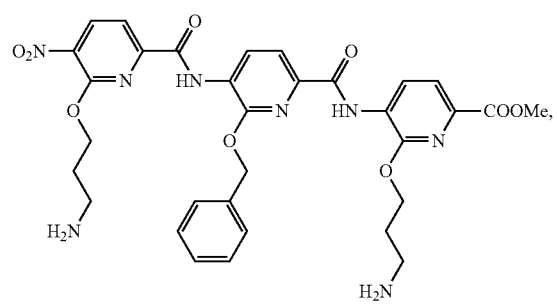 [SMILES: COC(=O)c1ccc(NC(=O)c2ccc(NC(=O)c3ccc([N+](=O)[O-])c(OCCCN)n3)c(OCc3ccccc3)n2)c(OCCCN)n1]

or a pharmaceutically acceptable salt thereof.

In one embodiment of the above method, the compound has the structure according to the following formula:

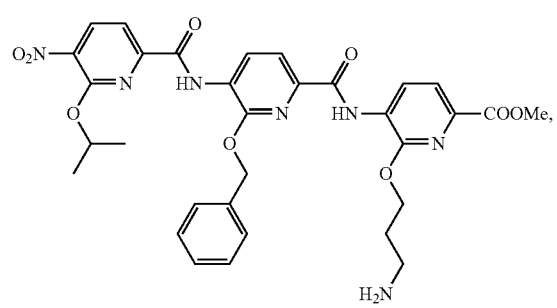 [SMILES: COC(=O)c1ccc(NC(=O)c2ccc(NC(=O)c3ccc([N+](=O)[O-])c(OC(C)C)n3)c(OCc3ccccc3)n2)c(OCCCN)n1]

or a pharmaceutically acceptable salt thereof.

In one embodiment of the above method, the compound has the structure according to the following formula:

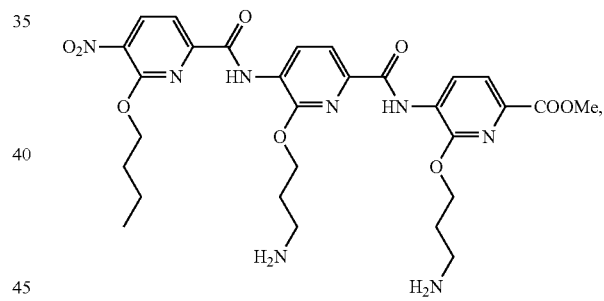

or a pharmaceutically acceptable salt thereof.

In one embodiment of the above method, the compound has the structure according to the following formula:

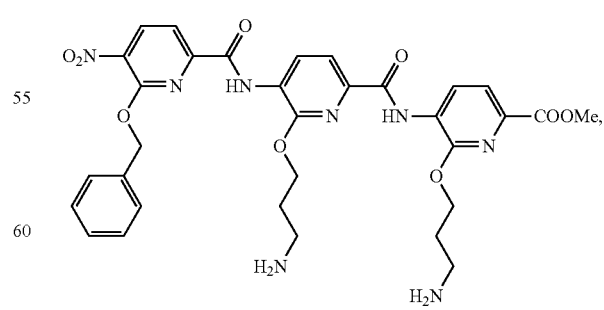

or a pharmaceutically acceptable salt thereof.

In one embodiment of the above method, the compound has the structure according to the following formula:

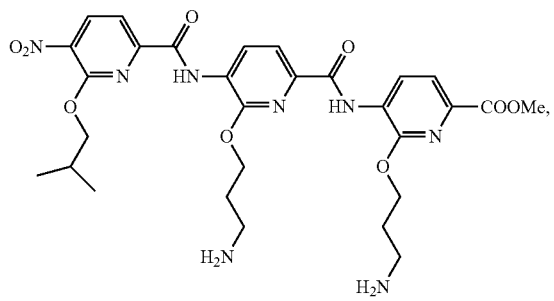 [SMILES: COC(=O)c1ccc(NC(=O)c2ccc(NC(=O)c3ccc([N+](=O)[O-])c(OCC(C)C)n3)c(OCCCN)n2)c(OCCCN)n1]

or a pharmaceutically acceptable salt thereof.

In yet another aspect, a method of treating cancer associated with a mutation in p53 in a subject in need of such treatment is provided, comprising administering to said subject an effective amount of a compound of formula (I):

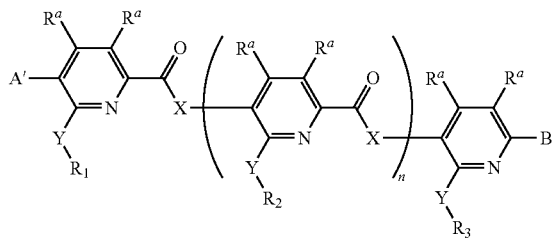

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and —C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)— OH; —O—N(R*)$_2$; —N(R*)—O—R*; —CN; —NC; —(C=O)—R*; —CHO; —CO$_2$H; —CO$_2$R*; —(C=O)— S—R*; —O—(C=O)—H; —O—(C=O)—R*; —S— (C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)— H; —O—(C=O)—R*; —S—(C=O)—R*; —(C=O)— NH$_2$; —(C=O)—N(R*)$_2$; —(C=O)—NHNH$_2$; —O— (C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_3$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)— OH; —O—N(R*)$_2$; —N(R*)—O—R*; —CN; —NC; —(C=O)—R*; —CHO; —CO$_2$H; —CO$_2$R*; —(C=O)— S—R*; —O—(C=O)—H; —O—(C=O)—R*; —S— (C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

A is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)— NHNH$_2$; —O—(C=O)—NHNH$_2$; —(C=S)—NH$_2$; —(C=S)—N(R*)$_2$; —N(R*)—CHO; —N(R*)— (C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl;

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)— NHNH$_2$; —O—(C=O)—NHNH$_2$; —(C=S)—NH$_2$; —(C=S)—N(R*)$_2$; —N(R*)—CHO; —N(R*)— (C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl;

R* is independently selected at each occurrence from hydrogen or $C_1$-$C_{12}$ hydrocarbons each of which optionally contains 1-8 heteroatoms selected from halogen, O, N, and S and combinations thereof; and n is an integer from 0 to 2;

or a pharmaceutically acceptable salt thereof.

In some embodiments, (i) when n is 0, and Y is O, $R_1$ and $R_3$ are not both —$CH_2CO_2H$; (ii) when n is 1, Y is O, and $R_1$ and $R_3$ are both —$CH_2CO_2H$, $R_2$ is not —$CH_2CO_2H$ or a straight chained, branched or cyclic aliphatic or aryl $C_1$-$C_{12}$ hydrocarbon, or $R_2$ does not have the structure —$C(CH_2CO_2H)_3$; (iii) when n is 1, and Y is O, $R_1$ through $R_3$ are not each an unsubstituted $C_1$-$C_8$ hydrocarbon; and (iv) when n is 2, and Y is O, $R_1$ through $R_3$ are not —$CH_2CO_2H$ at all occurrences.

In one embodiment of the above method, the p53 protein comprises one or more mutations.

In one embodiment of the above method, the p53 protein comprises one or more mutations at amino acid locations selected from R175, G245, R248, R249, I254, R273, and R282. In one embodiment of the above method, the p53 protein comprises one or more mutations selected from R248W, R248Q, and I254R.

In one embodiment, the p53 protein comprises R248W mutation.

In one embodiment, the p53 protein is in a cell.

In one embodiment, the cell is in a subject.

In one embodiment of the above method, the compound has the structure according to formula (II):

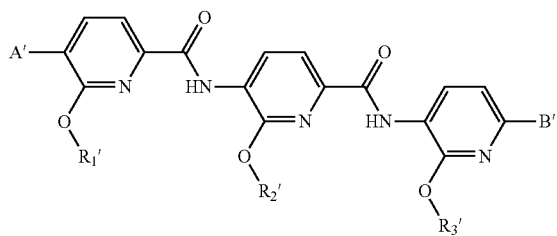

(II)

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —NHR*; —N(R*)$_2$; —N(R*)$_3^+$; —(C=O)—R*; —CHO; —$CO_2H$; —$CO_2R^*$; —(C=O)—S—R*; —O—(C=O)—H; —O—(C=O)—R*; and combinations thereof;

$R_2'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —NHR*; —N(R*)$_2$; —N(R*)$_3^+$; —(C=O)—R*; —CHO; —$CO_2H$; —$CO_2R^*$; —(C=O)—S—R*; —O—(C=O)—H; —O—(C=O)—R*; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —$NH_2$; —NHR*; —N(R*)$_2$; —N(R*)$_3^+$; —(C=O)—R*; —CHO; —$CO_2H$; —$CO_2R^*$; —(C=O)—S—R*; —O—(C=O)—H; —O—(C=O)—R*; and combinations thereof;

A' is selected from —$NO_2$; —$NH_2$; —NHR*; —N(R*)—(C=O)—R*, —N(R*)$_2$, where R* is hydrogen or an aliphatic $C_1$-$C_{12}$ hydrocarbon; and B' is selected from —(C=O)—R*; —$CO_2H$; —$CO_2R^*$, where R* is hydrogen or an aliphatic $C_1$-$C_{12}$ hydrocarbon;

R* is independently selected at each occurrence from hydrogen or $C_1$-$C_{12}$ hydrocarbons each of which optionally contains 1-8 heteroatoms selected from halogen, O, N, and S and combinations thereof;

or a pharmaceutically acceptable salt thereof.

In one embodiment, (i) when $R_1$ and $R_3$ are both —$CH_2CO_2H$, $R_2$ is not —$CH_2CO_2H$ or a straight chained, branched or cyclic aliphatic $C_1$-$C_{12}$ hydrocarbon, or $R_2$ does not have the structure —$C[CH_2CO_2H]_3$; and (ii) $R_1$ through $R_3$ are not each an unsubstituted $C_1$-$C_8$ hydrocarbon.

In one embodiment of the above method, the compound has the structure according to the following formula:

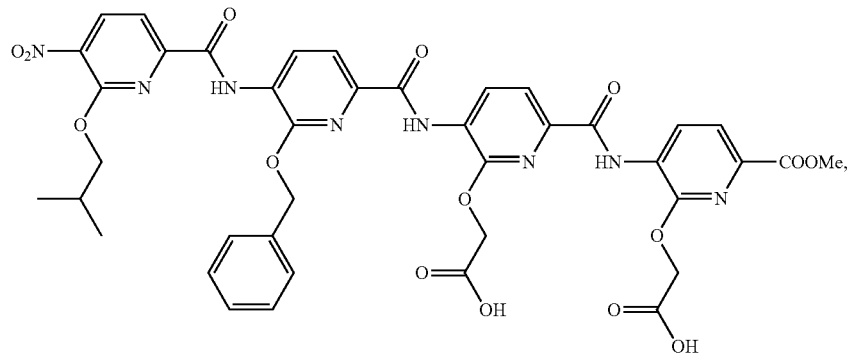 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

In one embodiment of the above method, the compound has the structure according to the following formula:

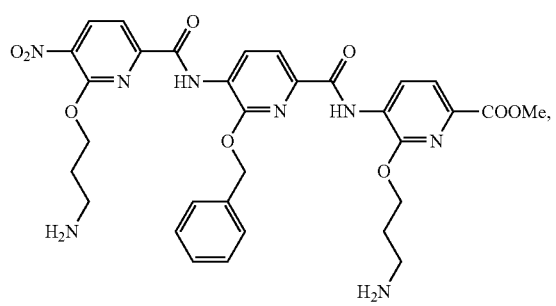 [SMILES: COC(=O)c1ccc(NC(=O)c2ccc(NC(=O)c3ccc([N+](=O)[O-])c(OCCCN)n3)c(OCc3ccccc3)n2)c(OCCCN)n1]

or a pharmaceutically acceptable salt thereof.

In one embodiment of the above method, the compound has the structure according to the following formula:

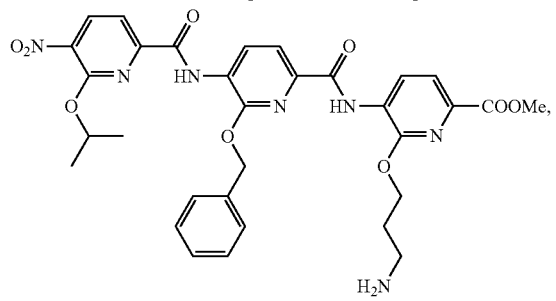

or a pharmaceutically acceptable salt thereof.

In one embodiment of the above method, the compound has the structure according to the following formula:

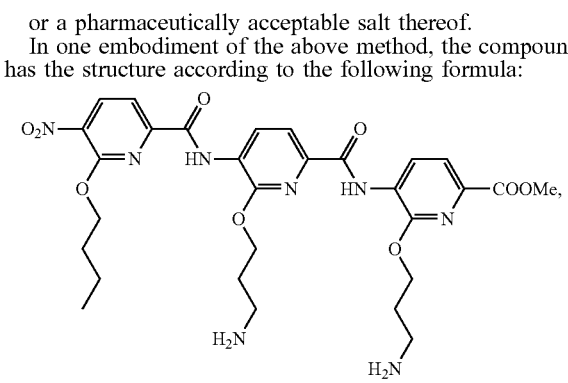

or a pharmaceutically acceptable salt thereof.

In one embodiment of the above method, the compound has the structure according to the following formula:

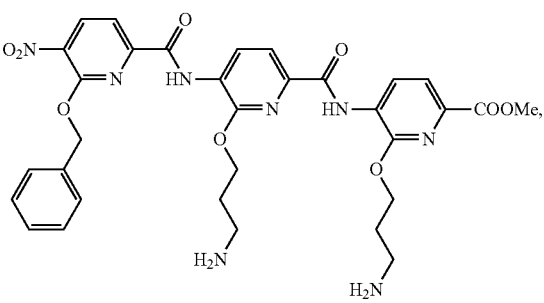 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

In one embodiment of the above method, the compound has the structure according to the following formula:

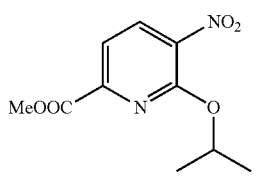

or a pharmaceutically acceptable salt thereof.

Some exemplary non-limiting embodiments of the compounds of the invention (and their monomer precursors) suitable for use in the methods of the invention are shown below:

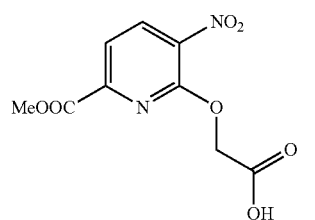

ADH-1

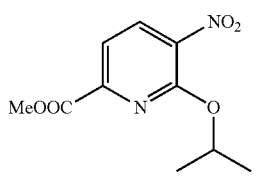

ADH-2

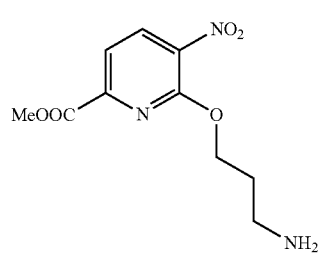

ADH-3

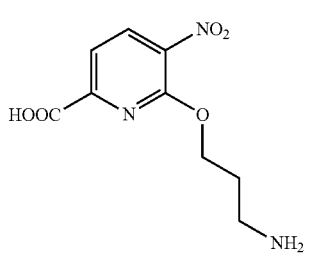

ADH-3a

-continued
ADH-4
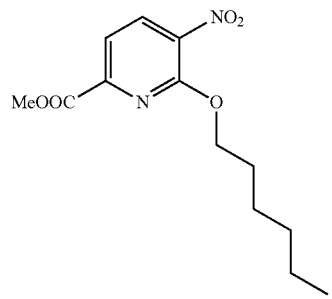
ADH-5
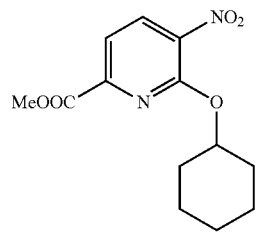
ADH-6
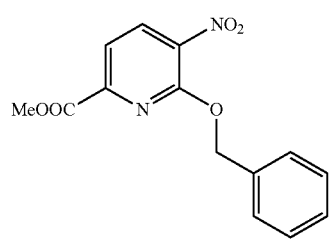
ADH-6a
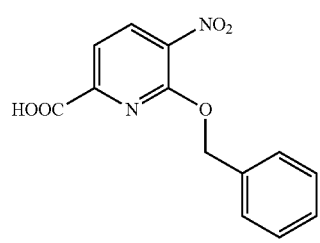
ADH-7
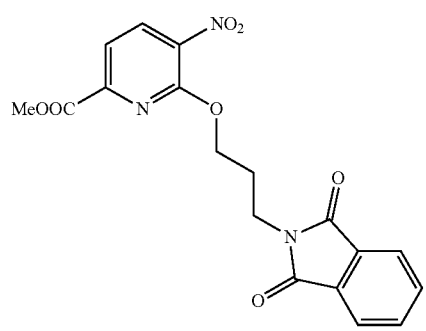
ADH-8
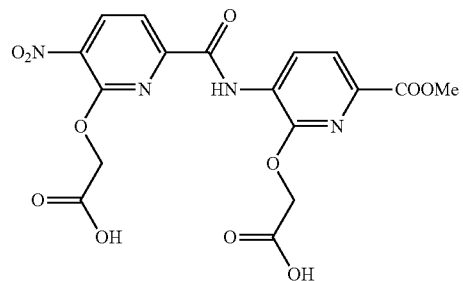
ADH-9
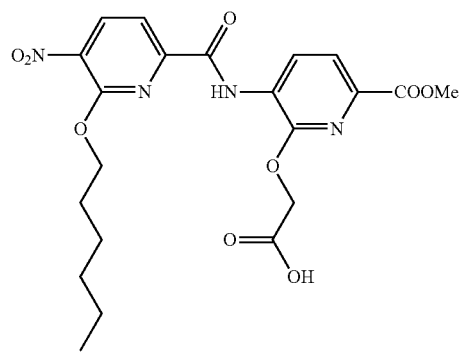
ADH-10
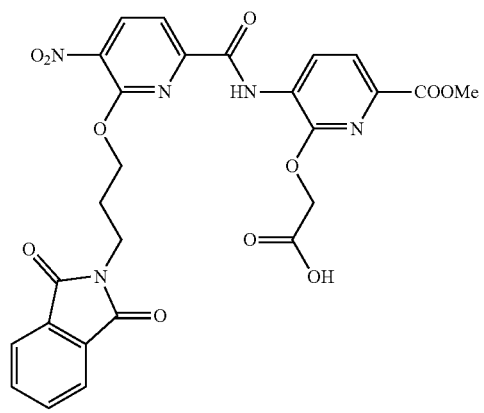
ADH-11
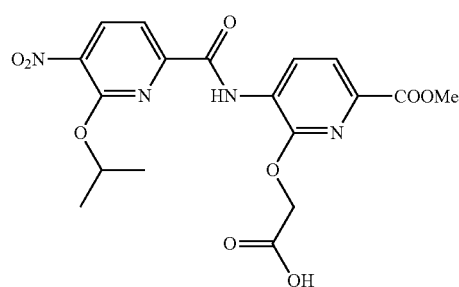
ADH-12
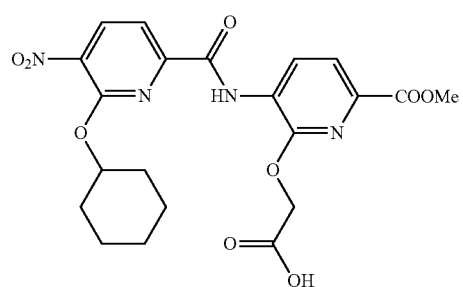

-continued
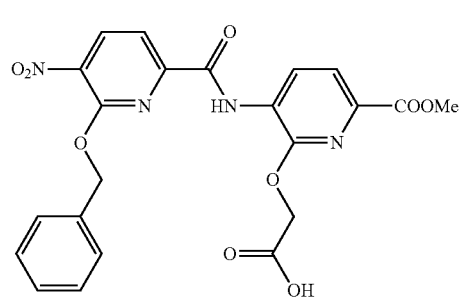
ADH-13
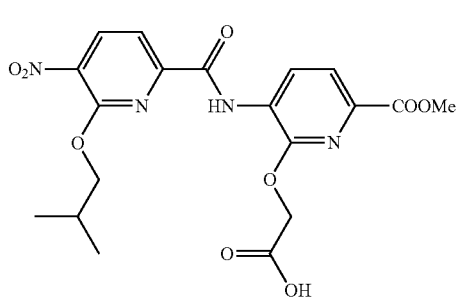
ADH-14
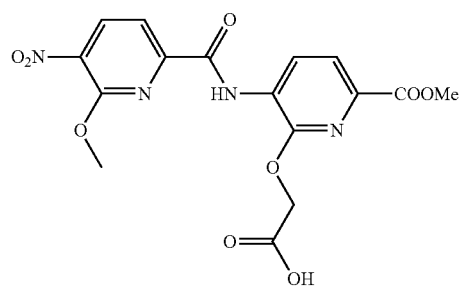
ADH-15
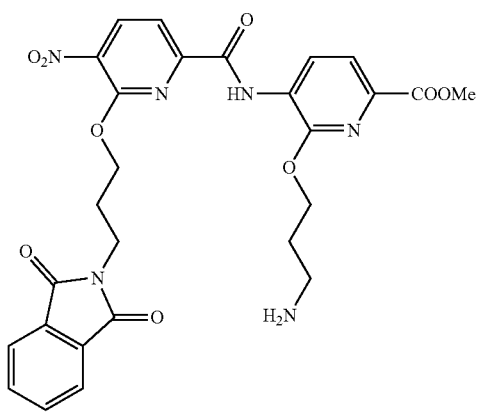
ADH-16
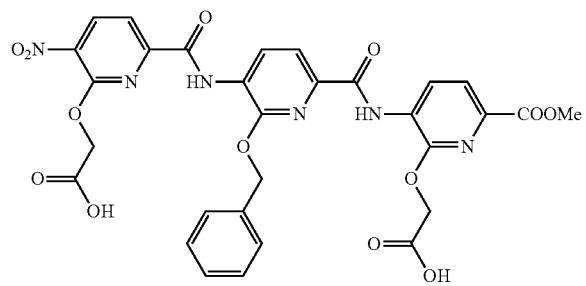
ADH-17
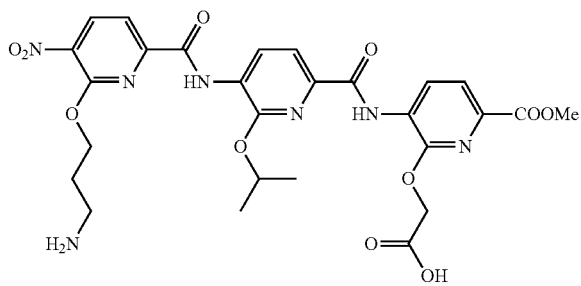
ADH-18
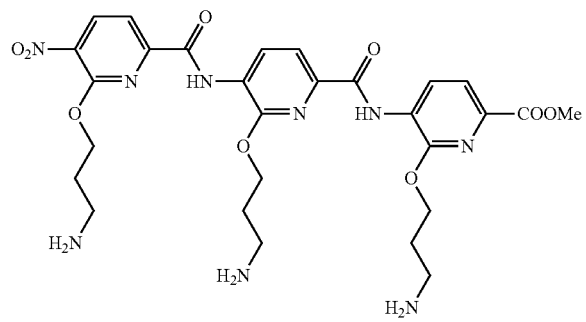
ADH-19
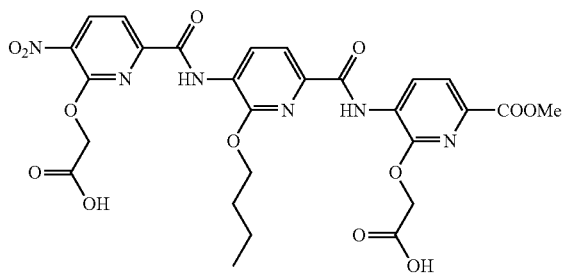
ADH-20

-continued
ADH-21
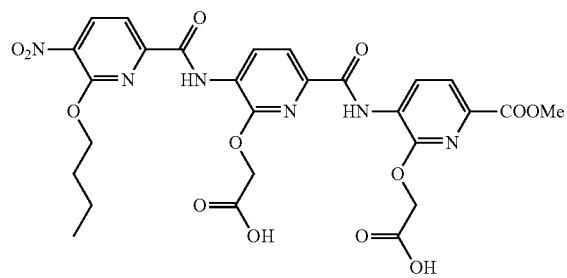
ADH-22
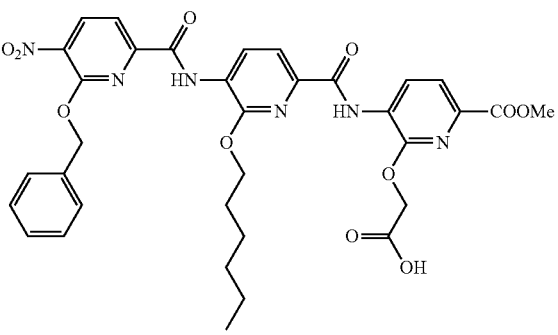
ADH-23
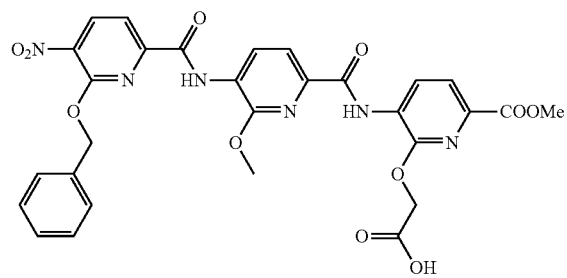
ADH-24
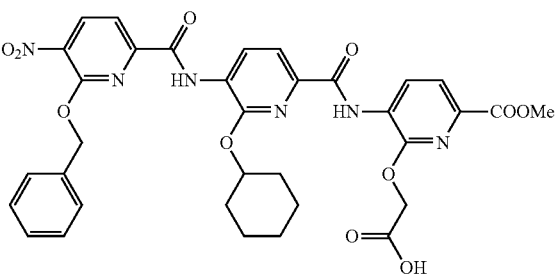
ADH-25
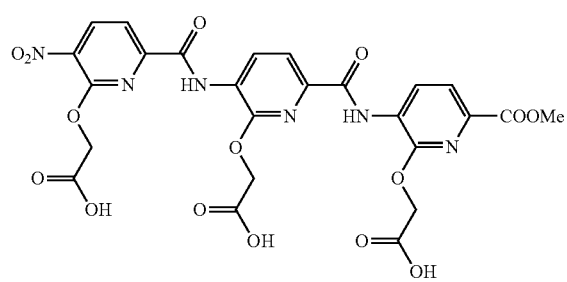
ADH-26
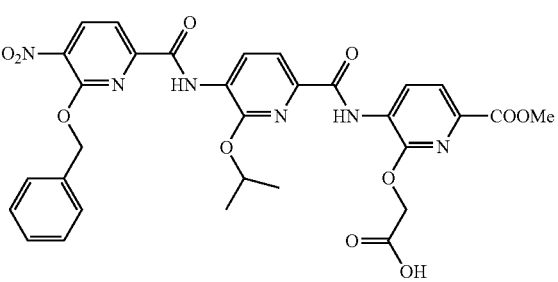
ADH-27
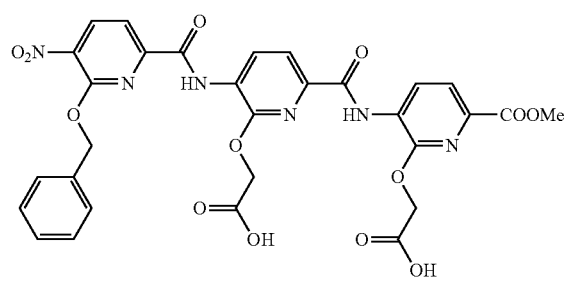
ADH-28
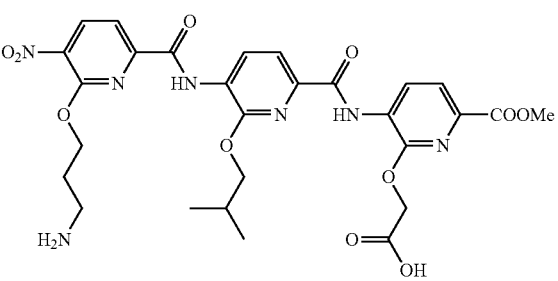
ADH-29
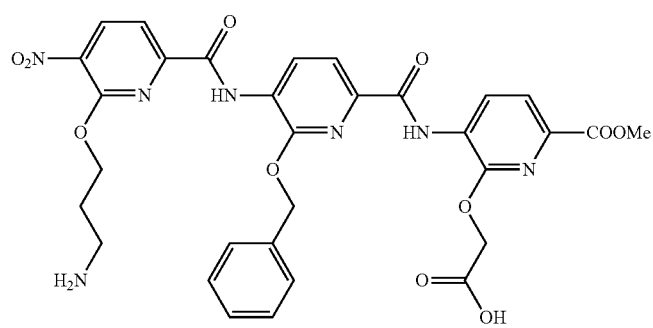

-continued
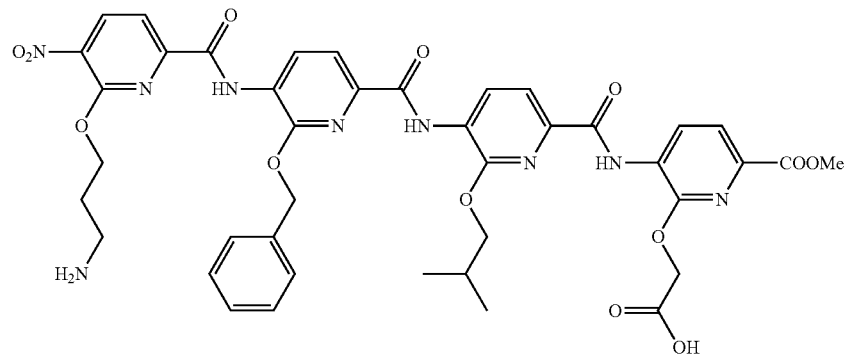
ADH-30
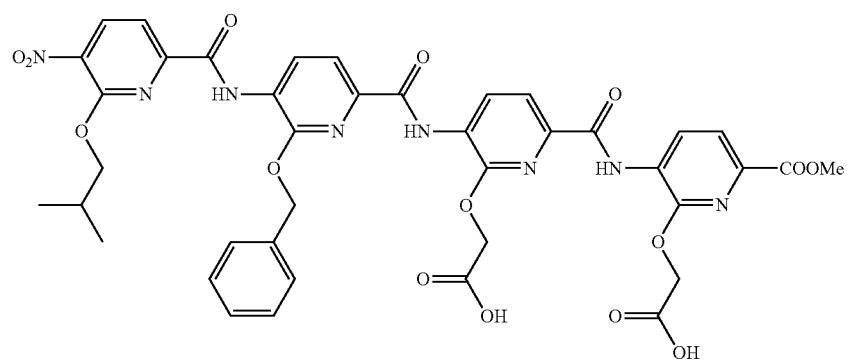
ADH-31
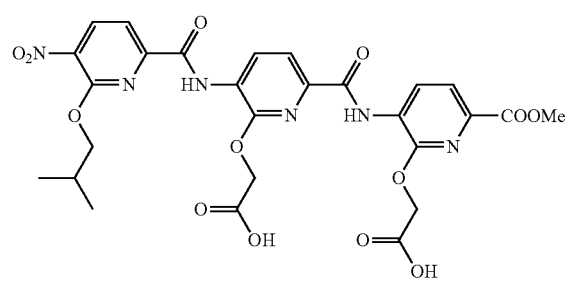
ADH-32
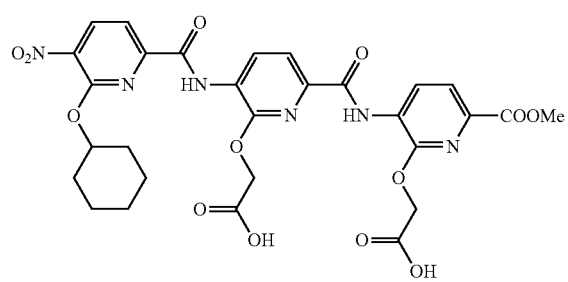
ADH-33
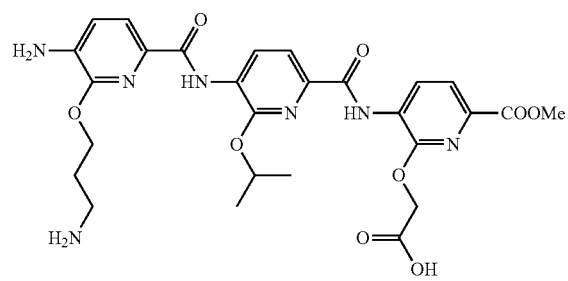
ADH-34
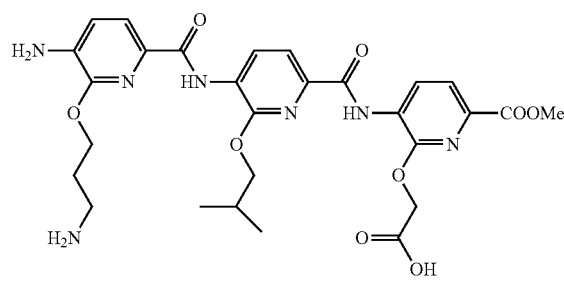
ADH-35
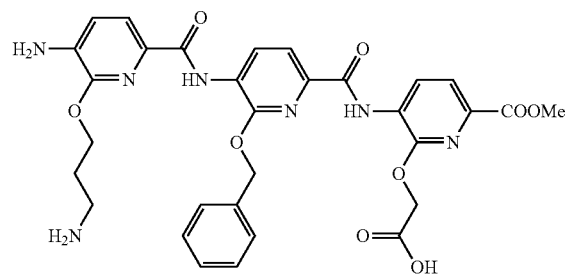
ADH-36
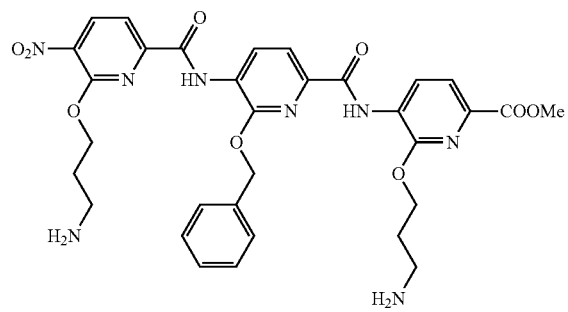
ADH-37

ADH-38
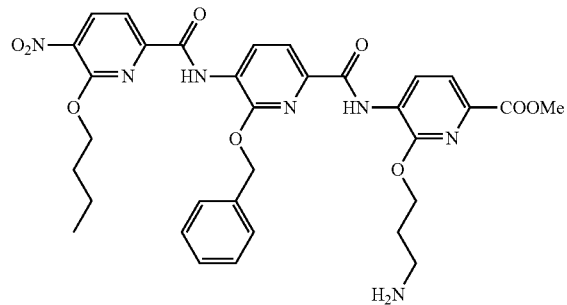
ADH-39
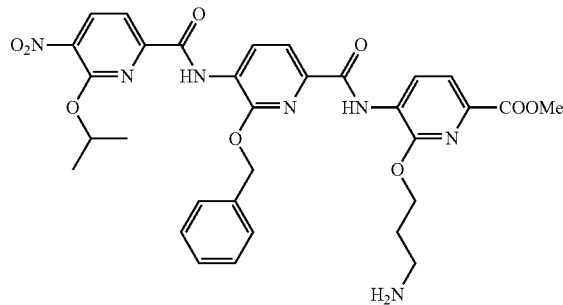
ADH-40
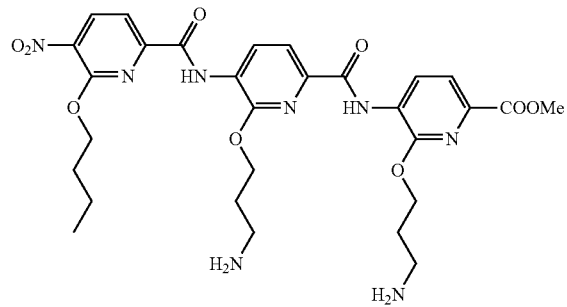
ADH-41
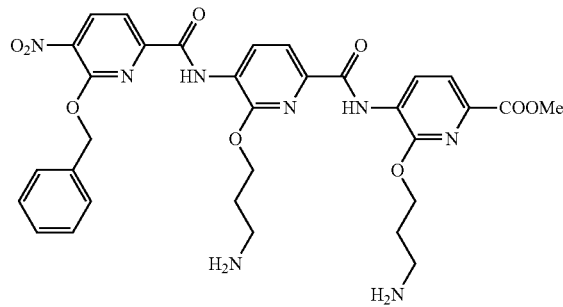
ADH-43
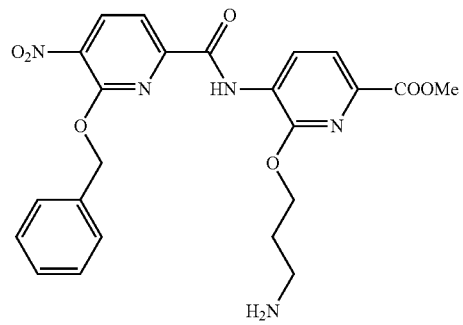
ADH-44
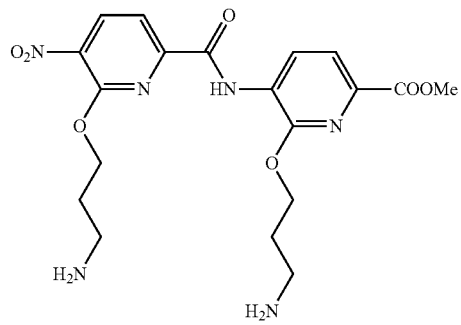
ADH-45
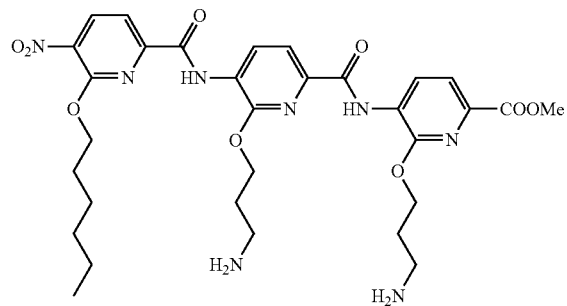
ADH-45A
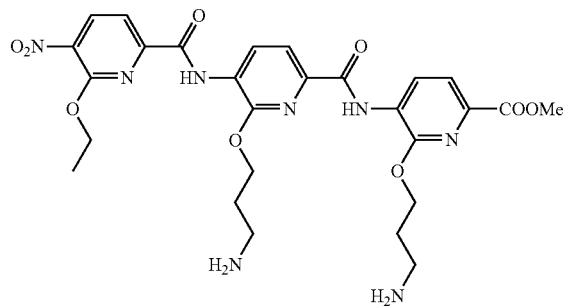

-continued
ADH-46
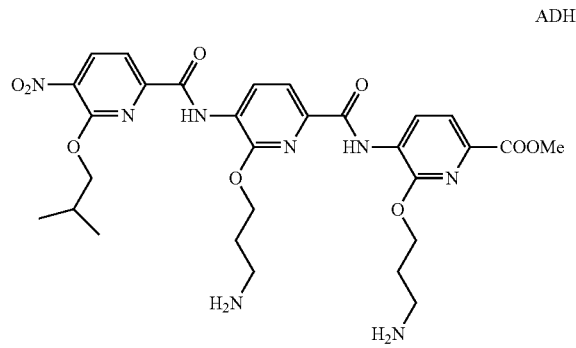
ADH-47
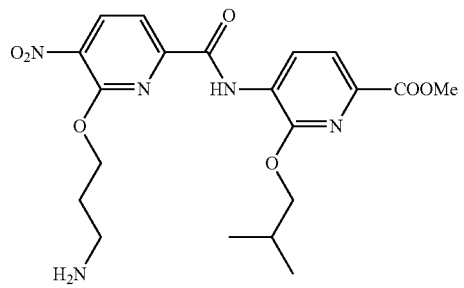
ADH-48
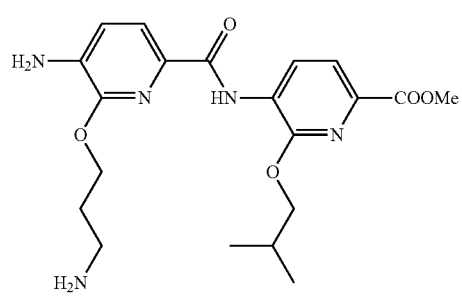
ADH-49
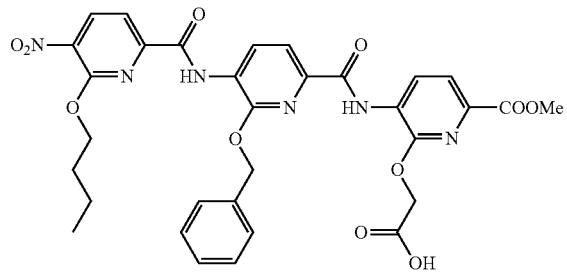
ADH-50
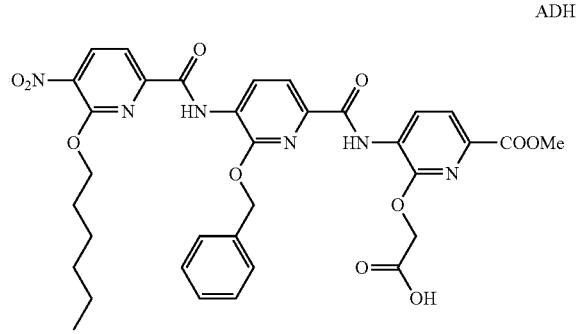
ADH-51
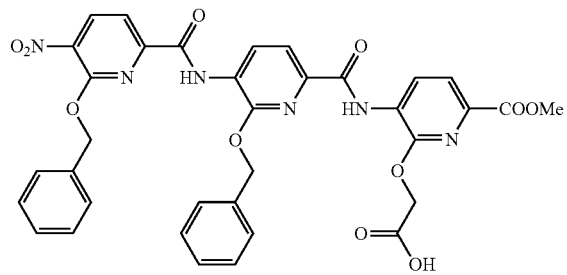
ADH-52
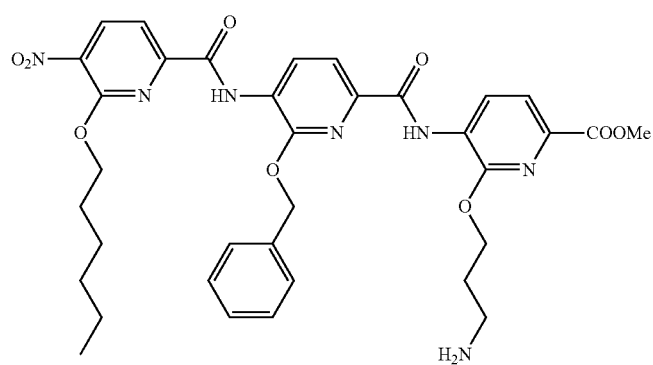

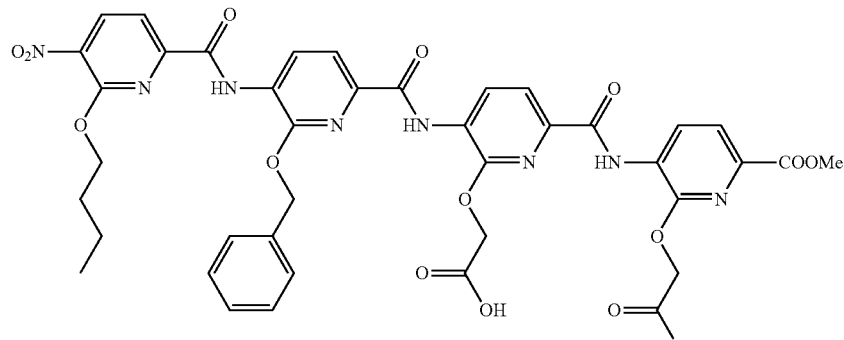

ADH-53

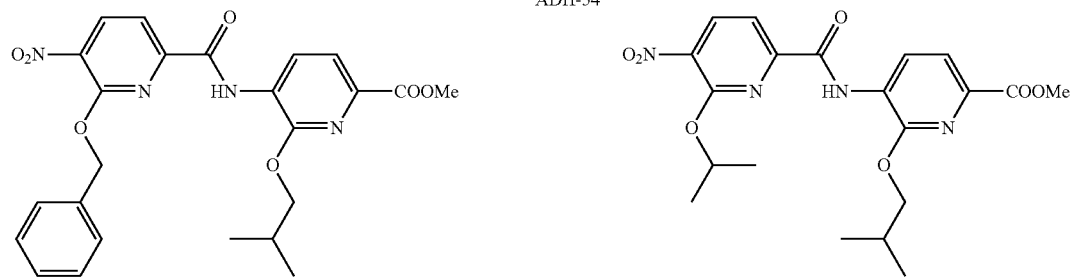

ADH-54

ADH-55

The methods of the present invention also include the use of salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, H2SO4) or organic acid (such as acetic acid, benzoic acid, trifluoroacetic acid salts of basic residues such as amines; alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, Greene Protective Groups in Organic Synthesis, 4th Ed., John Wiley & Sons: New York, 2006.

Pharmaceutical Compositions and Dosage Forms

The methods of the present invention also provide for use of pharmaceutical compositions comprising the compounds described herein. When employed as pharmaceuticals, the compounds of the invention can be administered in the form of pharmaceutical compositions which is a combination of the compounds of the invention and a pharmaceutically acceptable carrier. These compositions can be prepared in a manner well known in the pharmaceutical art, and can be administered by a variety of routes. Such pharmaceutical compositions can be administered systemically. The term "systemic" as used herein includes parenteral, topical, transdermal, oral, by inhalation/pulmonary, rectal, nasal, buccal, and sublingual administration. The term "parenteral" as used herein includes subcutaneous, intradermal, intravenous, intramuscular, intracranial, and intraperitoneal administration. Preferably, the compounds are administered intramuscularly, subcutaneously, orally, or intranasally in therapeutically effective amounts to treat diseases characterized by a formation of aggregates and/or fibers of peptides (e.g., p53).

Pharmaceutical compositions containing the compounds of the invention can be prepared in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical composition of the invention is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the pharmaceutical composition of the invention is a solid dosage form, such a tablet, a granule, a sachet, or a powder. Also provided are pharmaceutical compositions comprising a compound of the invention or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition is in a unit dose formulation for oral, intranasal, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds or compositions described herein are administered intranasally. As used herein, "nasal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired nasal delivery characteristics (e.g., as measured at the site of delivery, or at a selected target site of activity such as the brain) of the compounds or compositions of the invention. Enhancement of mucosal delivery can thus occur by any of a variety of mechanisms, for example by increasing the diffusion, transport, persistence or stability of the compounds or compositions of the invention, enzyme inhibition, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, increasing nasal blood flow and other mechanisms. Suitable mucosal delivery enhancing agents will be clear to a person skilled in the art of pharmacology and are further described hereafter.

Compositions of the invention can be simple aqueous (e.g., saline) solutions. Alternatively, they can contain various additional ingredients which enhance stability and/or nasal delivery of the compounds of the invention. Such additional ingredients are well known in the art. Non-limiting examples of useful additional ingredients for enhancing nasal delivery include, e.g., (a) aggregation inhibitory agents (e.g., polyethylene glycol, dextran, diethylaminoethyl dextran, and carboxymethyl cellulose), (b) charge modifying agents, (c) pH control agents, (d) degradative enzyme inhibitors (e.g., amastatin and bestatin [see, e.g., O'Hagan et al., Pharm. Res. 1990, 7: 772-776 and WO 05/120551]; (e) mucolytic or mucus clearing agents (e.g., n-acetyl-cysteine, propyl gallate and cysteine methionine dimers, chaotropes [see, e.g., WO 04/093917]), (f) ciliostatic agents; (g) membrane penetration enhancing agents, (h) modulatory agents of epithelial junction physiology, such as nitric oxide (NO) stimulators, chitosan, and chitosan derivatives; (i) vasodilator agents, (j) selective transport-enhancing agents, and (k) stabilizing delivery vehicles, carriers, supports or complex-forming agents. See, e.g., EP 037943, EP 094157, EP 173990, EP 214898, EP 215697, EP 327756, EP 490806, U.S. Pat. Nos. 4,476,116, 5,759,565, WO 04/093917 and WO 05/120551.

Non-limiting examples of membrane penetration-enhancing agents useful in the compositions of the invention include, e.g., (i) a surfactant (e.g., Tween 80, Poloxamer 188, polysorbates; see also EP 490806, U.S. Pat. No. 5,759,565, and WO04/093917), (ii) a bile salt or bile salt derivative (e.g., unsaturated cyclic ureas and Transcutol), (iii) a phospholipid or fatty acid additive, mixed micelle, liposome, or carrier, (iv) an alcohol, (v) an enamine, (vi) a nitric oxide donor compound (e.g., S-nitroso-N-acetyl-DL-penicillamine, $NOR_1$, $NOR_4$, which are preferably co-administered with an NO scavenger such as carboxy-PITO or doclofenac sodium), (vii) a long-chain amphipathic molecule (e.g., deacylmethyl sulfoxide, azone, sodium lauryl sulfate, oleic acid) (viii) a small hydrophobic penetration enhancer, (ix) sodium salicylate or a salicylic acid derivative (e.g., acetyl salicylate, choline salicylate, salicylamide, etc.), (x) a glycerol ester of acetoacetic acid, (xi) a cyclodextrin or betacyclodextrin derivative, (xii) a medium-chain fatty acid including mono- and diglycerides (e.g., sodium caprate—extracts of coconut oil, Capmul), (xiii) a chelating agent (e.g., citric acid, salicylates), (xiv) an amino acid or salt thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc., inclusive of their alkali metal or alkaline earth metal salts), (xv) an N-acetylamino acid or salt thereof, (xvi) an enzyme degradative to a selected membrane component, (xvii) an inhibitor of fatty acid synthesis, (xviii) an inhibitor of cholesterol synthesis, (xix) cationic polymers, or any combination thereof. The membrane penetration-enhancing agent can be also selected from small hydrophilic molecules, including but not limited to, dimethyl sulfoxide (DMSO), dimethylformamide, ethanol, propylene glycol, and the 2-pyrrolidones. Additional membrane penetration enhancers include emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like; mixed micelles; glycerol esters of acetoacetic acid (e.g., glyceryl-1,3-diacetoacetate or 1,2-isopropylideneglycerine-3-acetoacetate), and triglycerides (e.g., amylodextrin, Estaram 299, Miglyol 810); cyclodextrins and β-cyclodextrin derivatives (e.g., 2-hydroxypropyl-β-cyclodextrin and heptakis (2,6-di-O-methyl-β-cyclodextrin) which can be optionally conjugated with Peptide and further optionally formulated in an oleaginous base; and N-acetylamino acids (N-acetylalanine, N-acetylphenylalanine, Nacetylserine, N-acetylglycine, N-acetyllysine, N-acetylglutamic acid, N-acetylproline, Nacetylhydroxyproline, etc.) and their salts (alkali metal salts and alkaline earth metal salts), as well as other penetration-promoting agents that are physiologically compatible for intranasal delivery. See, e.g., WO 04/093917, WO 05/120551 and Davis and Ilium (Clin. Pharmacokinet 2003, 42: 1107-1128).

Non-limiting examples of useful absorption enhancers include, e.g., surfactants, glycosides, cyclodextrin and glycols. Non-limiting examples of useful bioadhesive agents include, e.g., carbopol, cellulose agents, starch, dextran, and chitosan.

In various embodiments of the invention, a compound of the invention is combined with one or more of the nasal delivery-enhancing agents recited above. These nasal delivery-enhancing agents may be admixed, alone or together, with the nasal carrier and with the compound of the invention, or otherwise combined therewith in a pharmaceutically acceptable formulation or delivery vehicle. For nasal delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the nasal mucosa with long term use.

In addition to the compound of the invention, the nasal carrier and, optionally, one or more further additives and/or agents, the composition of the invention may further comprise one or more additional therapeutic ingredients (or active substances). These therapeutic ingredients can be any compound that elicits a desired activity or therapeutic or biological response in the subject. Non-limiting examples of useful additional therapeutic ingredients is provided in the Combination Treatments section, below.

The proportion of each further component in the nasal composition of the invention may vary depending on the components used. For example, but without being limiting, the amount of nasal carrier may be in the range of from 0.1 to 99.9% by weight of the total weight or volume of the composition. When present, the amount surfactant may be in the range from about 0.01 to about 10% or higher and preferably about 0.05 to about 1.0% by weight of the total volume or weight of the composition, the amount depending on the specific surfactant used. The amount is generally kept as low as possible since above a certain level no further enhancement of absorption can be achieved and also too high of a surfactant level may cause irritation of the nasal mucosa. The amount of delivery enhancing agents may be at least 0.1%, suitably in the range from about 0.5 to 10% of the total weight of the composition. Where the composition is liquid, the enhancing agent may suitably be present in an amount of from 0.1 to 5% w/v of the total composition. Preserving agents may be present in an amount of from about 0.002 to 0.02% by weight of the total weight or volume of the composition.

The useful delivery volume of the pharmaceutical compositions of the invention is limited by the size of the nasal cavity. Suitable delivery volumes will be clear to a person skilled in the art of pharmacology. Preferably, the total composition quantity administered at each nasal application comprises from about 0.02 to 0.5 ml, preferably about 0.07 to 0.3 ml, typically about 0.09-0.1 ml.

The liquid compositions of the invention may be prepared by bringing into intimate admixture a compound the invention in the liquid carrier optionally together with the further ingredients, additives and/or agents. The solid nasal composition of the invention may be prepared in conventional manner. A compound of the invention may be admixed with the carrier particles, e.g. a polymer base or cellulose product in conventional manner, optionally with further ingredients, additives and/or agents as indicated above e.g. a mucosal delivery enhancing agent or surfactant such as disclosed. A compound of the invention may be in solution e.g. an aqueous or alcoholic solution when being mixed with the carrier particles and the solvent evaporated, e.g. under freeze-drying or spray drying. Such drying may be effected under the conventional conditions. Alternatively, the mixture may be compacted or granulated and then be pulverized and/or sieved. If desired the particles may be coated. In one embodiment of the invention, the nasal composition is prepared by lyophilisation. A homogeneous solution, preferably aqueous, containing a compound of the invention and optionally containing further ingredients, additives and/or agents as discussed above, is prepared and then submitted to lyophilisation in analogy with known lyophilisation procedures, and to subsequent drying. The resulting powder may then be dissolved in a liquid excipient or nasal carrier before administration, e.g. to reconstitute nasal drops, gel or spray. Alternatively, it may be administered as such in the form of lyophilized powder or it may be mixed with further ingredients, additives and/or agents as discussed above. For example, a lyophilized powder comprising a compound of the invention but free of any nasal carrier may be prepared and then admixed with the desired nasal carrier or mixture of nasal carriers.

The present invention encompasses any delivery device that is suitable for nasal administration of the compositions of the invention. Preferably, such means administers a metered dosage of the composition. The composition of the present invention may be packed in any appropriate form or container as long as a means is provided to deliver the composition to the nasal mucosa. Non-limiting examples of useful intranasal delivery devices include, e.g., instillation catheters, droppers, unit-dose containers, squeeze bottles pump sprays, airless and preservative-fee sprays, compressed air nebulizers, metered-dose inhalers, insufflators and pressurized metered dose inhalers.

For administration of a liquid in drop form, compositions of the invention can be placed in a container provided with a conventional dropper/closure device, e.g. comprising a pipette or the like, preferably delivering a substantially fixed volume of composition/drop.

For administration of an aqueous solution as a nasal spray, the aqueous solution may be dispensed in spray form by a variety of methods known to those skilled in the art. For example, such compositions will be put up in an appropriate atomising device, e.g. in a pump-atomiser, or the like. The atomising device will be provided with appropriate means, such as a spray adaptor for delivery of the aqueous spray to the naris. Preferably it will be provided with means ensuring delivery of a substantially fixed volume of composition/actuation (i.e. per spray-unit). Examples of nasal sprays include nasal actuators produced by Ing. Erich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g., compressed air-, jet-, ultrasonic-, and piezoelectric nebulizers.

Alternatively, the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present.

A dry powder may be readily dispersed in an inhalation device as described in U.S. Pat. No. 6,514,496 and Garcia-Arieta et al., Biol. Pharm. Bull. 2001; 24: 1411-1416.

If desired a powder or liquid may be filled into a soft or hard capsule or in a single dose device adapted for nasal administration. The powder may be sieved before filled into the capsules such as gelatine capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

In another embodiment, the composition of the invention can be provided as a nasal insert having the compound of the invention dispersed therein. The insert may be retained in the naris, but flushed by the nasal mucus, and may be designed to release the compound of the invention at the same place in the naris. Suitable nasal insert types include nasal plugs, tampons and the like. Further examples of nasal inserts, their characteristics and preparation are described in EP 490806.

In one aspect, a composition or unit dosage form according to the invention is formulated for sublingual administration, wherein the unit dosage form is a film including one or more disintegrants (e.g., materials that favor disintegration or fast dissolution by virtue of their solubility in water, such as hydrolyzed starches, sugars, and glycerin, which may play a dual role as a plasticizer and disintegrant) and a plasticizing agent, the film having a first portion including apomorphine hydrochloride, and a second portion including pH neutralizing agent, wherein the unit dosage form includes from 0.5 to 5 mg, from 4 to 10 mg, or from 8 to 20 mg of apomorphine hydrochloride and the pH neutralizing agent is present in an amount sufficient to produce a solution having a pH of between 3.0 and 6.0, preferably between 4.5 and 6.5, (e.g., a pH of between 2.5 and 4.5, 3.0 and 6.0, 3.5 and 6.5, 4.5 and 6.5, or 5.0 and 6.0) when the unit dosage form is placed in unbuffered water at pH 7 (e.g., the pH observed within 5 minutes of placing the unit dosage form in 1, 5, or 10 mL of unbuffered water). The film can include from 1 to 50% (w/w) (e.g., 1±0.75%, 2±1.5%, 3±0.5%, 5±2%, 7.5±2.5%, 10±2%, 14±3%, 18±4%, 22±5%, 25±5%, 30±5%, 35±5%, 40±5%, 45±5%, or 50±5% (w/w)) of the one or more disintegrants. In certain embodiments, the unit dosage form further includes a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose. In other embodiments, the unit dosage form further includes a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose. The pH neutralizing agent can be an organic base (e.g., pyridoxine, meglumine, or any organic base described herein) or an inorganic base (e.g., magnesium hydroxide, sodium bicarbonate, or an inorganic base described herein). In particular embodiments, the unit dosage form includes 35±5% (w/w) disintegrant, from 0.5 to 5 mg, from 4 to 10 mg, or from 8 to 20 mg of apomorphine hydrochloride and pyridoxine present in an amount sufficient to produce a solution having a pH of between 4.5 and 6.5 when the unit dosage form is placed in unbuffered water at pH 7. Suitable film for oral administration of the compositions according to the invention is disclosed in, e.g., U.S. Pat. No. 8,846,074.

In some embodiments, a composition or unit dosage form described herein is administered as an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of compound of formula (I) per day or per dose is administered to an individual.

In some embodiments, the compound of the invention is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of corticosteroid administered daily or in a unit dose is between about 0.5 mg and about 3 mg, between about 0.5 mg and about 4 mg, or between about 0.35 mg and about 4 mg. In other embodiments, the amount of the compound present in a unit dose or administered daily is between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the compound per day or per dose is administered to a patient.

In some embodiments, the compound is present in a unit dose in an amount of between about 5 mg and about 500 mg. In some embodiments, the amount of the compound administered daily or in a unit dose is between about 5 mg and about 300 mg. In other embodiments, the amount of the compound present in a unit dose or administered daily is between about 5 and about 250 mg, or between about 5 and about 200 mg, between about 5 mg and about 150 mg, between about 5 mg and about 100 mg, or between about 5 and about 50 mg.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid pre-formulation composition containing a homogeneous mixture of the compound of Formula I. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing the compound of Formula I can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9. It will be understood that use of certain of the foregoing excipients, carriers, or stabilizers will result in the formation of pharmaceutical salts.

The therapeutic dosage of the compounds of the invention can vary according to, for example, the particular use for which the treatment is made, the manner of administration of the compound, the health and condition of the patient, and the judgment of the prescribing physician. The proportion or concentration of the compounds of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment or prevention of diseases characterized by a formation of oligomers and/or aggregates of p53, which include one or more containers containing a pharmaceutical composition comprising a therapeutically effective amount of the compounds of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

As demonstrated in the Examples, below, the ADH compounds according to the invention abrogate pre-formed mutant p53 aggregates past elongation and prevent further aggregation. Notably, ADH compounds appear to have no cytotoxic effects on cell lines containing functional wild-type p53. Moreover, the toxicity observed in HeLa cells presents an interesting opportunity to investigate p53 rescue in cell lines with compromised p53 function.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Instruments and Methods

Peptide Purification and Preparation.

Mutant peptide R248W, its wild-type form and inhibitors peptides G3-ReACp53, I254R, PAS-I254R and Penetratin were obtained in crude form from Selleck Chemicals. All peptides were purified using a Waters 2535 QGM Semi-Preparative HPLC equipped with a C18 reverse-phase column. Crude peptides were dissolved in trifluoroacetic acid (TFA) and diluted in guanidine hydrochloride (Gu-HCl) for HPLC preparation. Peptides were then isolated, lyophilized, characterized by mass spectroscopy and stored in pure DMSO under inert gas (N2). Peptides were stored in aliquots such that each sample underwent a maximum of 3 freeze-thaw cycles.

HPLC Analysis.

Most of the peptides used in the study lacked aromatic amino acid residues, thus necessitating quantification using an alternative method. Peptides were quantified using a time-consuming method that involves the construct of a standard peptide concentration plot using HPLC analysis. For this protocol, an Alligant Analytical HPLC was used to maximize sensitivity to low volumes of peptide solutions. A peptide concentration standard was constructed based on Penetratin (RQIKIWFQNRRMKWKK), which was chosen based on its similar properties and size to the peptides used in the study. The concentration was standardized by integrating the area under the UV absorbance curve that occurs at 214 nm (which represents the peptide backbone) when the peptide is eluted from the analytical column. Thus, all peptides were quantified by running a 10 μL sample through the HPLC for 10 minutes, integrating the area under the 214 nm curve at its retention time and then fitting the obtained value in the standard curve obtained with Penetratin.

Fluorescent Peptide Labeling.

Inhibitor peptides I254R, PAS-I254R and G3-ReACp53 were purified, characterized by mass spectrometry (LC-MS), quantified and exposed to an alkaline buffer during Alexa 488 labeling. Peptide concentrations of 500 μM and higher were used to maximize labeling efficiency. Peptides were incubated in the dark on shaker overnight and characterized by liquid-chromatography-mass spectroscopy (LC-MS) and analytical HPLC to ensure efficient labeling of the peptide. Another method for peptide labeling was implemented to maximize labeling efficiency, involving the use of a silica-based column to prevent peptide escape from labeling through self-aggregation. The peptide was loaded onto a prepped silica column, whereby Alexa 488 would be loaded shortly afterwards. Peptides were incubated in the dark on a shaker overnight, eluted from the column and then analyzed using LC-MS and analytical HPLC the next day.

Thioflavin T Assay.

Thioflavin T is a benzothiozole salt that fluoresces upon binding to beta-sheet structures (amyloid) and displays a distinctive red shift of the emission spectrum. This fluorescence can be monitored overtime to estimate the increase in beta-sheet structure of incubated peptides, indicating amyloid formation. Peptides that undergo amyloid formation exhibit a sigmoidal curve in the increase of ThT fluorescence overtime. 50 μM ThT was incubated at 37° C. with varying concentrations of peptides and inhibitors to estimate both the aggregation propensity of mutant peptides and the abrogation of aggregation brought about by inhibitor treatment. All samples were sonicated, including the ThT solution, prior to each addition of peptides to ensure the obtainment of clear sigmoidal curves. Fluorescence in transparent-bottom 96-well sample plates was monitored by the cell plate reader Synergy H1 (BioTek).

Transmission Electron Microscopy (TEM).

Transmission electron microscopy was performed using the FEI Talos F200X Transmission Electron Microscope. Mutant p53 samples were incubated for 24 hrs at 37° C. at a concentration of 50 μM. 300 mesh carbon-coated copper grids were plasma cleaned to impart a temporary charge to the surface of the grid, enhancing peptide binding and encouraging stronger staining. Peptide samples were allowed to bind to the grid for 3 minutes before staining with 2% tungsten phosphoric acid for 1 minute.

Circular Dichroism.

Circular dichroism (CD) was used to detect changes in the secondary structures of the wild type and mutant forms of p53 over time, as well as to monitor differences in secondary structure transition upon treatment with ADH-compounds. 25-50 μM of peptide was dissolved in deionized water with pH 7 at room temperature and placed in a 10,000 nm path length cuvette. CD spectra ranging from 290 to 180 nm were analyzed using a Chirsacan CD spectrometer.

Cell Culture.

MIA PaCa-2 (CRL-1420) cells, which contain the R248W p53 contact mutant, were obtained from ATCC and cultured in ATCC-formulated Dulbecco's Modified Eagle's Medium supplemented with with 10% fetal bovine serum (FBS), 2.5% horse serum, 4% 200 mM L-glutamine and 1% penicillin/streptomycin. A separate stock of serum-free medium was kept for cell viability assays. Cells were split at a 1:3 ratio 2-3 times a week and maintained at 80% confluence and >85% viability. Viability was regularly measured through Trypan Blue dilution correction during cell counting. Cell cultures were stored at 37° C. in T75 coated flasks and kept under 5% CO2.

MTS Assay.

MTS assays were performed with Promega CellTiter One MTS solution according to protocol. MIA PaCa-2 Cells were seeded at 2,000 cells/well and were incubated for 24 hours to allow proper adherence to the well. On treatment day, wells were washed with warm PBS and media was replaced with a serum-free version. If treatment peptides were purified from crude form, they were also filtered using a 0.2 m filter before introduction to cells. On MTS reading day, media was changed again (serum-free) and 20 μL of MTS was added to each 100 μL well. Cells were incubated at 37° C. for 2 hours before reading absorbance at 490 nm using Synergy H1 (BioTek) equipped with Gen5 software.

Immunohistochemistry.

Cells were seeded at 50,000 cells per well in 500 μL 4 well glass-bottom plates. Plates were incubated for 24 hours to allow cell adherence to glass-bottoms and were treated with labeled inhibitor peptides 1-6 hours before imaging. Cells were fixed using 4% PFA and permeabilized using 0.1%

Triton X. A blocking buffer of 5% bovine serum albumin (BSA) was used before primary antibody staining. Primary Anti-p53 Antibody (FL-393) was obtained from Santa Cruz Biotechnologies. A Texas red fluorescent rabbit polyclonal secondary antibody was used after 2 hours of primary antibody incubation at room temperature. Cells were incubated with secondary antibody for another 2 hours before washing and DAPI (nucleus) staining. Appropriate controls were used for each experiment.

Inverted Confocal Microscopy.

An Olympus FV1000 Confocal/2-Photon Inverted Microscope was used for all confocal imaging.

Annexin/PI FACS Assay.

Cells were seeded in 12 wells plates (20,000 cells/mL) and were left to adhere over 24 hours. Media was switched to a serum-free version on treatment day. On analysis day, cells were washed, harvested and washed again through centrifugation before resuspension in Annexin-binding buffer. 4 µL Annexin-FITC and 1 µL of a 100 ng/mL PI working solution was added to 100-200 µL samples. Cells were incubated for 15 minutes at room temperature in the dark and 400 uL of Annexin-binding buffer was added to the samples. Samples were then immediately transferred to ice before FACS analysis. FACS was performed using a BD FACS ARIA III machine.

Statistical Analysis and Graphing.

All statistical analysis of dose/drug-response experiments were carried out using two-way ANOVA and student's t test. All tests were two-tailed. Alpha values were adjusted to 0.0001. Abnormal sigmoidal curve fitting was performed using built-in algorithms by GraphPad Prism7 and JMP.

Cell Culture.

All cell lines were obtained from ATCC and maintained in recommended medium formulations. A separate stock of serum-free medium was kept for cell viability assays. Cells were split at a 1:3-1:10 ratio 2-3 times a week and maintained at 80% confluence and >85% viability. Viability was regularly measured through Trypan Blue dilution correction during cell counting. Cell cultures were stored at 37° C. in T75 coated flasks and kept under 5% CO2.

MTS Assay.

MTS assays were performed with Promega CellTiter One MTS solution according to protocol. MIA PaCa-2 cells were seeded at 2,000 cells/well, MCF-7 at 4,000 cells/well, COS-7 at 5,000 cells/well and HeLa at 3,000 cells/well. These values were individually optimized for the assay prior to experimentation. All cells were incubated for 24 hours to allow proper adherence to the well. On treatment day, wells were washed with warm PBS and media was replaced with a serum-free version. If treatment peptides were purified from crude form, they were also filtered using a 0.2 m filter before introduction to cells. On MTS reading day, media was changed again (serum-free) and 20 µL of MTS was added to each 100 µL well. Cells were incubated at 37° C. for 2 hours before reading absorbance at 490 nm using Synergy H1 (BioTek) equipped with Gen5 software. Background absorbance from control wells was quantified and subtracted from obtained experimental absorbance values.

Example 2: The Aggregation-Nucleating Region of p53 Contact Mutant R248W Undergoes Amyloid Formation In Vitro A reductionist approach was utilized in the elucidation of mutant p53 aggregation by investigating the aggregation behavior of two short peptide sequences: one containing the p53 WT aggregation-nucleating region and the other containing the R248W contact mutation (Table 1, below).

TABLE 1

Designed mutant p53 aggregation inhibitor sequences

| Peptide Name | Peptide Sequence | Description |
|---|---|---|
| WT | RRPILTIITLEDSSGNLLGRNSFEVR | Wild-type aggregation-nucleating region |
| R248W | WRPILTIITLEDSSGNLLGRNSFEVR | Contact mutant |

Figure 2:
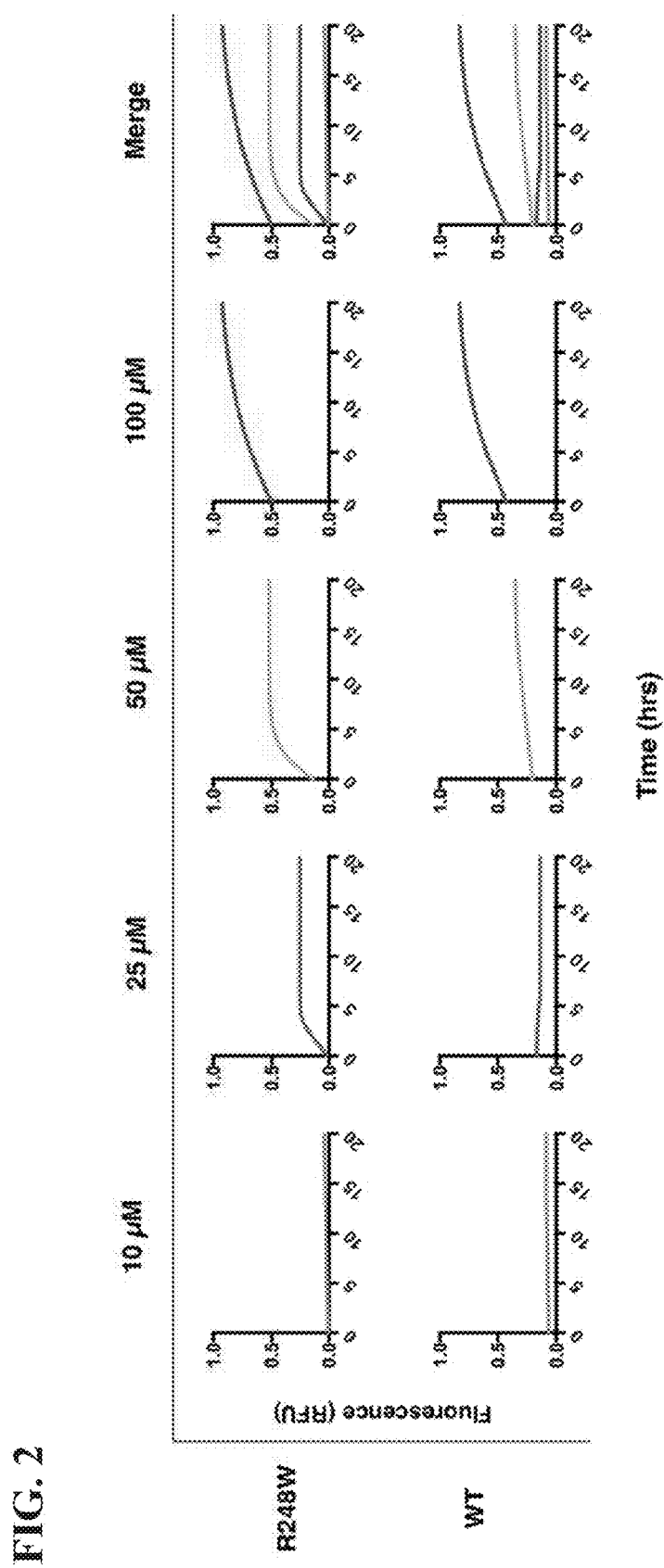
FIG. 2 shows the results of ThT kinetic assays used to assess the aggregation propensity of the R248W peptide relative to its wild-type form. These assays were performed with peptide concentrations of 10, 25, 50 and 100 µM at 37° C. The increase in fluorescence is proportional to β-sheet formation (amyloid structures).

A thioflavin T (ThT) assay was performed on both WT and R248W peptides to determine the aggregation propensity of each segment, as well as the relative secondary structure of the formed aggregates. Thioflavin T is a benzothiazole salt that fluoresces upon binding to β-sheet fibrils that are characteristic of amyloid aggregates. A sigmoidal increase in fluorescence during incubation of the peptide with ThT dye is indicative of peptide aggregation and amyloid formation. Different concentrations (10, 25, 50 and 100 µM) of the R248W peptide and its WT form were incubated with 50 µM ThT in buffer at 37° C. for 20 hours. Indeed, a concentration-dependent sigmoidal increase in fluorescence was observed with both peptides, with the R248W peptide exhibiting significantly higher fluorescence levels, as well as an accelerated aggregation propensity (FIG. 2). This suggests that the p53 WT aggregation-nucleating segment is sufficient to drive aggregation and amyloid-like formation when exposed to an aqueous environment under physiological temperature. Moreover, the augmented aggregation propensity of the R248W mutant, as shown by the relatively higher starting fluorescence point, indicates that the increased hydrophobicity of the mutant peptide acts as a destabilizing force that promotes amyloid-like aggregation. In fact, these proteins are so prone to aggregation that ThT binds mere moments from its addition to the peptide solution, indicated by the starting fluorescence point.

Figure 3A:
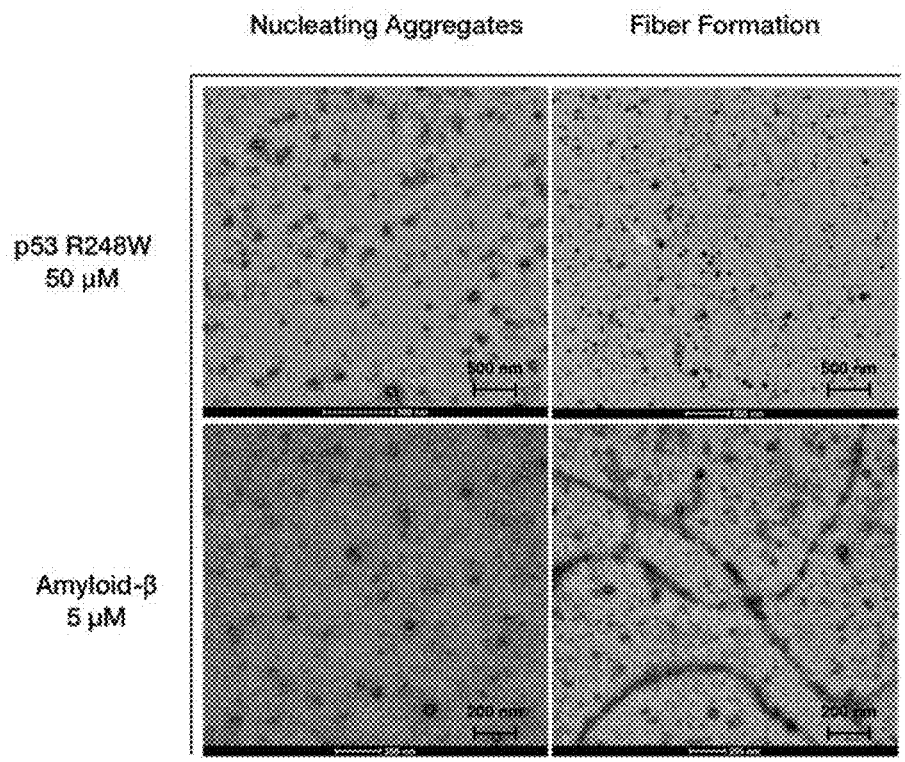
FIGS. 3A-3B show TEM Imaging of p53 R248W and Aβ aggregates.
Figure 3B:
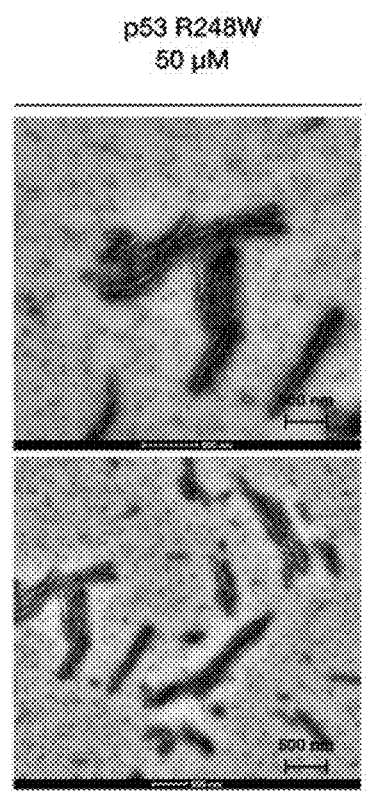

Transmission electron microscopy (TEM) was then used to visualize the R248W aggregates under similar conditions. Optimum concentrations of the R248W peptide were determined using the aforementioned ThT assay in order to obtain distinct aggregates for imaging. TEM revealed a heterogeneous collection of mutant p53 aggregates that moderately parallel the progression of amyloid formation in Amyloid-β (Aβ) (FIG. 3). Numerous small nucleating aggregates, as well as a variety of fine, flexible fibers, can be seen in the sample. These structures appear to correspond to early amyloid formation of Aβ when imaged using the same staining technique (FIG. 3A). Strikingly, several large clustered fibrils were observed that strongly point to the formation and eventual maturation of amyloid fibrils in mutant p53 aggregation (FIG. 3B).

This set of data, which includes the implementation of experiments used in typical amyloid characterization, all markedly point to the amyloid formation of R248W aggregates.

Example 3: Novel Peptide Inhibitors Derived from the p53 Aggregation-Nucleating Sequence Inhibit R248W Aggregation Two classes of peptide inhibitors were designed to abrogate mutant p53 aggregation through sequence-specific binding and charged peptide-induced repulsion (Table 2, below).

TABLE 2

Designed mutant p53 aggregation inhibitor sequences

| Peptide Name | Peptide Sequence |
|---|---|
| I254R | RRPILTRITLEDSSGNLLGRNSFEVR |
| PAS-I254R | *FFLIPKG*RRPILT<u>R</u>ITLEDSSGNLLGRNSFEVR |
| ReACp53 | RRRRRRRRRRPILT<u>R</u>ITLE |
| G3-ReACp53 | RRRRRRRRRGGGLT<u>R</u>ITLE |

Figure 4A:
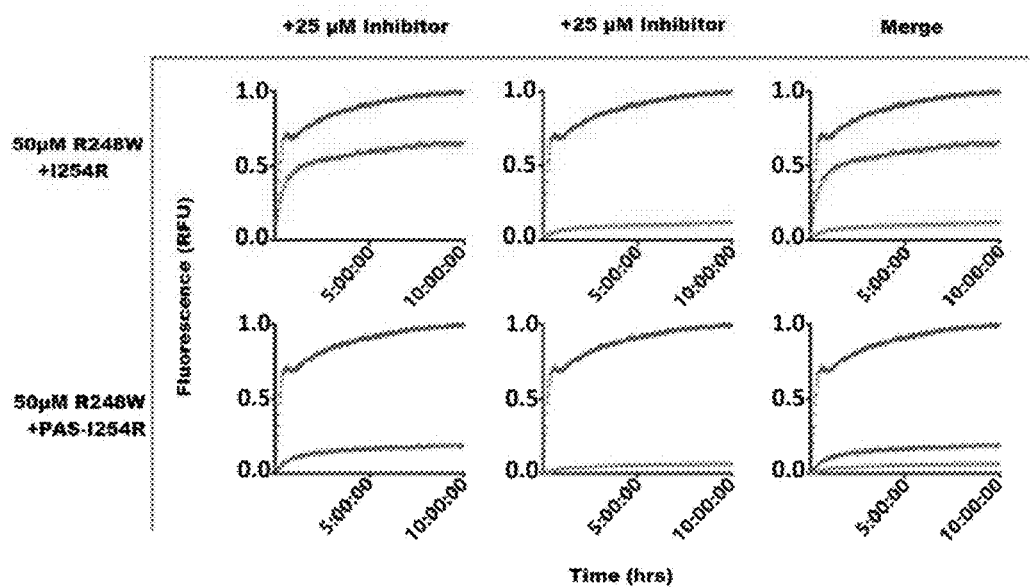
FIGS. 4A-4B show that designed peptides inhibit p53 R248W amyloid aggregation. ThT kinetic assays were used to assess the designed peptides' inhibition capability when introduced to the R248W peptide. Abrogation of aggregation is indicated by lower levels of fluorescence and delayed aggregation nucleation.
Figure 4B:
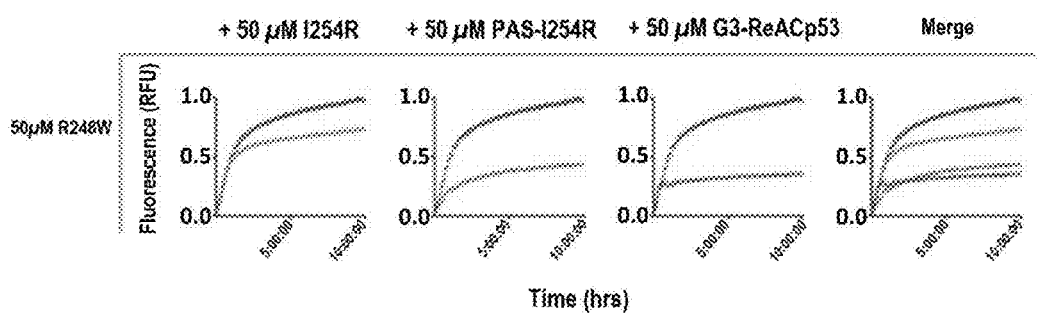

To test the inhibition efficacy of these peptides, they were subjected to a ThT assay whereby a fixed concentration of R248W was treated with varying concentrations of the respective inhibitor peptide in the presence of ThT dye and buffer. It was found that all designed inhibitors were able to inhibit mutant p53 aggregation in a concentration-dependent manner, with PAS-I254R and G3-ReACp53 being the most effective of the peptides tested (FIG. 4). Interestingly, the PAS-I254R was unexpectedly found to have comparably potent inhibition effects to the highly potent G3-ReACp53. It is hypothesized that this effect is due to the relative hydrophobicity of the PAS sequence (FFLIPKG) (FIG. 4B).

Example 4: PASylated I245R does not Abrogate Aggregation when Introduced to Pre-Formed R248W Aggregates Due to PAS-I254R's remarkable inhibition of aggregation, as observed in the initial ThT experiments, it was decided to test if this peptide also harbors the ability to abrogate pre-formed mutant p53 aggregates in order to understand its potential effect in the cancer cell environment, where mutant p53 and wild-type p53 already exist in cellular inclusions. Inhibition of pre-formed aggregates would be a crucial feature of therapeutics that successfully target mutant p53 aggregation in cancer.

Accordingly, a multi-step ThT assay was designed that would evaluate the ability of an inhibitor to abrogate aggregation at different stages of amyloid formation. Based on the sigmoidal curve produced in ThT assays of the R248W peptide, 3 time points were selected to introduce the inhibitor to mutant p53 aggregates. The first would occur at 0 mins, where no R248W aggregates would have been previously formed. The second time point would be approximately 30 mins after aggregation begins, during the exponential increase in fluorescence of the R248W ThT sigmoidal curve. The last time point would be during the plateau phase of the curve at approximately 5 hours after initiation of the assay, whereby aggregates reach an equilibrium phase and stabilize in solution.

Figure 5:
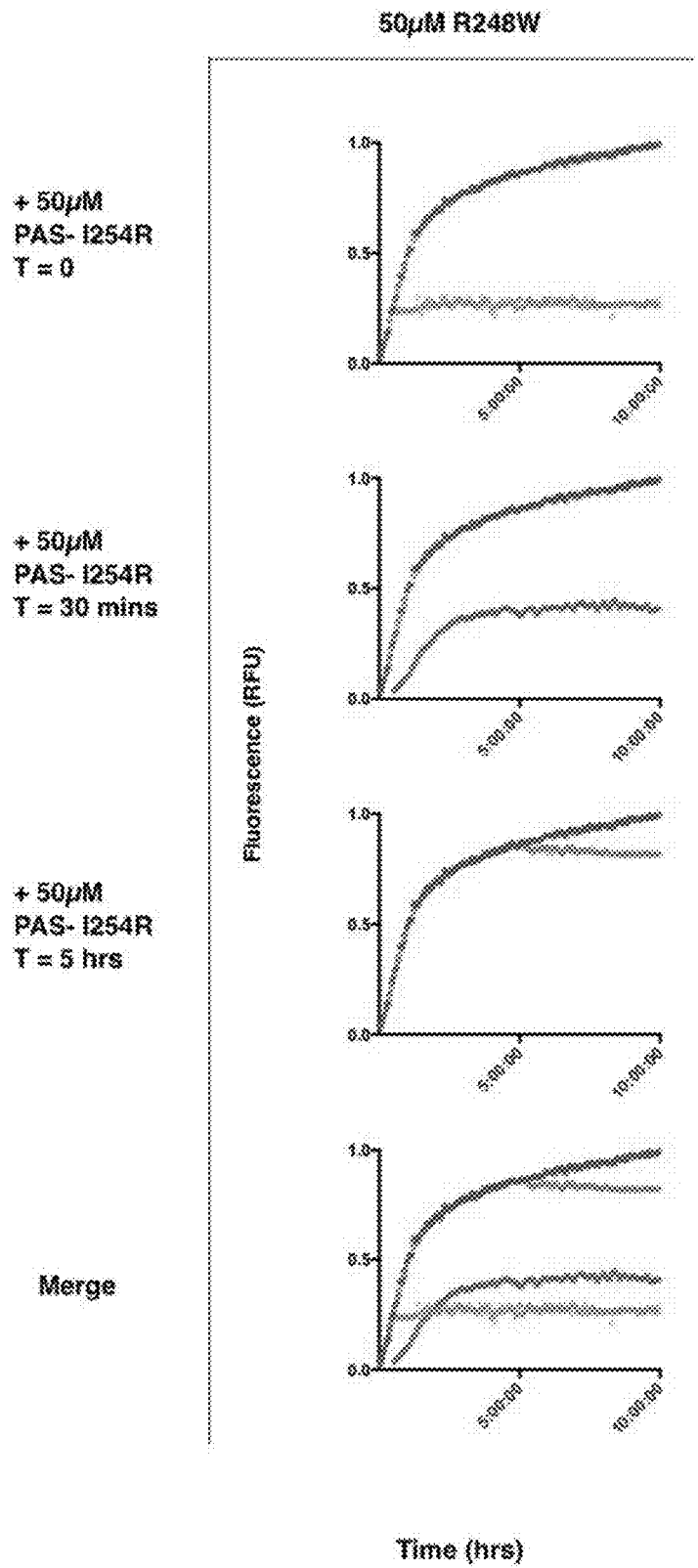
FIG. 5 shows that PASlyated I254R does not abrogate pre-aggregated R248W. A multi-step ThT kinetic assay was used to assess PAS-I254R inhibition capability when introduced to R248W in its aggregated, amyloid form. Abrogation of aggregation is indicated by lower levels of fluorescence and delayed aggregation nucleation. PAS-I254R was introduced to R248W (1:1 ratio) at three time points that correspond to different stages of amyloid formation.
Figure 6A:
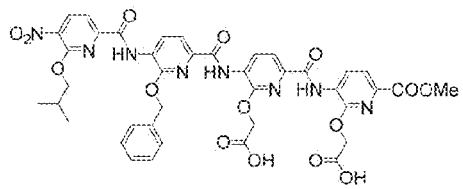
FIGS. 6A-6B demonstrate how ADH alpha-helix mimetics inhibit R245W aggregation. ThT kinetic assays were used to assess the inhibition of R248W peptide aggregation by ADH compounds.
Figure 6A:
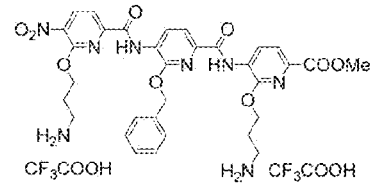
Figure 6A:
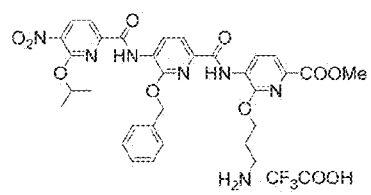
Figure 6A:
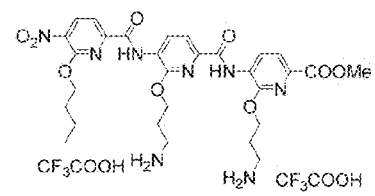
Figure 6A:
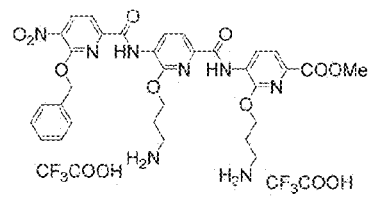
Figure 6A:
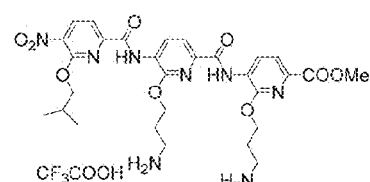
Figure 6B:
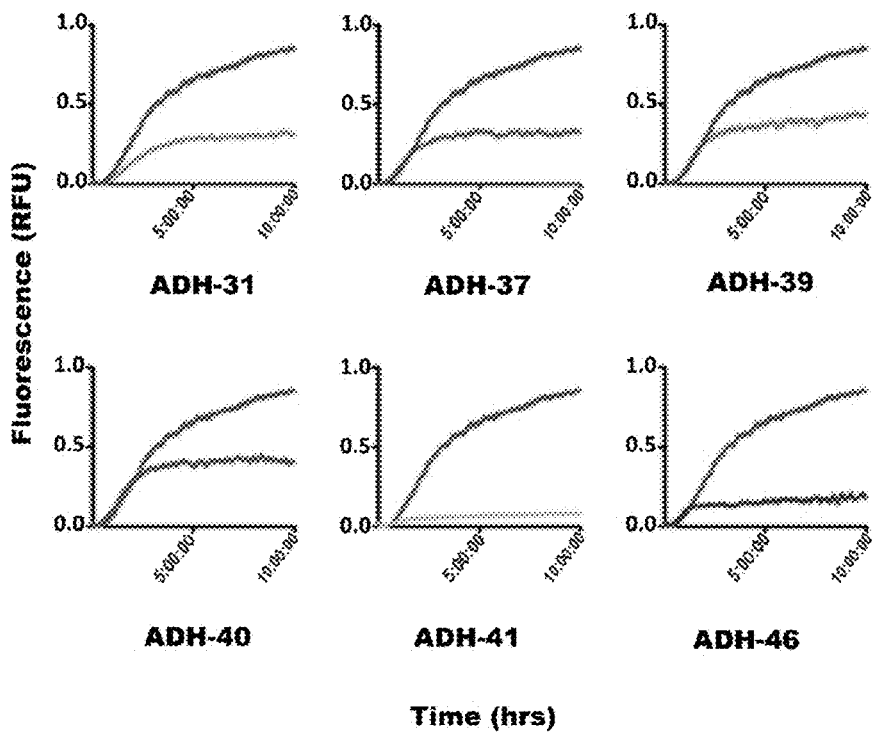

It was found that, although PAS-I254R is effective at inhibiting mutant p53 amyloid formation when co-incubated with the peptide at T=0, it is unable to abrogate aggregation after amyloid structures have formed (FIG. 5). PAS-I254R was observed to be less effective at inhibiting amyloid formation and abrogating aggregation when introduced during the exponential increase phase. Moreover, PAS-I254R was found to be only marginally effective when introduced at the plateau phase, where aggregates are assumed to have achieved a stable structure.

Example 5: Novel Hamilton Alpha-Helix Mimetic (ADH) Compounds of the Invention Inhibit Both R248W and Aβ Amyloid Formation Recently, a focused library of oligopyridylamide-based α-helix mimetics were developed by the Hamilton Lab at NYU New York (see U.S. 2018/0170910, the contents of which are incorporated by reference herein in their entirety). These compounds were shown to effectively inhibit Aβ aggregation, with one compound (ADH-41) exhibiting a marked ability at wholly suppressing Aβ amyloid formation. It has been postulated that these compounds may target an α-helical intermediate adopted by many amyloid formers and sequester amyloid formation propensity through structure-specific binding.

10 compounds based on the oligopyridylamide molecular scaffolds have been tested on mutant p53 aggregation models. A ThT assay was used to test the inhibition capability of each compound at a 1:1 ratio to the R248W mutant peptide. It has been unexpectedly found that ADH compounds 31, 37, 39, 40, 41, and 46 inhibit mutant p53 aggregation with varying levels of effectiveness (FIG. 6). Interestingly, ADH-41 was also found to be the most potent inhibitor of mutant p53 aggregation. A general trend in the efficacy of these compounds was determined to be their overall charged nature, indicating that the ADH compounds may be inhibiting mutant p53 aggregation through both structure-specific binding and hydrostatic interactions.

Example 6: ReACp53 and G3-ReACp53 Induce Cell Death in MIA PaCa-2 Cells

Figure 7A:
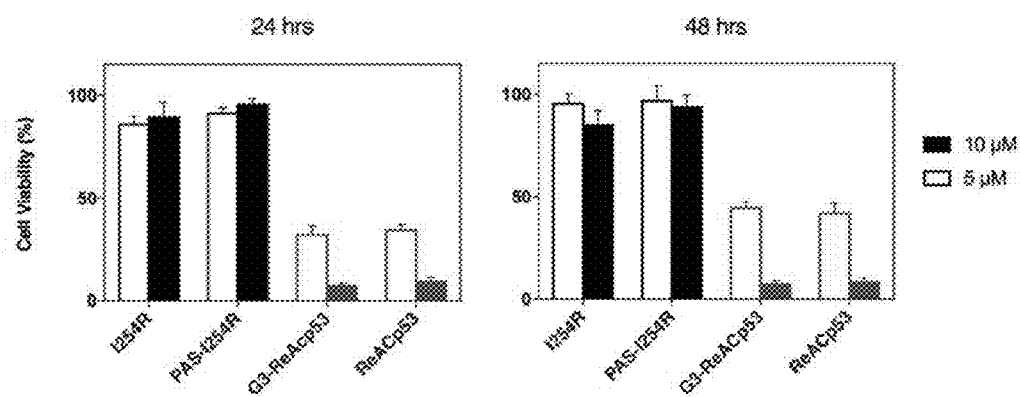
FIGS. 7A-7B show that designed peptides ReACp53 and G3-ReACp53 induce cell death in MIA PaCa-2 cells.
Figure 7B:
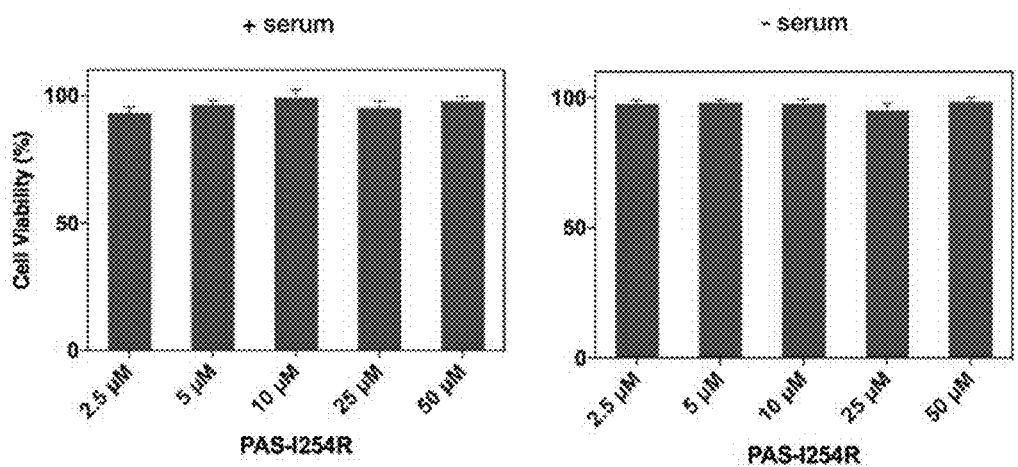

The two classes of designed peptide inhibitors have been introduced to a cancer cell-line that harbors the R248W p53 mutant, MIA PaCa-29. It has been hypothesized that upon co-localization of the inhibitors with mutant p53, mutant p53 aggregates will be abrogated, resulting in the release of wild-type p53 from cellular inclusions and, eventually, the induction of apoptosis. The 4 designed peptides were introduced to MIA PaCa-2 cells at 5 and 10 µM for 24 and 48 hour incubation periods. MTS assay was used to assess cell viability after treatment, whereby the bio-reduction of the MTS tetrazolium compound results in detectable color change that is proportional to the number of viable cells left in a sample (see Example 1). It was found that ReACp53 and G3-ReACp53 were significantly cytotoxic, while the I254R and PAS-I254R peptides failed to induce toxicity under the same conditions (FIG. 7A). PAS-I254R was also introduced to cells at higher concentrations, as well as in serum-supplemented and serum-free environments to ensure that serum interference was not preventing the peptide from entering the cell efficiently, however it still failed to induce cytotoxic effects (FIG. 7B).

Example 7: G3-ReACp53 Co-Localizes with p53 Aggregates in MIA PaCa-2 Cells

Figure 8A:
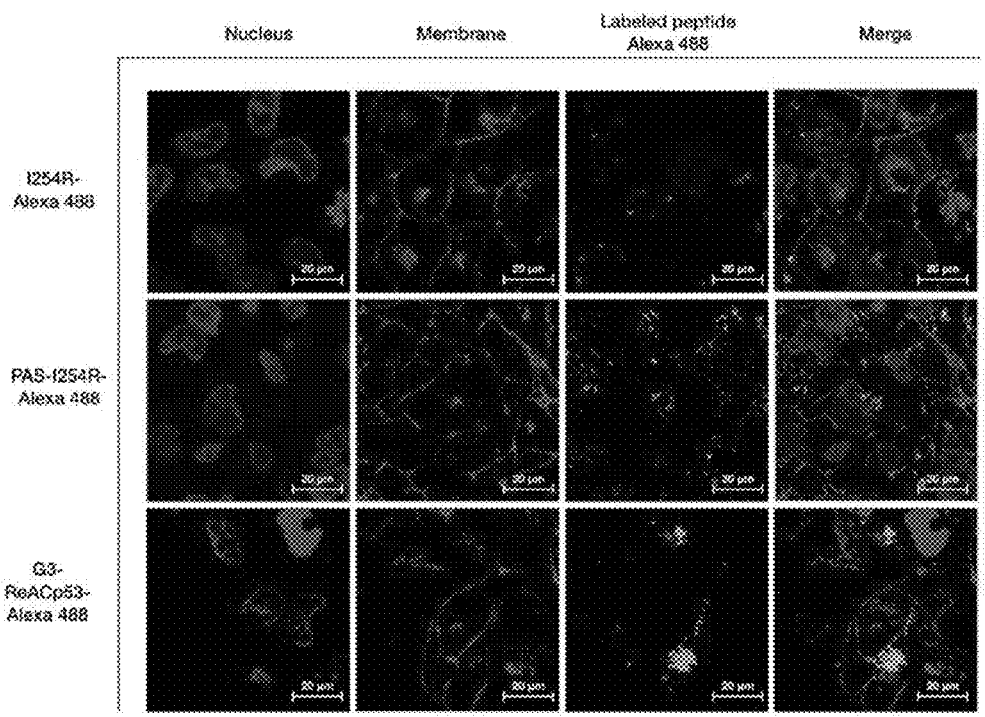
FIGS. 8A-8B depict confocal imaging of immunostained p53 and co-localization with labeled inhibitor peptides.

To visualize peptide uptake and test whether these designed peptides inhibitors co-localize with mutant p53 in the cell, the designed inhibitors were labeled with an Alexa 488 fluorescent tag and introduced them into MIA PaCa-2 cells. For the internalization analysis, 10 M of labeled peptides were introduced into live cells with an Alexa 633 labeled membrane. These cells were imaged using inverted confocal microscopy after an approximately 1 hour incubation period. Imaging confirms that all peptides are readily internalized by the cells, however the internalization of G3-ReAcp53 and PAS-I254R appeared, visually, to be much greater when compared to the I254R peptide (FIG. 8A).

Figure 8B:
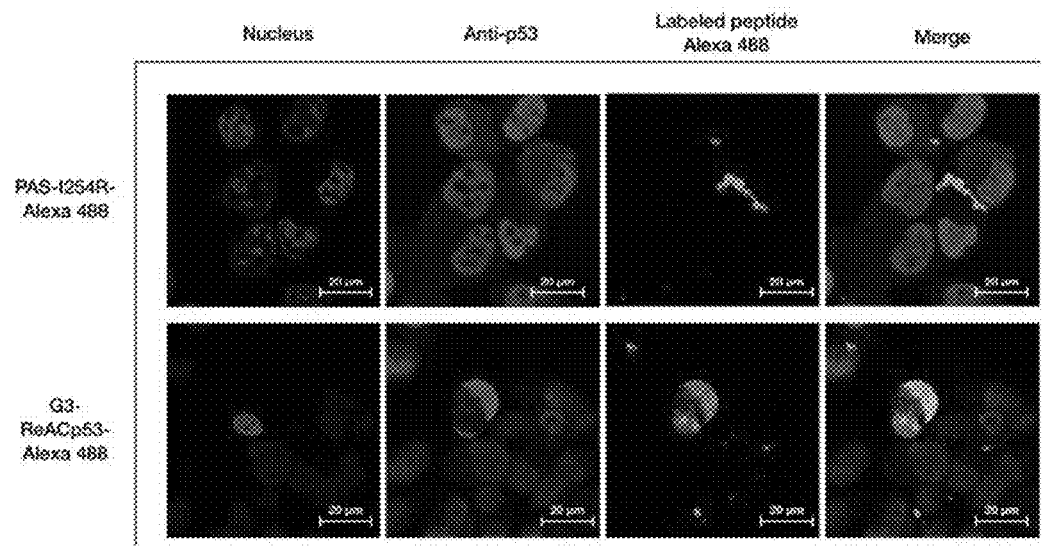

For the co-localization assay, mutant p53 was immunostained using a p53 antibody (FL-393) that recognizes amino acid residues 1-393, representing the full-length p53 protein—both mutant and wild-type forms. A Texas Red secondary antibody was used for its fluorescence detection. Co-localization was visible between the G3-ReACp53-Alexa 488 labeled peptide and the mutant p53 antibody, however there was little to no co-localization observed with the labeled PAS-I254R (FIG. 8B). This observation is in congruence with PAS-I254R's non-toxic effects on MIA PaCa-2 cells and the peptide's inability to abrogate preformed amyloid structures. Because PAS-I254R cannot fully co-localize to these structures, it loses its ability to abrogate aggregation, thus rendering it ineffective in restoring wild-type p53 function. Moreover, G3-ReACp53's ability to co-localize to mutant p53 aggregates and induce cell death can be attributed to its relatively more flexible and highly charged nature, allowing sequence-specific binding to occur readily in the cellular environment and initiate abrogation of aggregates 12. PAS-I254R's additional hydrophobic sequence prevents it from interacting with the hydrophobic residues that initiate aggregation in mutant p53.

Example 8: ADH Compounds Selectively Induce Cell Death in a R248W Mutant p53 Cell Line It has presently been shown that novel sequence-specific inhibitors have the capacity to not only inhibit R248W aggregation in solution, but also induce cell death in a R248W cancer model. The model of p53 rescue has further been expanded to structure-specific inhibitors, such as the ADH alpha-helix mimetics; these newly developed compounds have been shown to inhibit both mutant p53 aggregation and Aβ fibrillation. MIA PaCa-2 cells were incubated with ADH compounds 17, 27, 31, 37, 39, 40, 41, 45, 46, and 52 (5 and 10 μM) for 24 and 48 hours. Cell viability was determined using the MTS assay.

Figure 9A:
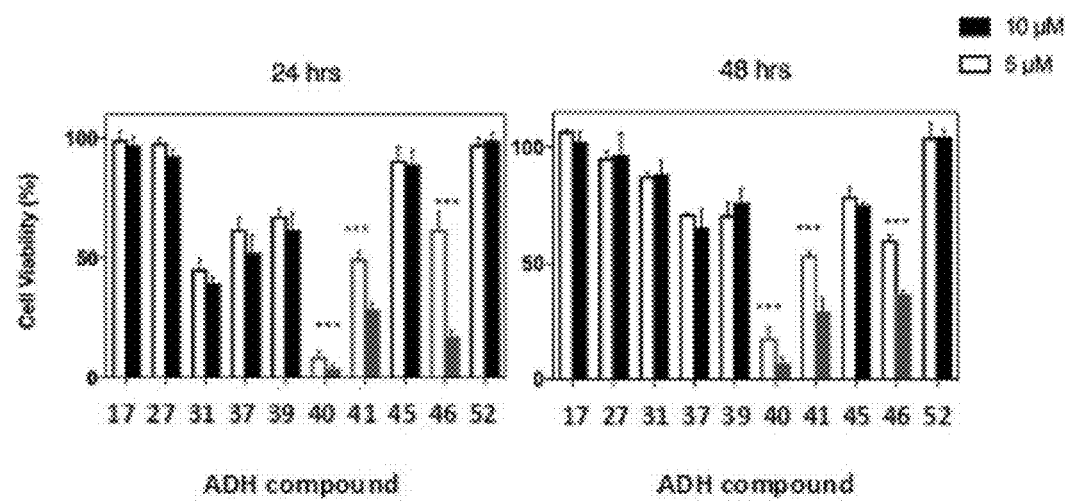
FIGS. 9A-9B show that designed peptides ReACp53 and G3-ReACp53 induce cell death in MIA PaCa-2 cells.

Surprisingly, it was found that ADH-40, 41 and 46 had an extremely significant effect on cell viability, with ADH-40 boasting a level of toxicity greater than 90%, making it the most effective inhibitor of all those tested in this study (FIG. 9A). Notably, this is the first use of a bona fide amyloid inhibitor as a potent cancer therapeutic.

Figure 9B:
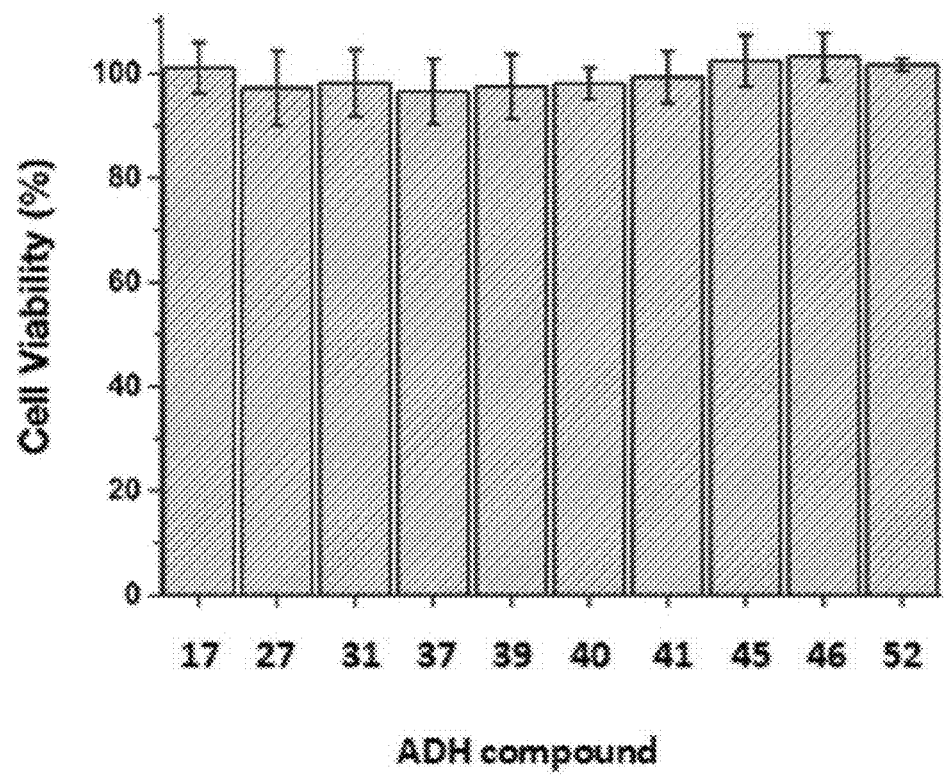

Additionally, these inhibitors appear to have no toxic effect on cell-lines with wild-type p53 (FIG. 9B). Mouse Neuroblastoma cells (N2a), which contain wild-type p53, were incubated with ADH compounds (5 μM) for 24 hours. No toxicity was observed, suggesting that these compounds undergo structure-specific binding and target mutant p53 segments, thereby abrogating aggregation and effectively restoring p53 tumor suppressor function.

Figure 10:
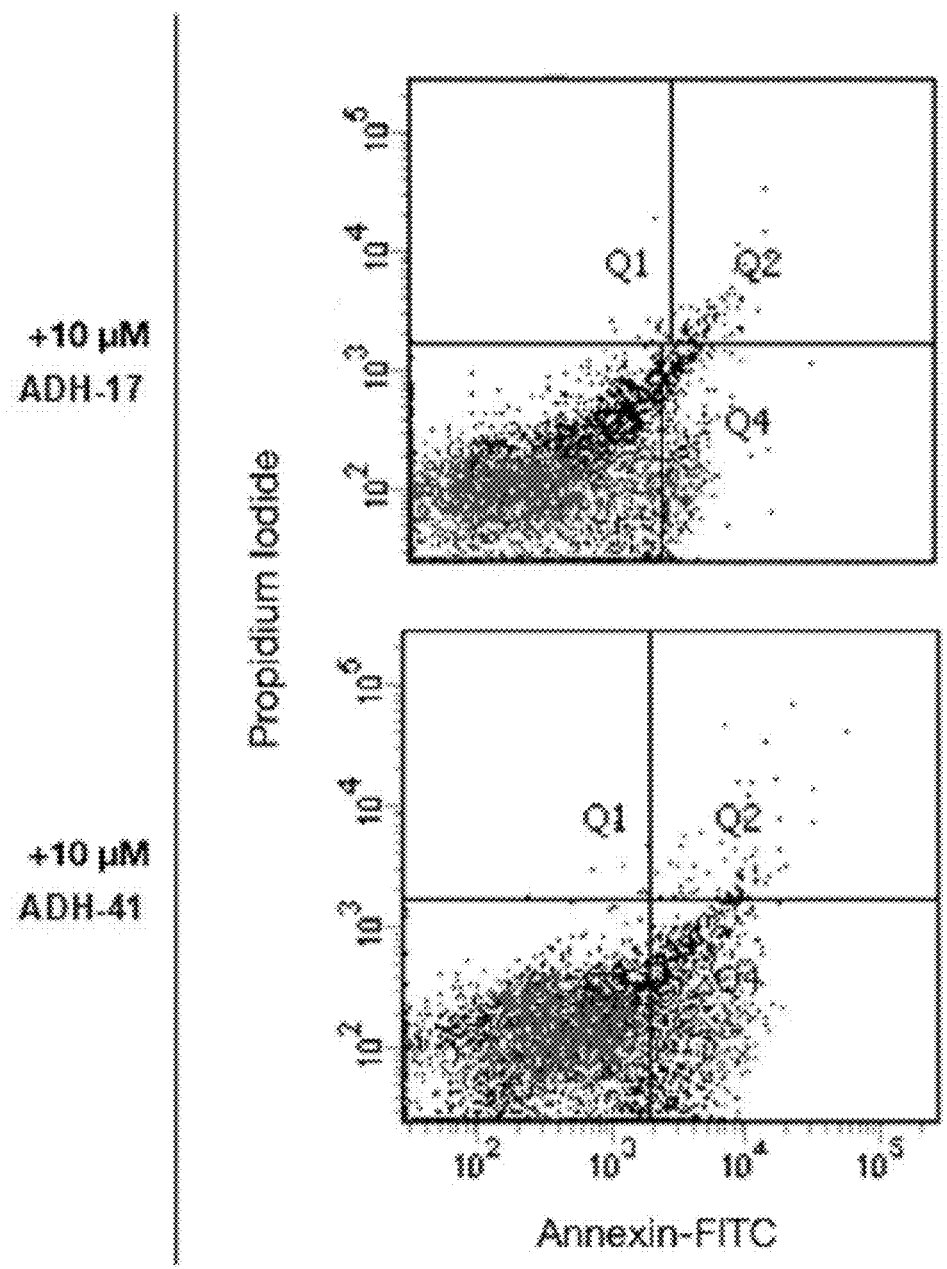
FIG. 10 shows ADH-41 effect to induce apoptotic cell death in MIA-PaCa-2 cells. An annexin/PI fluorescence-activated cell sorting protocol was implemented to determine if ADH-41 induces cell death though apoptosis. ADH-17 was used as a control due to its non-toxic effects on MIA PaCa-2. ADH-17 and 41 were incubated with cells for 24 hours prior to sample preparation. The cell population shift towards Q2 and Q4 indicate late and early apoptotic cell death, respectively.
Figure 11:
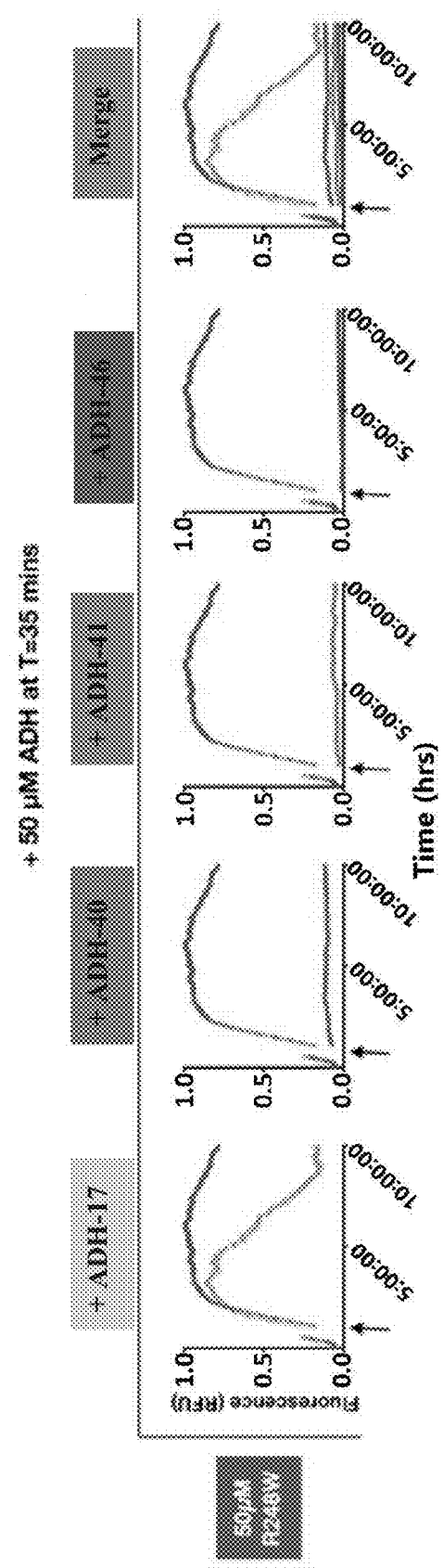
FIG. 11 shows that ADH compounds according to the invention abrogate R248W aggregates after elongation phase of amyloid formation. A multi-step ThT kinetic assay was used to assess the ADH compounds' capability to abrogate aggregates at the elongation phase of amyloid formation (T=35 mins). Abrogation of aggregation is indicated by lower levels of fluorescence. ADH-17 was used as a negative control. ADH compounds were introduced at a 1:1 ratio to R248W peptides after allowing the peptide to aggregate for 35 mins at 37° C. Arrows indicate addition time. The same compounds that induce toxicity in a mutant p53 (R248W) cell line also abrogate aggregation at the elongation phase (ADH-40, 41 and 46), indicating that these compounds can target aggregates after their formation.
Figure 12:
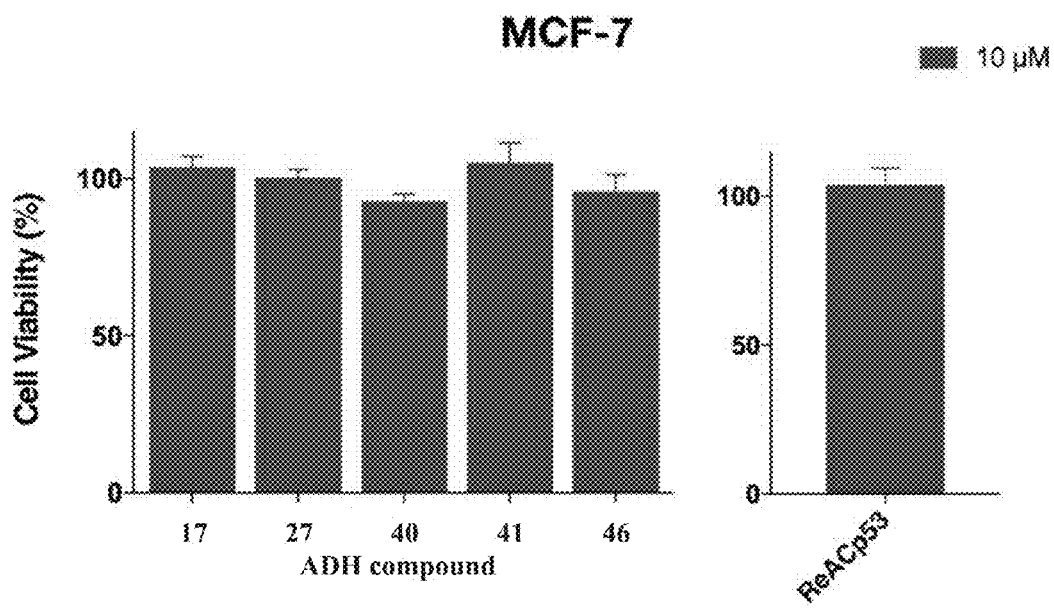
FIG. 12 shows that ADH compounds according to the invention and ReACp53 show no significant toxicity in WT p53 cell lines. MCF-7 and COS-7 cells were incubated with M of ADH 17, 27, 40, 41 and 46, as well as ReACp53, in serum-free media for 24 hours. No significant toxicity was observed. Cell viability was measured using the MTS assay (MCF-7: n=2; COS-7: n=3)
Figure 12:
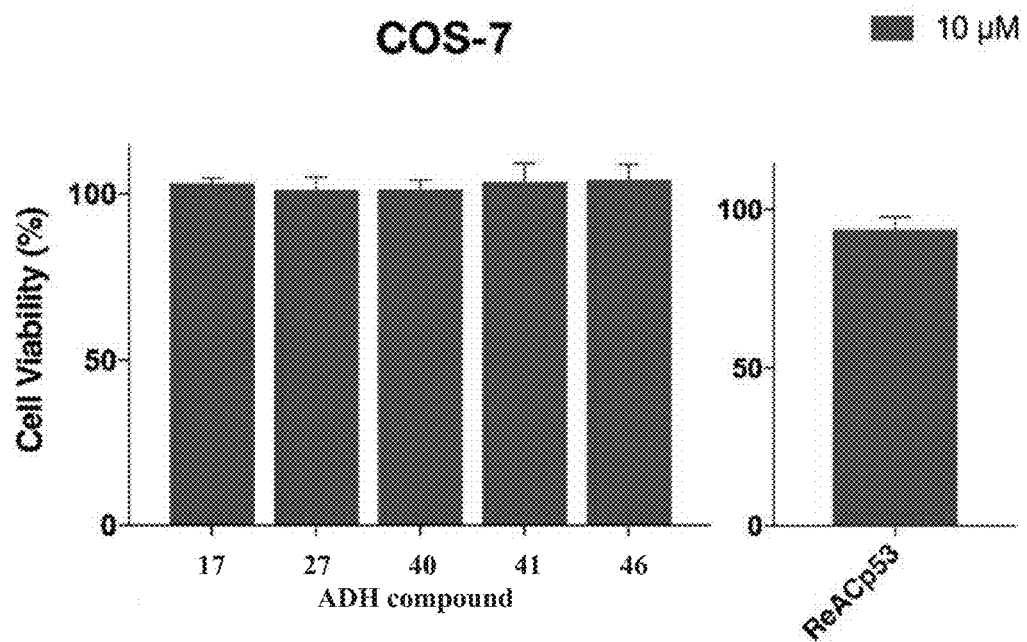
Figure 13A:
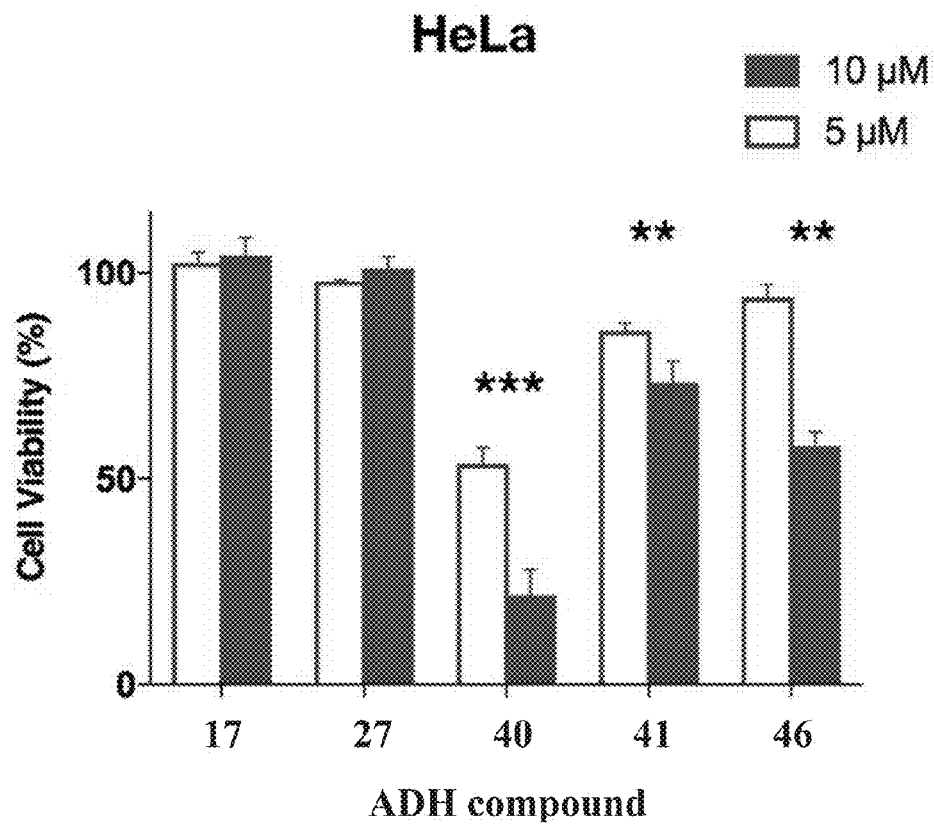
FIGS. 13A-13B show that ADH compounds according to the invention and ReACp53 induce significant toxicity in HeLa cells. HeLa cells were incubated with 5 or 10 µM of ADH 17, 27, 40, 41 and 46 in serum-free media for 24 hours.
Figure 13B:
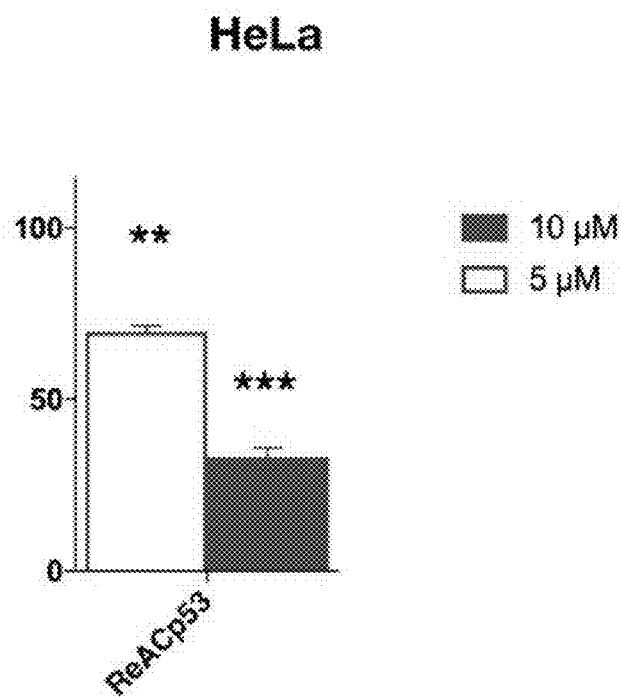

Example 9: Preliminary Annexin/PI FACS Data Suggest that ADH-41 Induces Apoptosis in a MIA PaCa-2 Cells It has been hypothesized that the cell death observed upon treatment of these inhibitors is brought about by p53-mediated apoptosis. Inhibitors rescue p53 function from mutant-initiated sequestration and allow the cell to undergo normal apoptosis. Hence, an Annexin/PI Fluorescence-activated cell sorting protocol was implemented to determine the level of apoptosis induced upon treating MIA PaCa-2 cells with these designed inhibitors. This assay allows the detection of cell populations undergoing apoptosis through fluorescent annexin labeling of phosphatidylserine (PS), a phospholipid that becomes exposed on the outer membrane of a mammalian cell undergoing apoptosis. A second fluorescent label, Propidium Iodide (PI) stains DNA in dead cells, allowing for the differentiation between apoptotic and necrotic cells. Preliminary data suggests an increase in apoptosis after 24 hour incubation with the compound (FIG. 10).

Example 10: ADH Compounds 40, 41 and 46 Abrogate R248W Aggregates Past the Elongation Phase of Amyloid Formation In order to target p53 aggregation in the cellular environment, the ADH compounds according to the invention would need to bind and abrogate pre-formed p53 aggregates, as well as prevent additional aggregation. Inhibition of pre-formed aggregates would be a crucial feature of therapeutics that successfully target mutant p53 aggregation in cancer. Using the multi-step thioflavin T assay, where the inhibitor is added to R248W at either elongation or the plateau phases of amyloid formation, 50 μM of the R248W peptide was incubated at 37° C. for 35 minutes before adding an equimolar ratio of the ADH compound (FIG. 1). ADH-40, 41 and 46 were found to be able to target and abrogate aggregates at the elongation phase, indicated by the sharp decrease in fluorescence after the addition of the compound.

Example 11: ADH Compounds do not Induce Significant Toxicity in Wild-Type p53 Cell Lines MCF-7 and COS-7

It has been shown that the ADH compounds have no toxic effect on N2a cells, which carry wild-type p53. Their effect on other wild-type p53 cell lines: MCF-7 and COS-7 was further investigated. Cells were incubated with ADH compounds 17, 27, 40, 41 and 46 for 24 hours at 5 and 10 μM in serum-free media before determining cell viability via MTS (FIG. 2). The results show that the compounds do not induce significant toxicity in these cells, further indicating that they preserve the function of wild-type p53 in cells where its function is not compromised.

Additionally, a recently developed peptide that targets p53 aggregation, called ReACp53, does not appear to induce toxicity in these cells under the same conditions.

Example 12: ADH Compounds Induce Marked Toxicity in HeLa Cells

It has been surprisingly and unexpectedly found that ADH compounds 40, 41, and 46 are significantly toxic to HeLa cells (FIG. 3A). It has been hypothesized that the ADH compounds may bind to wild-type p53 in a manner that preserves its main function, yet disrupts other protein-protein interactions in the cellular environment. HeLa cells are known to have very low p53 expression levels, which is attributed to the expression of the HPV-E6 protein. E6 proteins target p53 for proteasomal degradation via the ubiquitin pathway by binding to p53's core domain (residues 94-292) and C-terminus. Because it has been hypothesized that the effective ADH compounds (40, 41, and 46) target the p53 DNA-binding domain located in its core region, the compounds may prevent E6 binding, leading to p53 accumulation and eventually apoptosis. Notably, ReACp53 was also found to be significantly toxic to HeLa cells (FIG. 3B). Since ReACp53 is a sequence-specific peptide that targets the p53 DNA-binding domain, it may also prevent E6 binding through a similar mechanism. Other small molecule inhibitors of the E6-p53 interaction have been previously described such as RITA (2,5-bis-(5-hydroxymethyl-2-thienyl) furan), which binds to wild-type p53 and prevents its interaction with E6 in HeLa cells.

Not only does this result further enable to decipher the ADH binding-site on the p53 protein, but it may also indicate that these ADH compounds have therapeutic potential beyond that of mutant p53 cancers, such as HPV-related cancers.

REFERENCES

1. Rangel, L. P., Costa, D. C., Vieira, T. C., & Silva, J. L. (2014). The aggregation of mutant p53 produces prion-like properties in cancer. Prion 8:1, 75-84.
2. Willis A, Jung E J, Wakefield T, & Chen X (2004). Mutant p53 exerts a dominant negative effect by preventing wild-type p53 from binding to the promoter of its target genes. Oncogene 23(13):2330-2338.
3. Maslon, M. M. & Hupp, T. R. (2010) Drug discovery and mutant p53. Trends Cell Biol. 20, 542-555.
4. Soragni, A., Janzen, D. M., Johnson, L. M., Lindgren, A. G., Nguyen, A. T. Q., Tiourin, E., . . . & Pellegrini, M. (2016). A designed inhibitor of p53 aggregation rescues p53 tumor suppression in ovarian carcinomas. Cancer cell, 29(1), 90-103.
5. Rahib, L., Smith, B. D., Aizenberg, R., Rosenzweig, A. B., Fleshman, J. M., & Matrisian, L. M. (2014). Projecting cancer incidence and deaths to 2030: the unexpected burden of thyroid, liver, and pancreas cancers in the United States. Cancer research, 74(11), 2913-2921.
6. Xu J (2011) Gain of function of mutant p53 by coaggregation with multiple tumor suppressors. Nature Chemical Biology 7:285-295
7. Schlapschy, M., Binder, U., Borger, C., Theobald, I., Wachinger, K., Kisling, S., & Skerra, A. (2013). PASylation: a biological alternative to PEGylation for extending the plasma half-life of pharmaceutically active proteins. Protein Engineering Design and Selection, 26(8), 489-501.
8. Kumar, S., & Hamilton, A. D. (2017). α-Helix Mimetics as Modulators of Aβ Self-Assembly. Journal of the American Chemical Society, 139(16), 5744-5755.
9. Lindberg, D. J., Wenger, A., Sundin, E., Wesén, E., Westerlund, F., & Esbjörner, E. K. (2017). Thioflavin-T binding to amyloid fibrils leads to fluorescence self-quenching and fibril compaction. Biochemistry.
10. Riss, T. L., Moravec, R. A., Niles, A. L., Duellman, S., Benink, H. A., Worzella, T. J., & Minor, L. (2016). Cell viability assays.
11. Love, I. M., Shi, D., & Grossman, S. R. (2013). p53 Ubiquitination and proteasomal degradation. p53 Protocols, 63-73.
12. Cummings C G & Hamilton A D (2010) Disrupting protein-protein interactions with non-peptidic, small molecule α-helix mimetics. Current opinion in chemical biology 14(3):341-346.
13. Sidhar, H., & Giri, R. K. (2017). Induction of Bex genes by curcumin is associated with apoptosis and activation of p53 in N2a neuroblastoma cells. Scientific Reports, 7.
14. Rieger, A. M., & Barreda, D. R. (2016). Accurate assessment of cell death by imaging flow cytometry. Imaging Flow Cytometry: Methods and Protocols, 209-220.
15. Qin, Y., Ma, Z., Dang, X., Li, W. E. I., & Ma, Q. (2014). Effect of resveratrol on proliferation and apoptosis of human pancreatic cancer MIA PaCa-2 cells may involve inhibition of the Hedgehog signaling pathway. Molecular medicine reports, 10(5), 2563-2567.
16. Vogiatzi F, et al. (2016) Mutant p53 promotes tumor progression and metastasis by the endoplasmic reticulum UDPase ENTPD5. *Proceedings of the National Academy of Sciences* 113(52):E8433-E8442.
17. Svensen N, Walton J G, & Bradley M (2012) Peptides for cell-selective drug delivery. Trends in pharmacological sciences 33(4):186-192.
18. Wang, G., & Fersht, A. R. (2017). Multisite aggregation of p53 and implications for drug rescue. Proceedings of the National Academy of Sciences, 201700308.
19. Gannon, J. V., Greaves, R., Iggo, R. & Lane, D. P. Activating mutations in p53 produce a common conformational effect. A monoclonal antibody specific for the mutant form. EMBO J. 9, 1595-1602 (1990).
20. Gura, T. (2008). Hope in Alzheimer's fight emerges from unexpected places. Nature medicine, 14(9), 894-894.
21. Jayatunga M K P, Thompson S, & Hamilton A D (2014) α-Helix mimetics: Outwards and upwards. Bioorganic & Medicinal Chemistry Letters 24(3):717-724.
22. Landers J E, Cassel S L, & George D L (1997) Translational Enhancement of mdm2 Oncogene Expression in Human Tumor Cells Containing a Stabilized Wild-Type p53 Protein. Cancer Research 57(16):3562-3568.
23. Oda K, et al. (2000) p53AIP1, a Potential Mediator of p53-Dependent Apoptosis, and Its Regulation by Ser-46-Phosphorylated p53. Cell 102(6):849-862.
24. Villa L L (1997) Human papillomaviruses and cervical cancer. Advances in cancer research 71:321-341.
25. Martinez-Zapien D, et al. (2016) Structure of the E6/E6AP/p53 complex required for HPV-mediated degradation of p53. Nature 529(7587):541-545.
26. Wade M, Li Y-C, & Wahl G M (2013) MDM2, MDMX and p53 in oncogenesis and cancer therapy. Nature reviews. Cancer 13(2):83.
27. Zhao C Y, Szekely L, Bao W, & Selivanova G (2010) Rescue of p53 Function by Small-Molecule RITA in Cervical Carcinoma by Blocking E6-Mediated Degradation. Cancer Research 70(8):3372-3381.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:
1. A method of inhibiting aggregation of a p53 protein comprising contacting said p53 protein with an effective amount of a compound of formula (I):

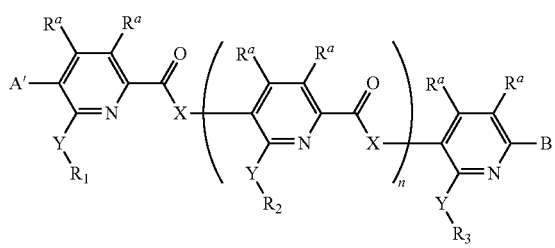

(I)

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_3$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

A is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl;

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; $C_1$-$C_8$ perfluorocarbon; an aliphatic $C_1$-$C_{12}$ hydrocarbon; an aromatic $C_1$-$C_{12}$ hydrocarbon; and a $C_1$-$C_{12}$ heteroaryl;

R* is independently selected at each occurrence from hydrogen or $C_1$-$C_{12}$ hydrocarbons each of which optionally contains 1-8 heteroatoms selected from halogen, O, N, and S and combinations thereof; and n is an integer from 0 to 2;

with the proviso that (i) when n is 0, and Y is O, $R_1$ and $R_3$ are not both —CH$_2$CO$_2$H; (ii) when n is 1, Y is O, and $R_1$ and $R_3$ are both —CH$_2$CO$_2$H, $R_2$ is not —CH$_2$CO$_2$H or a straight chained, branched or cyclic aliphatic or aryl $C_1$-$C_{12}$ hydrocarbon, or $R_2$ does not have the structure —C(CH$_2$CO$_2$H)$_3$; (iii) when n is 1, and Y is O, $R_1$ through $R_3$ are not each an unsubstituted $C_1$-$C_8$ hydrocarbon; and (iv) when n is 2, and Y is O, $R_1$ through $R_3$ are not —CH$_2$CO$_2$H at all occurrences, or a pharmaceutically acceptable salt thereof.

2. The method of claim 1, wherein the p53 protein comprises one or more mutations.

3. The method of claim 2, wherein the p53 protein comprises R248W mutation.

4. The method of claim 1, wherein the p53 protein is in a cell.

5. The method of claim 4, wherein the cell is in a subject.

6. The method of claim 1, wherein the compound has the structure according to formula (II):

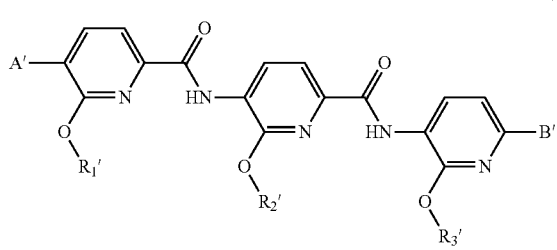

(II)

wherein $R_1'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof;

$R_2'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof;

$R_3'$ is selected from a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3^+$; —(C=O)—R*; —CHO; —CO$_2$H; —CO$_2$R*; —(C=O)—S—R*; —O—(C=O)—H; —O—(C=O)—R*; and combinations thereof;

A' is selected from —NO$_2$; —NH$_2$; —NHR*; —N(R*)—(C=O)—R*, —N(R*)$_2$, where R* is hydrogen or an aliphatic $C_1$-$C_{12}$ hydrocarbon; and B' is selected from —(C=O)—R*; —CO$_2$H; —CO$_2$R*, where R* is hydrogen or an aliphatic $C_1$-$C_{12}$ hydrocarbon;

R* is independently selected at each occurrence from hydrogen or $C_1$-$C_{12}$ hydrocarbons each of which optionally contains 1-8 heteroatoms selected from halogen, O, N, and S and combinations thereof;

with the proviso that (i) when $R_1$ and $R_3$ are both —CH$_2$CO$_2$H, $R_2$ is not —CH$_2$CO$_2$H or a straight chained, branched or cyclic aliphatic $C_1$-$C_{12}$ hydrocarbon, or $R_2$ does not have the structure —C[CH$_2$CO$_2$H]$_3$; and (ii) $R_1$ through $R_3$ are not each an unsubstituted $C_1$-$C_8$ hydrocarbon, or a pharmaceutically acceptable salt thereof.

7. The method of claim 1, wherein the compound has the structure according to the following formula:

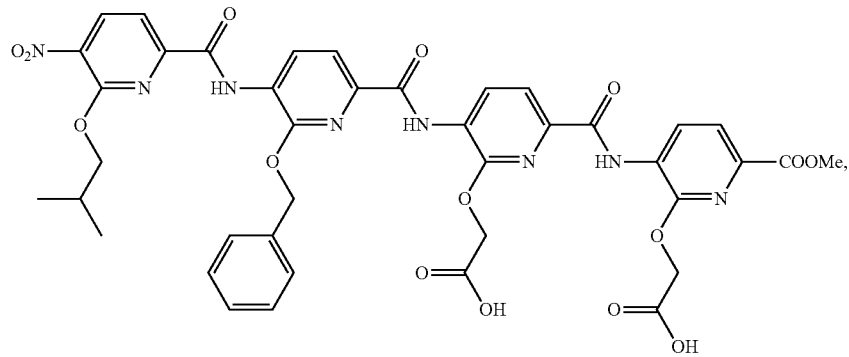 [SMILES: COC(=O)c1ccc(NC(=O)c2ccc(NC(=O)c3ccc(NC(=O)c4ccc([N+](=O)[O-])c(OCC(C)C)n4)c(OCc4ccccc4)n3)c(OCC(=O)O)n2)c(OCC(=O)O)n1]

or a pharmaceutically acceptable salt thereof.

8. The method of claim 1, wherein the compound has the structure according to the following formula:

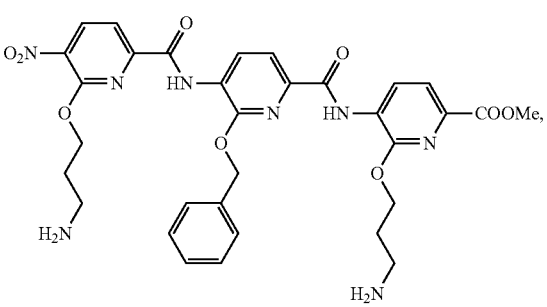 [SMILES: COC(=O)c1ccc(NC(=O)c2ccc(NC(=O)c3ccc([N+](=O)[O-])c(OCCCN)n3)c(OCc3ccccc3)n2)c(OCCCN)n1]

or a pharmaceutically acceptable salt thereof.

9. The method of claim 1, wherein the compound has the structure according to the following formula:

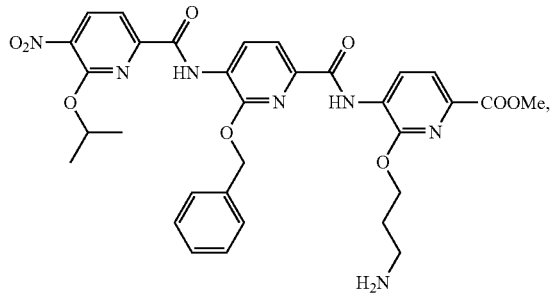 [SMILES: COC(=O)c1ccc(NC(=O)c2ccc(NC(=O)c3ccc([N+](=O)[O-])c(OC(C)C)n3)c(OCc3ccccc3)n2)c(OCCCN)n1]

or a pharmaceutically acceptable salt thereof.

10. The method of claim 1, wherein the compound has the structure according to the following formula:

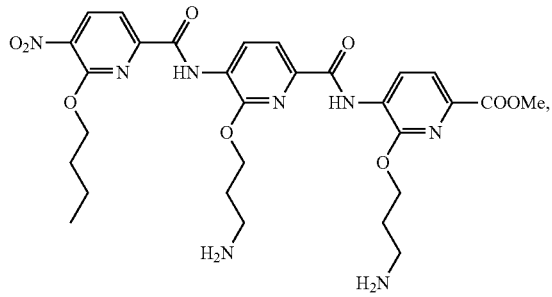 [SMILES: CCCCOc1nc(C(=O)Nc2ccc(C(=O)Nc3ccc(C(=O)OC)nc3OCCCN)nc2OCCCN)ccc1[N+](=O)[O-]]

or a pharmaceutically acceptable salt thereof.

11. The method of claim 1, wherein the compound has the structure according to the following formula:

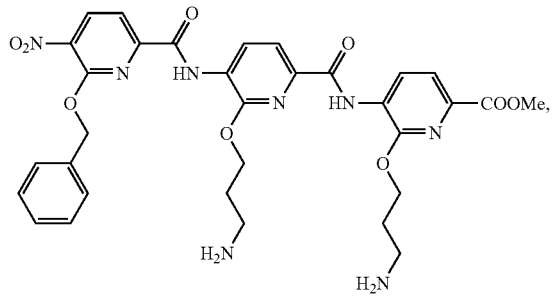 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

12. The method of claim 1, wherein the compound has the structure according to the following formula:

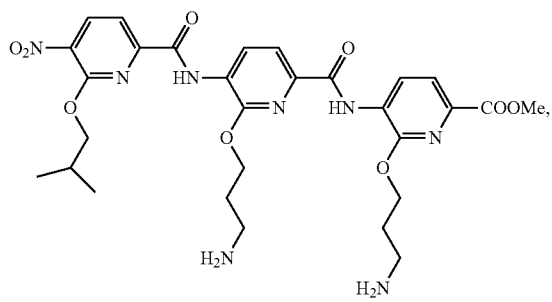 [SMILES: COC(=O)c1ccc(NC(=O)c2ccc(NC(=O)c3ccc([N+](=O)[O-])c(OCC(C)C)n3)c(OCCCN)n2)c(OCCCN)n1]

or a pharmaceutically acceptable salt thereof.

13. A method of treating a cancer associated with aggregation of a p53 protein in a subject in need of such treatment, wherein the cancer is associated with one or more p53 mutations, comprising administering to said subject an effective amount of a compound of formula (I):

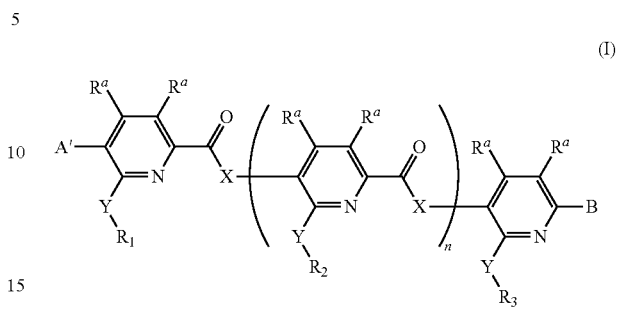

wherein $R^a$ is independently selected at each occurrence from hydrogen, $C_1$-$C_{12}$ hydrocarbons, —F; —Cl; —Br; —I; —OH, —OR*; —NO; —NO$_2$; —NO$_3$; —O—NO; —N$_3$; —NH$_2$; —NHR*; and —N(R*)$_2$;

X is independently at each occurrence selected from —O—; —S—; —NH—; —NR*—; and —C(R*)$_2$;

Y is independently at each occurrence selected from —O—; —S—; —NH—; and —NR*—;

$R_1$ is selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

$R_2$ is independently at each occurrence selected from hydrogen or a straight chained, branched or cyclic aliphatic $C_1$-$C_{20}$ hydrocarbon; an aromatic $C_6$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, a $C_1$-$C_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$;

—S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

R$_3$ is selected from hydrogen or a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$ and combinations thereof;

A is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl;

B is selected from hydrogen, —F; —Cl; —Br; —I; —OH, —OR*; —NO; —NO$_2$; —NO$_3$; —O—NO; —N$_3$; —NH$_2$; —NHR*; —N(R*)$_2$; —N(R*)$_3$$^+$; —N(R*)—OH; —O—N(R*)$_2$; —N(R*)—O—R*; —CN; —NC; —(C=O)—R*; —CHO; —CO$_2$H; —CO$_2$R*; —(C=O)—S—R*; —O—(C=O)—H; —O—(C=O)—R*; —S—(C=O)—R*; —(C=O)—NH$_2$; —(C=O)—N(R*)$_2$; —(C=O)—NHNH$_2$; —O—(C=O)—NHNH$_2$; —(C=S)—NH$_2$; —(C=S)—N(R*)$_2$; —N(R*)—CHO; —N(R*)—(C=O)—R*; —SCN; —NCS; —NSO; —SSR*; —SO$_2$R*; —SO$_2$—N(R*)$_2$; —S(=O)—OR*; —S(=O)—R*; —Si(R*)$_3$; —CF$_3$; —O—CF$_3$; —P(R*)$_2$; —O—P(=O)(OR*)$_2$; —P(=O)(OR*)$_2$; C$_1$-C$_8$ perfluorocarbon; an aliphatic C$_1$-C$_{12}$ hydrocarbon; an aromatic C$_1$-C$_{12}$ hydrocarbon; and a C$_1$-C$_{12}$ heteroaryl;

R* is independently selected at each occurrence from hydrogen or C$_1$-C$_{12}$ hydrocarbons each of which optionally contains 1-8 heteroatoms selected from halogen, O, N, and S and combinations thereof; and n is an integer from 0 to 2;

with the proviso that (i) when n is 0, and Y is O, R$_1$ and R$_3$ are not both —CH$_2$CO$_2$H; (ii) when n is 1, Y is O, and R$_1$ and R$_3$ are both —CH$_2$CO$_2$H, R$_2$ is not —CH$_2$CO$_2$H or a straight chained, branched or cyclic aliphatic or aryl C$_1$-C$_{12}$ hydrocarbon, or R$_2$ does not have the structure —C(CH$_2$CO$_2$H)$_3$; (iii) when n is 1, and Y is O, R$_1$ through R$_3$ are not each an unsubstituted C$_1$-C$_8$ hydrocarbon; and (iv) when n is 2, and Y is O, R$_1$ through R$_3$ are not —CH$_2$CO$_2$H at all occurrences, or a pharmaceutically acceptable salt thereof.

14. The method of claim 13, wherein the effective amount inhibits aggregation of the p53 protein.

15. The method of claim 13, wherein the one or more p53 mutations comprise R248W mutation.

16. The method of claim 13, wherein the subject is human.

17. The method of claim 13, wherein the compound has the structure according to formula (II):

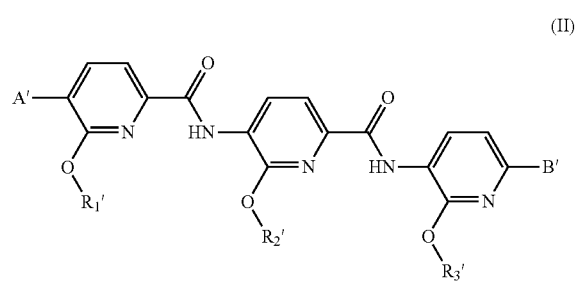

(II)

wherein R$_1$' is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof;

R$_2$' is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof;

R$_3$' is selected from a straight chained, branched or cyclic aliphatic C$_1$-C$_{20}$ hydrocarbon; an aromatic C$_6$-C$_{20}$ hydrocarbon; a heteroaromatic C$_1$-C$_{20}$ hydrocarbon; an aryl C$_6$-C$_{20}$ hydrocarbon; a heteroaryl C$_1$-C$_{20}$ hydrocarbon, a C$_1$-C$_{12}$ perfluorocarbon, or a combination thereof, each of which optionally contains 1-8 heteroatoms selected from halogen, O, N, and S, and each of which is optionally substituted with one or more of —NH$_2$; —NHR*; —N(R*)$_2$; —N(R*)$_3$$^+$; —(C=O)—R*; —CHO; —CO$_2$H; —CO$_2$R*; —(C=O)—S—R*; —O—(C=O)—H; —O—(C=O)—R*; and combinations thereof;

A' is selected from —NO$_2$; —NH$_2$; —NHR*; —N(R*)(C=O)—R*, —N(R*)$_2$, where R* is hydrogen or an aliphatic C$_1$-C$_{12}$ hydrocarbon; and B' is selected from —(C=O)—R*; —CO₂H; —CO₂R*, where R* is hydrogen or an aliphatic $C_1$-$C_{12}$ hydrocarbon;

R* is independently selected at each occurrence from hydrogen or $C_1$-$C_{12}$ hydrocarbons each of which optionally contains 1-8 heteroatoms selected from halogen, O, N, and S and combinations thereof;

with the proviso that (i) when $R_1$ and $R_3$ are both —CH₂CO₂H, $R_2$ is not —CH₂CO₂H or a straight chained, branched or cyclic aliphatic $C_1$-$C_{12}$ hydrocarbon, or $R_2$ does not have the structure —C[CH₂CO₂H]₃; and (ii) $R_1$ through $R_3$ are not each an unsubstituted $C_1$-$C_8$ hydrocarbon, or a pharmaceutically acceptable salt thereof.

18. The method of claim 13, wherein the compound has the structure according to the following formula:

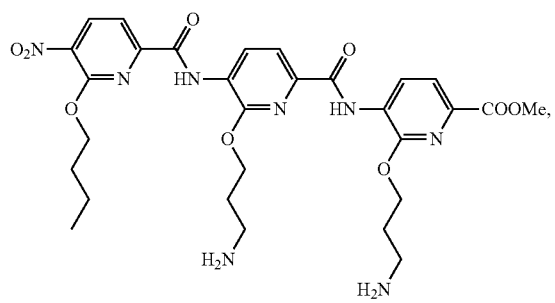 [SMILES: CCCCOc1nc(C(=O)Nc2ccc(C(=O)Nc3ccc(C(=O)OC)nc3OCCCN)nc2OCCCN)ccc1[N+](=O)[O-]]

or a pharmaceutically acceptable salt thereof.

19. The method of claim 13, wherein the compound has the structure according to the following formula:

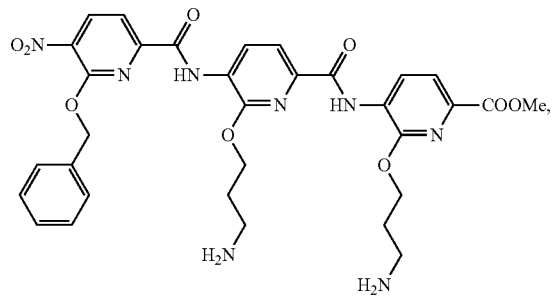 [SMILES: COC(=O)c1ccc(NC(=O)c2ccc(NC(=O)c3ccc([N+](=O)[O-])c(OCc4ccccc4)n3)c(OCCCN)n2)c(OCCCN)n1]

or a pharmaceutically acceptable salt thereof.

20. The method of claim 13, wherein the compound has the structure according to the following formula:

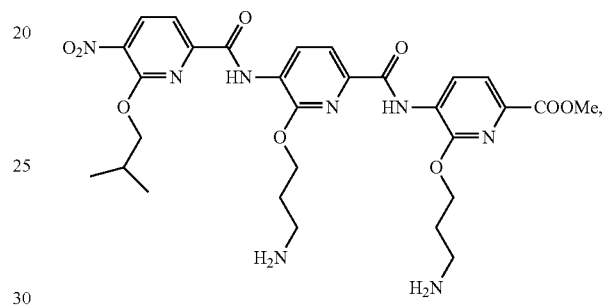

or a pharmaceutically acceptable salt thereof.

* * * * *